United States Patent [19]

Balaji et al.

[11] Patent Number: 5,331,573
[45] Date of Patent: Jul. 19, 1994

[54] METHOD OF DESIGN OF COMPOUNDS THAT MIMIC CONFORMATIONAL FEATURES OF SELECTED PEPTIDES

[76] Inventors: Vitukudi N. Balaji, 1642 Orchard Wood Rd.; Chandra U. Singh, 1213 Orchard Glen Cir., both of Encinitas, Calif. 92024

[21] Appl. No.: 628,111

[22] Filed: Dec. 14, 1990

[51] Int. Cl.[5] .......................................... G06F 15/42
[52] U.S. Cl. .................................. 364/500; 364/497; 364/578; 436/89
[58] Field of Search ............... 364/497, 499, 500, 578, 364/496; 436/89; 530/324, 325, 326

[56] References Cited

U.S. PATENT DOCUMENTS

| | | | |
|---|---|---|---|
| 4,852,017 | 7/1989 | Hunkapiller | 364/497 |
| 4,853,871 | 8/1989 | Pantoliano et al. | 364/496 |
| 4,881,175 | 11/1989 | Ladner | 364/496 |
| 4,908,773 | 4/1990 | Pantoliano et al. | 364/496 |
| 4,939,666 | 7/1990 | Hardman | 364/496 |
| 5,081,584 | 1/1992 | Ominichinski et al. | 364/497 |

OTHER PUBLICATIONS

*Science*, "Computerized Drug Design: Still Promising, Not Yet Here," Apr. 24, 1992, p. 441.
Pabo, C. O. and Suchenak, E. G., "Computer Aided Model-Building Strategies for Protein Design," *Biochemstry* 1986, V. 25 pp. 5987-5991.
Weinstein, Boris, *"Chemistrey and Biochemistry of Amino Acids, Peptides, and Proteins,"* 1983, pp. 267-357.
Ramachandran, et al., "Conformation of Polypeptides," *Adv. Prot. Chem.* 23, 283-437 (1968).
Szelke, et al., *In Peptides: Structure and Function, Proceedings of the Eighth American Peptide Symposium*, (Hruby and Rich, Eds.) pp. 579-582, Pierce Chemical Co., Rockford, Ill. (1983).
Allen, F. H., et al., *Acta. Crystallogr.*, B35:2231-2339 (1979).
Weiner, et al., "A New force Field for Molecular Mechanical Simulation of Nucleic Acids and Proteins", *J. Am. Chem. Soc.*, 106(3):765-84 (1984).
Cooper, et al., *J. Comput.-Aided Mol. Design*, 3:253-259 (1989).
Brint, et al., *J. Comput.-Aided Mol. Design*, 2:311-(1988).
Weiner, et al., *J. Comput. Chem.* 7:230-252 (1986).
Karplus, M., "Molecular Dyunamics: Applications to Proteins" in computer simulation of chemical and bimolecular systems, *Annals of the New York Acad. Science* 482:255-266 (1986).
Balasubramanian, R., "New type of representation for Mapping Chain Folding in Protein Molecules," *Nature* 266:856-857 (1974).
Kemp, D. S., "Peptidomimetics and the Template Approach to Nucleation of β-sheets and α-helices in Peptides," *Tibech* 8:249-255 (1990).

*Primary Examiner*—Kevin J. Teska
*Attorney, Agent, or Firm*—Pretty, Schroeder, Brueggemann & Clark

[57] ABSTRACT

A method of rational drug design includes simulating polypeptides in a way that predicts the most probable secondary and/or tertiary structures of a polypeptide, e.g., an oligopeptide, without any presumptions as to the conformation of the underlying primary or secondary structure. The method involves computer simulation of the polypeptide, and more particularly simulating a real-size primary structure in an aqueous environment, shrinking the size of the polypeptide isobarically and isothermally, and expanding the simulated polypeptide to its real size in selected time periods. A useful set of tools, termed Balaji plots, energy conformational maps, and probability maps, assist in identifying those portions of the predicted peptide structure that are most flexible or most rigid. The rational design of novel compounds, useful as drugs, e.g., bioactive peptidomimetic compounds, and constrained analogs thereof, is thus made possible using the simulation methods and tools of the described invention.

3 Claims, 36 Drawing Sheets

METHOD OF DESIGN OF COMPOUNDS THAT MIMIC CONFORMATIONAL FEATURES OF SELECTED PEPTIDES

A microfiche appendix containing 12 microfiche and 1164 frames is included as a part of the specification.

A portion of the disclosure of this patent document contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention relates to drug design, and more particularly to drug design achieved rationally through the simulation and prediction of conformational features of selected oligopeptides or polypeptides for the purpose of predicting and making bioactive peptidomimetic compound structures. The present invention further relates to methods and tools for making such predictions and compounds, and to the mammalian diagnostic and therapeutic uses of the compounds so produced.

BACKGROUND OF THE INVENTION

Proteins are complex, three-dimensional substances comprising one or more long, folded polypeptide chains. These chains, in turn, consist of small chemical units called amino acids. All amino acids contain carbon, hydrogen, oxygen, and nitrogen. Some also contain sulfur. A "peptide" is a compound that includes two or more amino acids. The amino acids link together in a line to form a peptide chain. There are 20 different naturally occurring amino acids involved in the biological production of peptides, and any number of them may be linked in any order to form a peptide chain. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Some peptide chains contain only a few amino acid units. Short peptide chains, e.g., having less than ten amino acid units, are sometimes referred to as "oligopeptides", where the prefix "oligo" signifies "few". Other peptide chains contain a large number of amino acid units, e.g., up to 100 or more, and are referred to a "polypeptides", where the prefix "poly" signifies "many". Still other peptide chains, containing a fixed number of amino acid units are referred to using a prefix that signifies the fixed number of units in the chain, e.g., an octapeptide, where the prefix "octa" signifies eight. (By convention, a "polypeptide" may be considered as any peptide chain containing three or more amino acids, whereas an "oligopeptide" is usually considered as a particular type of "short" polypeptide chain. Thus, as used herein, it is understood that any reference to a "polypeptide" also includes an oligopeptide. Further, any reference to a "peptide" includes polypeptides, oligopeptides, and the like.) Each different arrangement of amino acids forms a different polypeptide chain. The number of chains—and hence the number of different proteins—that can be formed is practically unlimited.

A drug is a chemical substance administered to a living organism with the intention of bringing about some desired result, such as preventing or curing disease. The desired result is usually achieved through an appropriate physical or chemical interaction between the administered drug and compounds found in living tissue.

All living things contain proteins. The structures of a cell are built of proteins. Some proteins, known as enzymes, speed up the chemical reactions of life. They help digest food, help produce energy, and assist in building other proteins. A single cell may contain many hundreds of enzymes. Other peptides and proteins, known as hormones, regulate chemical activities throughout the body. Still other proteins are antibodies that recognize and attach foreign bodies.

Drug design has historically involved "discovering" a particular chemical substance that interacts in some way with receptors, e.g., proteins in the living cells of a mammalian body. As proteins are made up of polypeptides, it is not surprising that some effective drugs are also peptides, or are patterned after peptides. Generally, for two peptides to effectively interact with each other, e.g., one as a protein receptor and the other as a drug, it is necessary that the complex three-dimensional shape ("conformation") of one peptide assume a compatible conformation that allows the two peptides to fit and bind together in a way that produces a desired result. In such instance, the complex shape or conformation of a first peptide has been compared to a "lock" and the corresponding requisite shape or conformation of the receptor as a "key" that unlocks (i.e., produces the desired result within) the first peptide. This "lock-and-key" analogy emphasizes that only a properly conformed key (second peptide or compound patterned thereafter) is able to fit within the lock (first peptide) in order to "unlock" it (produce a desired result). Further, even if the key fits in the lock, it must have the proper composition in order for it to perform its function. That is, the second peptide must contain the right elements in the right spatial arrangement and position in order to properly bind with the first peptide, e.g., receptor protein. Discovering or predicting the proper conformation or shape of the key, or second peptide or compound patterned thereafter, is thus a major objective of any drug design.

To better understand and appreciate the obstacles involved in discovering or predicting the conformation of an oligopeptide or polypeptide, reference is made to FIG. 1 where the conventional chemical representation of a neutral oligopeptide, consisting of four amino acids, is shown. Depending on the pH of the medium in which the peptide is present, the peptide can contain a variety of charged species, i.e., one or more ammonium species, carboxyl anions, etc. Note that the molecule represented in FIG. 1 has a terminal amino ($NH_2$) group at the left end of the chain, as oriented in the figure, and a terminal free carboxyl (—COOH) group at the right end of the chain. These ends of the polypeptide are called the amino ($NH_2$) terminal end and the carboxyl (—COOH) terminal end, respectively. This same terminology applies in the case of proteins. By convention, the $NH_2$-terminal amino acid in an oligopeptide of the polypeptide chain of a protein is called the first amino acid or the first "residue". The next amino acid in the chain is called the second amino acid or the second residue, and so on, throughout the length of the chain.

The R groups shown in FIG. 1, i.e., $R^1$, $R^2$, $R^3$, and $R^4$, symbolize various "pendant groups" of the chain. The pendant groups are always attached to the alpha carbon ($C^\alpha$) atom (i.e., to the carbon-hydrogen (CH) component of the chain, as shown in FIG. 1). A pendant group may comprise a simple or complex group or moiety, having physical dimensions that can vary significantly compared to the dimensions of the chain.

There are a number of factors that play important roles in determining the total structure of a protein or polypeptide. First, the peptide bond, i.e., that bond which joins the amino acids in the chain together, is a covalent bond. This bond is planar in structure, being essentially a substituted amide. An "amide" is any of a group of organic compounds containing the radical:

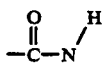

The planar peptide bond may be represented as depicted in FIG. 2. Because the O=C and the C—N atoms lie in a relatively rigid plane, free rotation does not occur about these axes. Hence, a plane, schematically depicted in FIG. 2 by the dotted line 12, and sometimes referred to as an "amide plane" or "peptide plane", is formed wherein lie the oxygen (O), carbon (C), nitrogen (N), and hydrogen (H) atoms of a given amino acid or residue. At opposite corners of this amide plane are located the α-carbon ($C^\alpha$) atoms. Since there is substantially no rotation about the rigid O=C and C—N atoms in the peptide or amide plane, a polypeptide chain thus comprises a series of planar peptide linkages joining the $C^\alpha$ atoms. The $C^\alpha$ atoms thus serve as swivel points or centers for a polypeptide chain as shown in FIG. 2B. In FIG. 2B, the shaded areas 12 represent the peptide or amide planes. Note that each plane is coupled to the adjacent plane through a $C^\alpha$ atom.

A second factor that plays an important role in defining the total structure or conformation of a polypeptide or protein is the angle of rotation of each amide or peptide plane about the common $C^\alpha$ linkage. Advantageously, assuming that the O, C, N and H atoms remain in the amide plane (which is usually a valid assumption, although there may be some slight deviations from planarity of these atoms for some conformations), these angles of rotation completely define the polypeptide's structure, at least the structure as it exists between adjacent residues. These angles of rotation are illustrated in FIG. 2C. In FIG. 2C, two amide planes are shown, represented by the dotted lines 12' and 12". These two planes are joined by a common $C^\alpha$ atom 13 that is the corner of each plane. The angle of rotation of the plane 12' relative to the common $C^\alpha$-atom 13 is defined as $\phi$. The angle of rotation of the plane 12" relative to the $C^\alpha$ atom 13 is defined as $\psi$. The two angles $\phi$, $\psi$ thus substantially define the peptide structure for the main chain of a particular residue of the peptide chain. A set of the angles $\phi_i$, $\psi_i$ where the subscript i represents a particular residue of a polypeptide chain, thus effectively defines the total polypeptide secondary structure.

It is noted that the conventions used in defining the $\phi$, $\psi$ angles, i.e., the reference points at which the amide planes form a zero degree angle, and the definition of which angle is $\phi$, and which angle is $\psi$, for a given polypeptide, are defined in the literature. See, e.g., Ramachandran et al., "Conformation of Polypeptides," Adv. Prot. Chem. 23, 283-437 (1968), at pages 285-94, which pages are incorporated herein by reference.

Thus, a polypeptide structure bends, folds or flexes at each $C^\alpha$ swivel point. In a particular environment, and depending upon the particular side chains that may be attached to the polypeptide, some of these bends or folds may be stable, i.e., the $\phi$, $\psi$ angles will not change. In many environments, however, the $\phi$, $\psi$ angles will not be stable, and the polypeptide chain will dynamically fold and bend (much as a snake swimming in water) as subjected to external or internal forces. Such forces may originate from numerous sources, such as ions, or molecules in the medium wherein the polypeptide is located (external forces) that either attract or repel a given atom or group of atoms within the polypeptide. Often, however, these forces originate from within the polypeptide itself, or within one of its pendant groups, as the chain folds back on itself and one residue or pendant group of the polypeptide comes in close proximity to another residue or pendant group chain of the polypeptide.

To illustrate the manner in which a polypeptide chain may bend or fold, FIG. 3A conceptually shows a polypeptide that has assumed a helical conformation. The helix shown in FIG. 3A is a specific configuration called the right-handed α helix. This structure, exhibiting 3.6 amino acid residues per turn, is representative of numerous known stable peptide structures. Stability results due to hydrogen bonding between an —NH— group in the helix and the —C=O group of the fourth amino acid down the chain. Under the conditions shown in FIG. 3A, the $\phi$ value is about −60°, and the $\psi$ value is about −40°.

Since the $C^\alpha$ atom is the swivel point for the chain, the R groups (side or pendant groups) associated with the $C^\alpha$ atom become extremely important in defining the ultimate peptide conformation.

In general, just as a flexible rope can assume an infinite number of shapes, including highly symmetrical shapes, such as a helix, or asymmetrical shapes involving all kinds of contortions, a polypeptide chain can conceptually also assume an infinite number of shapes. Many of the possible shapes, however, are unstable, because the internal and external molecular attraction and/or repulsion forces will not permit such shapes to persist. These forces act to move or change the polypeptide conformation away from unstable conformations toward a stable conformation. A stable conformation is one where the internal and external molecular attraction and/or repulsion forces fail to destabilize or push the existing conformation toward another conformation.

Most polypeptide structures exhibit several conformations that are stable, some more so than others. The most stable conformations are the most probable. A conformation may change from one stable conformation to another through the application of sufficient energy to cause the change. Given the opportunity to freely move, fold and/or bend, a given polypeptide chain will eventually assume a stable conformation. The most probable conformation that is assumed is the one that would take the most energy to undo. This most probable conformation is referred to herein as the "global minimum". Other stable conformations are less probable, but may readily be assumed, and are referred to herein as a "local minimum" or "local minima". A conformation that represents a local minimum could thus be changed, through application of an external force, to another stable conformation which is either another, different local minimum or the global minimum. Being able to distinguish whether a given conformation represents a local minimum or the global (or most probable) minimum remains a significant problem when peptide simulation is performed.

Shown in FIG. 3B is a complex three-dimensional conformation of a polypeptide, typical of many proteins, stabilized by noncovalent bonds. Shown in FIG. 3C are two such complex polypeptide conformations, closely packed with each other. FIG. 3C is thus illustrative of the "lock-and-key" analogy associated with drug design. Only by designing the conformation of one peptide to allow it to fit within the conformation of the other peptide and bind thereto will the desired interaction between the two peptides take place. Rational drug design thus includes not only knowing or predicting the conformation of a desired protein receptor peptide, but also being able to control and predict the conformation of a drug peptide that is to interact with the receptor peptide.

At this juncture, it will be helpful to define some common terms used to define the complex structure of proteins and polypeptides. A primary structure is one wherein the number and precise sequence of amino acids in the polypeptide is known. The peptide linkage between each of the amino acid residues is implied, but no other forces or bonds are indicated by use of the term "primary structure". Thus, the chemical representation of the peptide shown in FIG. 1 defines its primary structure. A secondary structure refers to the extent to which a polypeptide chain possesses any helical or other stable structure, such as shown in FIG. 3A. A secondary structure will thus have a set of angles, $\phi_i, \psi_i$ for each residue i of the chain. A tertiary structure is a term used to refer to the tendency for the polypeptide to undergo extensive coiling or folding to produce a complex, somewhat rigid three-dimensional structure, such as is shown in FIG. 3B. A quaternary structure is a term used to define the degree of association between two or more polypeptides, e.g., between two tertiary structures, such as a target peptide and a receptor, as suggested by FIG. 3C.

To the four basic structures defined above, some authors have further described and coined terms for intermediate structures, e.g., supersecondary and domain structures. Whereas a secondary structure is used to refer to the regular arrangements of the polypeptide backbone, a "supersecondary" structure is used to define aggregates of the secondary structure. "Domain" structures are used to refer to well-separated parts within globular proteins, i.e., within tertiary structures. See, e.g., Linderstrom-Lang, et al., "Protein Structure and Enzyme Activity, " The Enzymes, (P. D. Boyer, Ed.), 1:443–510, Academic Press, New York (1959); and Schulz et al., Principles of Protein Structure, Springer-Verlag, New York (1984).

Those skilled in the art will recognize that the above description of a polypeptide chain and the factors that define its total structure are somewhat simplified. However, the above description nonetheless provides a sufficient background for understanding the present invention. For a more thorough description of polypeptide structure, see, e.g., Ramachandran et al., "Conformation of Polypeptides," *Adv. Prot Chem.* 23, 283–437 (1968).

With the foregoing as background, it is thus seen that drug design involving polypeptides requires identifying and defining a first peptide with which the designed drug is to interact, and using the first target peptide to define the requirements for a second peptide. With such requirements defined, the goal is then to find or prepare an appropriate peptide or non-peptide ligand that meets all or substantially all of the defined requirements which can hopefully be used as the administered drug.

As a practical matter, however, this process of drug design has proven to be very difficult. In the first place, many of the protein peptides with which the administered drug is to interact do not themselves exhibit stable conformations, so it is difficult to use such protein peptides in trying to set the requirements for a drug peptide. While a particular application, e.g., a particular protein peptide, may provide some clues as to an appropriate primary or secondary structure that an administered drug peptide might assume, it may provide few clues as to the best conformation for the drug peptide. Further, even if a desired conformation of a compound of interest were identifiable, being able to administer such compound to a patient in a form which maintains such conformation may not be possible. That is, for a given application, a preferred conformation of the compound of interest may not be sufficiently stable to impart the desired effect to the recipient organism.

In view of the above difficulties, the best that has been achieved to date in rational drug design is to search for an appropriate compound that could be administered as a drug and that provides a stable secondary or tertiary structure. Once identified, this compound is tested to see if it is bioactive (i.e., to see if it has the capacity to interact with a desired receptor peptide). If so, it is further tested to see if the desired beneficial results are achieved.

Thus, much of the drug design heretofore conducted has involved intensive efforts aimed at searching for bioactive peptides and testing any that are so identified. It is thus evident that what is needed is a method or technique of predicting the best conformation for a peptide drug; and, once found, providing a means for maintaining this conformation so that it can be further tested, e.g., for bioactivity.

The process of drug design is further complicated by the metabolic degradation of the amide bonds of many polypeptide chains. That is, even assuming a given peptide drug having a desired conformation is identified, and further assuming that this desired conformation can be maintained, the actual peptide bonds linking the amino acid residues in the peptide chain may break apart when the peptide drug is orally administered. Once such bonds are broken, all that is left are portions (moieties) of the polypeptide chain which do not provide the needed conformation for the peptide drug to perform its intended task (i.e., the "key" has broken apart, and a broken key is not able to unlock the lock). Hence, a method or technique is needed for preventing the amide bonds of a peptide drug from breaking down, prior to the realization of the desired effect, upon administration of the peptide drug. In other words, it is desired that the peptide drug survive in its active form until it reaches the site where it exerts its biological effect.

Several techniques are known in the art in an attempt to address the above problems. For example, it is known in the drug design art to look for a substitute compound that mimics the conformation and desirable features of a particular peptide, e.g., an oligopeptide, once such peptide has been found, but that avoids the undesirable features, e.g., flexibility (loss of conformation) and bond breakdown. Such a compound that mimics a peptide is known as a "peptidomimetic". For example, morphine is a compound which can be orally administered, and which is a peptidomimetic of the peptide endorphin. However, to date, only limited success has been reported in these attempts, largely because it has been so difficult to identify the desired starting point, i.e., the conformation of the particular oligopeptide or other peptide that is to be mimicked. See, e.g., Spatola, A. F. *Chemistry and Biochemistry of Amino Acids, Peptides, and Proteins* (Weistein, B, Ed.), Vol. 7, pp. 267–357, Marcel Dekker, New York (1983), which describes the use of the methylenethio bioisostere [$CH_2S$] as an amide replacement in enkephalin analogues; and Szelke et al., *In peptides: Structure and Function, Proceedings of the Eighth American Peptide Symposium*, (Hruby and Rich, Eds.); pp. 579–582, Pierce Chemical Co., Rockford, Ill. (1983), which describes renin inhibitors having both the methyleneamino [$CH_2NH$] and hydroxyethylene [$CHOHCH_2$] bioisosteres at the Leu-Val amide bond in the 6–13 octapeptide derived from angiotensinogen. Hence, what is needed is a rational approach for identifying the most probable starting point for the design of a bioactive peptidomimetic.

It is also known in the art to use computer simulation in an attempt to predict a stable conformation of a peptide. That is, because a peptide is a sequence of amino acid residues, each containing known atoms bonded together in known molecules having known bonding lengths, with known electrostatic properties associated with each atom, it is possible to simulate a peptide structure on the computer. However, the difficulty with such computer simulations to date has been the propensity of such simulations to identify only "local minimum" conformations of the subject peptide, since the most probable conformation of the peptide may fall outside some of the parameters assumed for purposes of carrying out the simulation calculations. In addition, there is typically an enormous amount of computer time required to systematically examine all possible conformational possibilities of the peptide, particularly when more than just a short peptide is being simulated.

In order to shorten the amount of computer time required in such simulations, it is known to specify a starting point, e.g., a good estimate of the conformation of the stable peptide having a known amino acid sequence. Such estimate may be based on known data, e.g., as obtained using X-ray crystallography, or as predicted using model building of three-dimensional structures of homologous proteins when the three-dimensional structure of at least one of the proteins in the structure is known. Unfortunately, while such "starting points" do significantly shorten the amount of computer time required in such simulations, they also bias the final results. Frequently, such simulations end up identifying only a "local minimum" of the predicted peptide, with the most probable stable conformation of the peptide going undetected. What is clearly needed, therefore, is a method and technique of predicting the most probable stable peptide conformations using computer simulations that may be feasibly performed and that do not bias the final results.

The present invention advantageously addresses the above and other needs associated with drug design.

SUMMARY OF THE INVENTION

In accordance with one aspect of the present invention, there is provided a method of rational drug design that identifies bioactive peptidomimetics that can be effectively used as drugs. Such method includes: (a) simulating the most probable conformations of a given polypeptide; (b) selecting the most probable conformation of the peptides thus simulated; (c) designing and synthesizing a chemically modified analog of the selected peptide; (d) evaluating the bioactivity of the synthesized chemically modified analog; and optionally (e) designing a suitable peptidomimetic based on the conformation of the synthesized chemically modified analog. As employed herein, the term "chemically modified analog" refers to a synthetic peptide or peptide-like compound which has been altered, relative to the initial peptide, so as to alter the chemical stability of said peptide (e.g., increase the metabolic stability), to enhance the pharmacokinetic properties of said peptide (e.g., to increase absorption, distribution and/or elimination of said peptide), to enhance the potency of said peptide, to enhance the bioavailability of said peptide, to improve the ease of synthesis of said peptide, and/or to enhance the ease of administration of said peptide.

In accordance with another aspect of the invention, a method of predicting the most probable tertiary structure of a peptide is provided without any presumption regarding the underlying structural characteristics of the peptide. Such method is referred to herein as an "ab initio" method, where the term is used to emphasize there are no initial presumptions made as to what form the simulated tertiary structure may ultimately take. Thus, in the absence of physical or chemical data that might otherwise indicate the most probable conformation of a peptide of interest, this method may advantageously be used as the first step of the rational drug design method described herein.

The ab initio technique utilized by the present invention includes the steps of: (a) simulating a real-size primary structure of a polypeptide in a solvent box (e.g., in an aqueous environment); (b) shrinking the size of the peptide isobarically and isothermally; and (c) expanding the peptide to and beyond its real size in selected time periods, while measuring the energy state and coordinates, e.g., the $\phi$, $\psi$ angles, of the expanding molecule(s). As the peptide expands to its full size and beyond, it assumes a stable tertiary structure. In most cases, due to the manner in which the expansion occurs, this tertiary structure will be either the most probable structure (i.e., will represent a global minimum for the structure), or one of the most probable structures. In any event, repetition of the ab initio technique and/or further analysis of the tertiary structure thus obtained, e.g., using conformational energy plots and/or Balaji plots as described hereinafter, provides a further measure of the probability of occurrence of the structure.

Advantageously, three protocols of the ab initio technique of the invention may be selectively practiced. In a first protocol, the residues of the peptide chain are shrunk and then expanded one at a time. In a second protocol, the entire peptide chain is shrunk and expanded simultaneously. In a third protocol, known physical and/or chemical data, if any, is used to bias the simulation towards a known result.

Yet another aspect of the invention provides new analytical tools or methods for greatly simplifying the analysis and understanding of the complex three-dimensional tertiary structures of polypeptides or peptidomimetics. One new analytical tool is referred to herein as a "Balaji plot", and provides a significant improvement over similar tools or plots known in the art. Advantageously, the data required to generate the "Balaji plot" is automatically generated while performing the ab initio method of the invention, or can be obtained from other sources. This data includes the $\phi$, $\psi$ angles for each residue of the peptide as it expands to and beyond its normal size. The Balaji plot is used for: (a) identifying the relative proportional residence time adopted by a particular tertiary structure of a simulated peptide or peptidomimetic; (b) determining sequences or areas of flexibility and rigidness in such peptides or peptidomimetics; and (c) providing instructions and/or insight into the manner in which rigid, constrained or flexible peptide analogs should be modeled, e.g., by computer generation. The Balaji plot thus represents a valuable tool that may be used to assist in carrying out the steps of selecting the most probable peptide conformation, and designing and synthesizing a chemically modified analog of the selected peptide in accordance with the rational drug design method described herein. Other analytical tools useful for identifying the most probable tertiary structure of a polypeptide include a conformational energy map and a contour probability map, both of which may be generated using the computer simulation technique herein described.

Still another aspect of the invention provides for simulating the growth or expansion of a protein compound within an acceptor binding site when the acceptor geometry is known, but the mode of protein-acceptor binding is not known, thereby facilitating a better understanding of the binding event, and thus further enhancing the rational drug design.

Further, the invention includes a data base of conformational features of constrained peptides, as well as the methods and techniques for accessing such a data base for use in simulating peptidomimetics. The peptidomimetics are simulated through, e.g., modification of the backbone and/or side chains of selected target peptides.

Advantageously, each of the steps of the rational drug design method of the present invention may be carried out as one step in the overall drug design method of the invention, or as separate procedures or processes independent of the other steps for the purpose of evaluating a particular peptide, peptidomimetic, or groups of the same. For example, the ab initio process of the invention, used as a first step of simulating the most probable conformation of a peptide, may also be used to simulate any peptide, whether short or long. Further, such simulation may be used to build up a data base of probable conformations for a set of peptides of interest.

Similarly, the second step of the overall method, related to selecting the most probable conformation of the simulated peptides, may also be used by itself to examine the already existing peptide data in order to determine which of the several possible conformations is the most probable, which of the amide bonds of a defined peptide is the most flexible, and therefore which of the amide bonds might be replaceable by a more rigid bioisostere in order to provide a more stable conformation.

Advantageously, all of the peptides or peptidomimetic simulations performed in accordance with the present invention may be readily carried out using a computer by those skilled in the art. Due to the large number of calculations involved, it is preferred that the computer be a "supercomputer", e.g., a computer having a large memory and capable of performing calculations at high speed using parallel processing. However, any computer or processing system capable of performing the needed calculations and computations, one at a time, can be used to assist in carrying out the present invention.

It is thus a feature of the present invention to provide a method of rational drug design that overcomes or minimizes the problems mentioned above in the "Background of the Invention" associated with prior art drug design methods.

It is a further feature of the invention to provide a method of rational drug design that identifies bioactive peptidomimetics that can be effectively used as drugs.

It is another feature of the invention to provide a simulation method that predicts the most probable tertiary structure(s) of a polypeptide, e.g., an oligopeptide, as defined by the backbone structure of a primary or secondary structure.

Still another feature of the invention provides analytical tools for readily identifying those portions of a predicted peptide structure that are the most flexible and/or the most chemically modified, and that provides additional insight into understanding peptide tertiary and quaternary structures.

Yet another feature of the invention allows the flexible portions of the structure to be replaced with suitable bioisosteres or equivalent, so that a desired conformation, once predicted, can be maintained. As employed herein, the term "bioisostere" refers to atoms or groups of atoms which are of similar size to the atom or group of atoms which are to be replaced, wherein the compound containing the replacement atom or group of atoms retains, to a substantial degree, the biological activity of the original, unmodified peptide. See, for example, Nelson, Mautner, and Kuntz, at pp. 227, 271 and 285, respectively, in *Burger's Medicinal Chemistry*, Part 1, the Basis of Medicinal Chemistry, 4th Edition, M. E. Wolff, ed. (John Wiley & Sons, N.Y., 1980).

Further, it is a feature of the invention that any portions or sections of the peptide structure subject to degradation when the peptide is administered, may likewise be replaced with bioisosteres or equivalent that are not degraded and that maintain the desired binding.

It is still another feature of the invention to provide a drug simulation method and system that can be performed using a computer.

It is yet another feature of the invention to provide a means for identifying the most probable starting point for the design of a bioactive peptidomimetic compound.

BRIEF DESCRIPTION OF THE DRAWINGS

The above and other aspects, features and advantages of the present invention will be more apparent from the following more particular description thereof, presented in conjunction with the following drawings and wherein:

FIG. 1 shows the chemical representation of a typical short peptide chain,

FIG. 2A illustrates the amide planar bond in a peptide,

FIG. 2B illustrates those portions of a peptide chain that are constrained within the amide plane, and further illustrates how such planes join at the $C^\alpha$ atoms of the peptide chain, FIG. 2C defines the $\phi$, $\psi$ angles of a particular amino acid residue within the peptide chain, FIG. 3A shows a peptide chain in a helical structure, and is representative of a secondary structure, FIG. 3B schematically illustrates the complex, three-dimensional shape of a tertiary structure, and FIG. 3C is a schematic representation of a quaternary structure.

FIG. 9B depicts contour probability data for a model compound as generated by the present invention;

| Min. # | Global minimum occurs at $\theta_1$, $\theta_2$ = 70°, −90° (energy = 28.3 kcal/mol) | | |
|---|---|---|---|
| | $\theta_1$ (°) | $\theta_2$ (°) | |
| 1 | 70 | −90 | 0.0 |
| 2 | −70 | 90 | 0.0 |
| 3 | 60 | 50 | 0.2 |
| 4 | −60 | −50 | 0.2 |
| 5 | 70 | −170 | 0.4 |
| 6 | −70 | 170 | 0.4 |
| 7 | −180 | −70 | 1.5 |
| 8 | −180 | 70 | 1.5 |
| 9 | 180 | −70 | 1.5 |
| 10 | 180 | 70 | 1.5 |
| 11 | 180 | −180 | 2.3 |
| 12 | −180 | 180 | 2.3 |
| 13 | 180 | 180 | 2.3 |
| 14 | −180 | −180 | 2.3 |

Percent occupation of the 1 to 5 kcal/mol energy contours in the $\theta_1$, $\theta_2$ space derived from conformational energy map:
9  26  43  60  77
Line thickness of contours coded according to energy (thickest = 1 and thinnest = 5). Shaded areas correspond to energy >6.5 kcal/mol.

10 Relative energy in kcal/mol (global minimum set to 0.0).

Figure 13A:
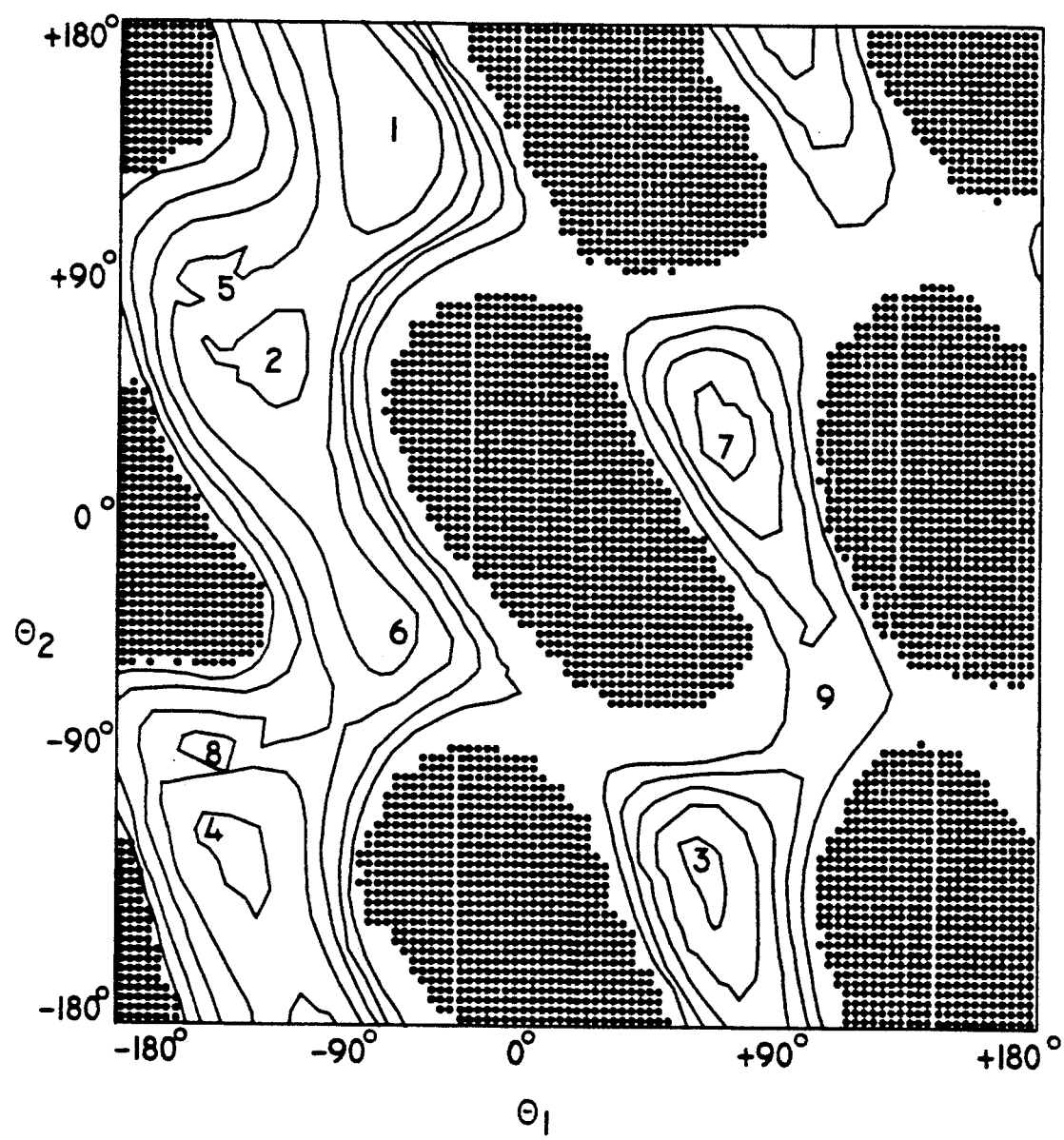
Figure 13B:
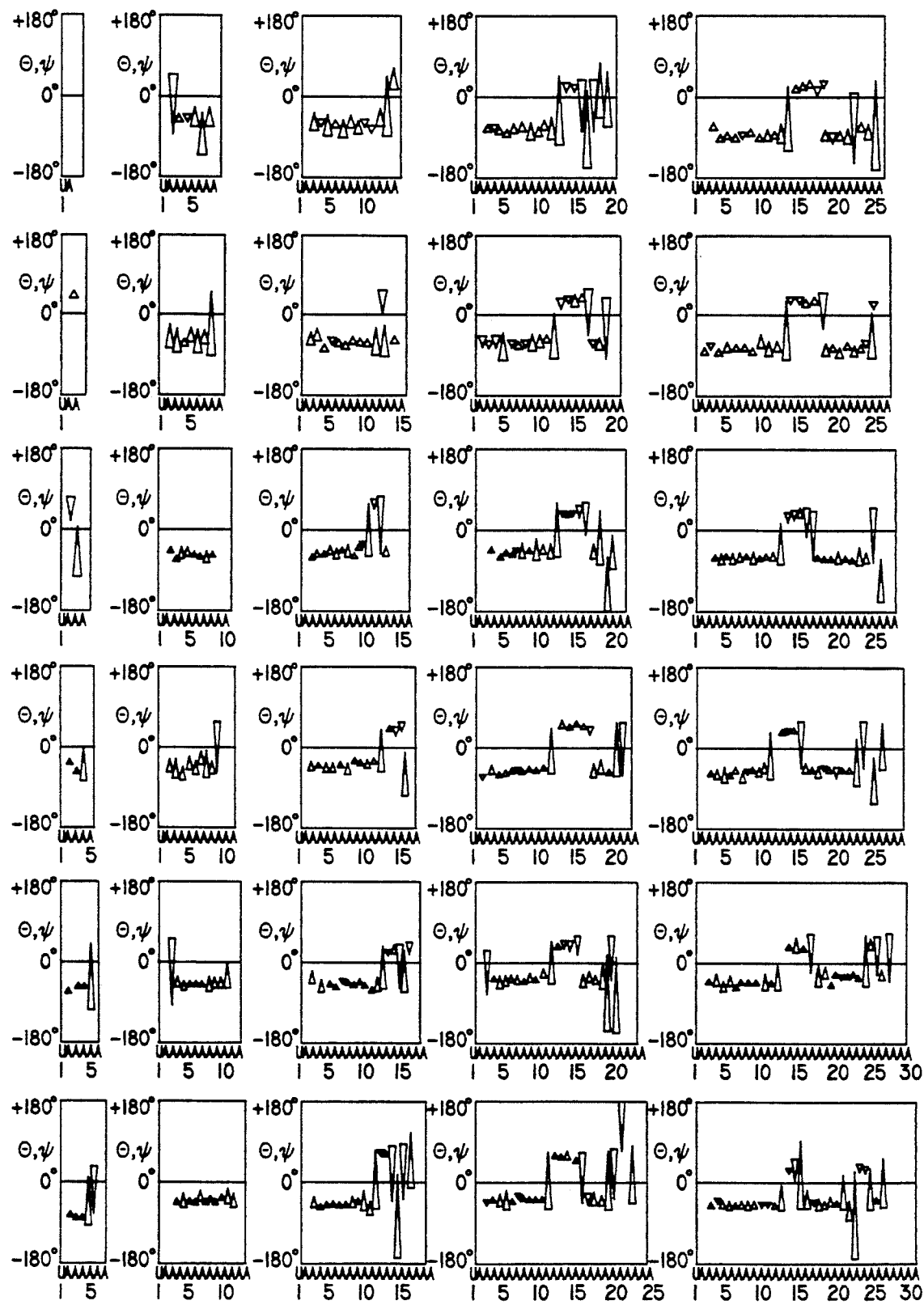
Figure 14:
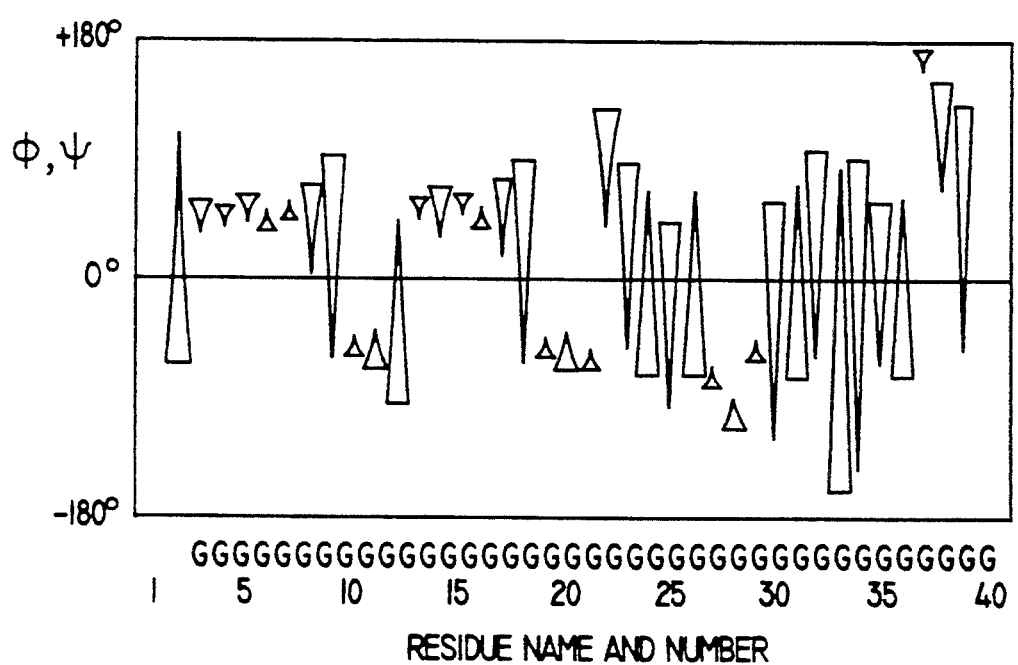
Figure 15:
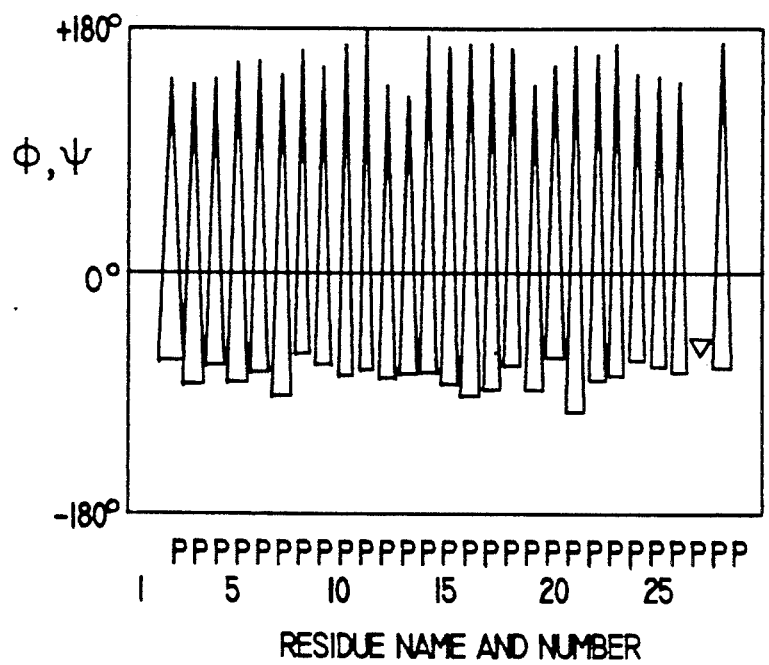
Figure 16:
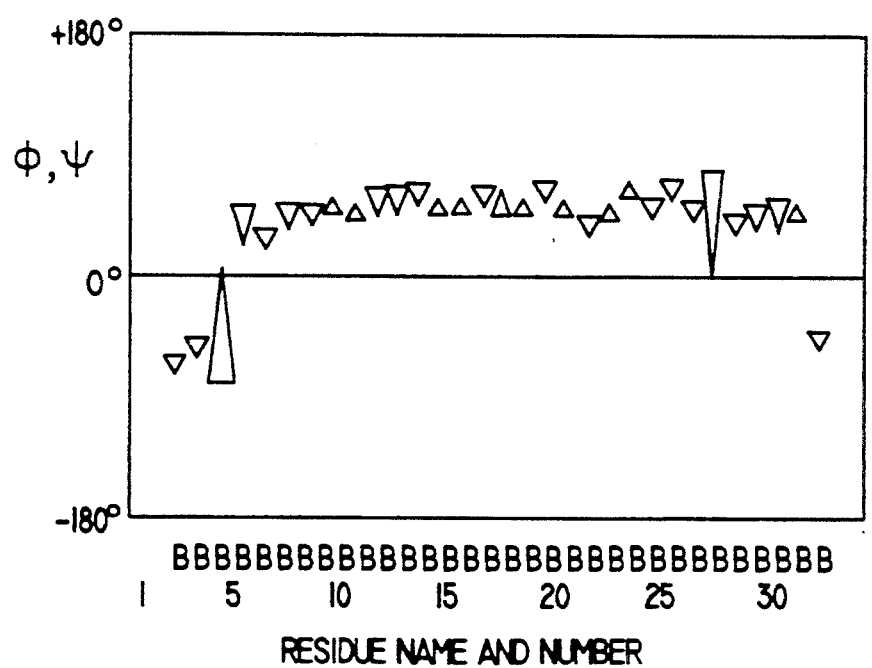
Figure 15A:
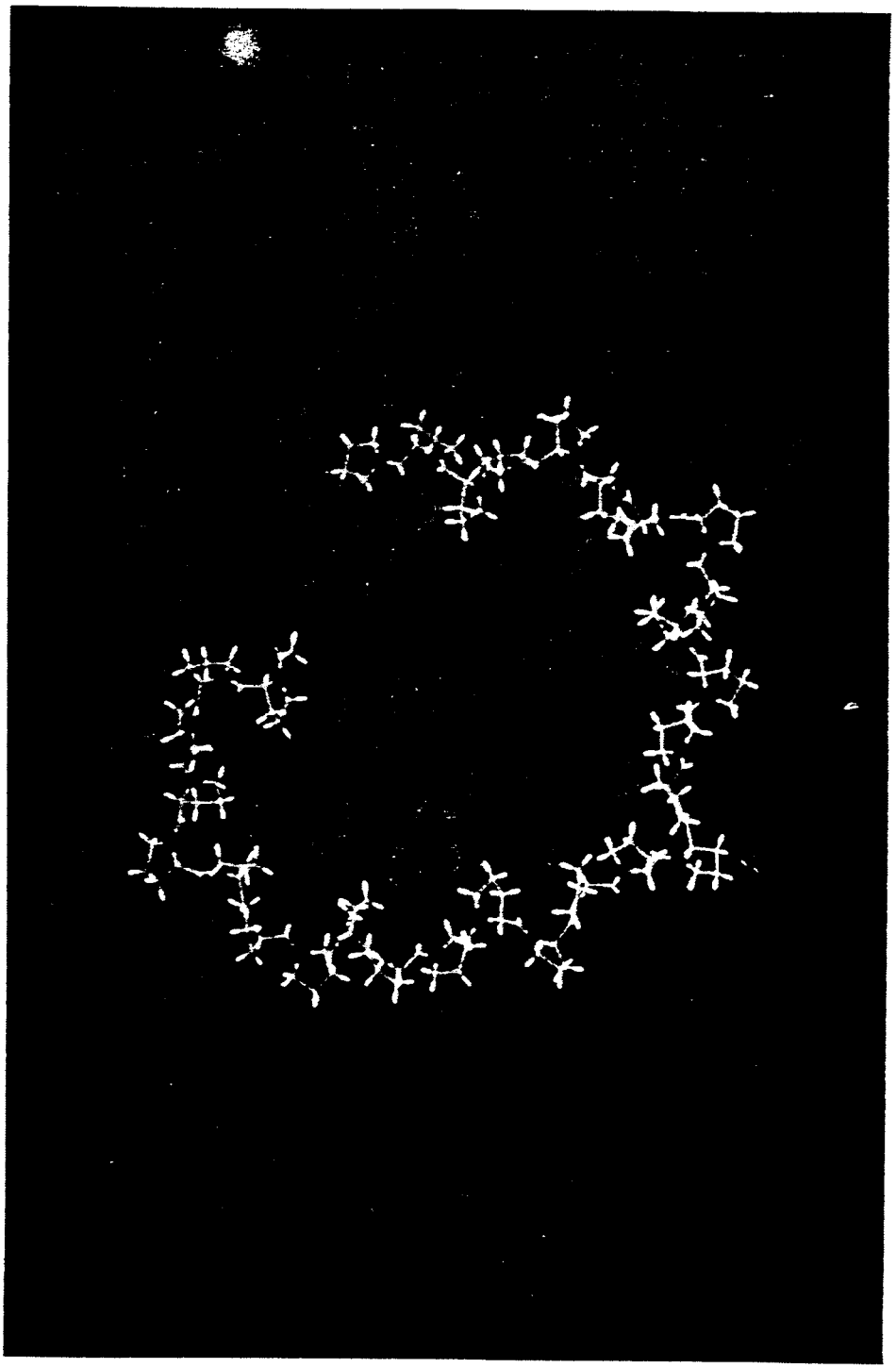
Figure 17A:
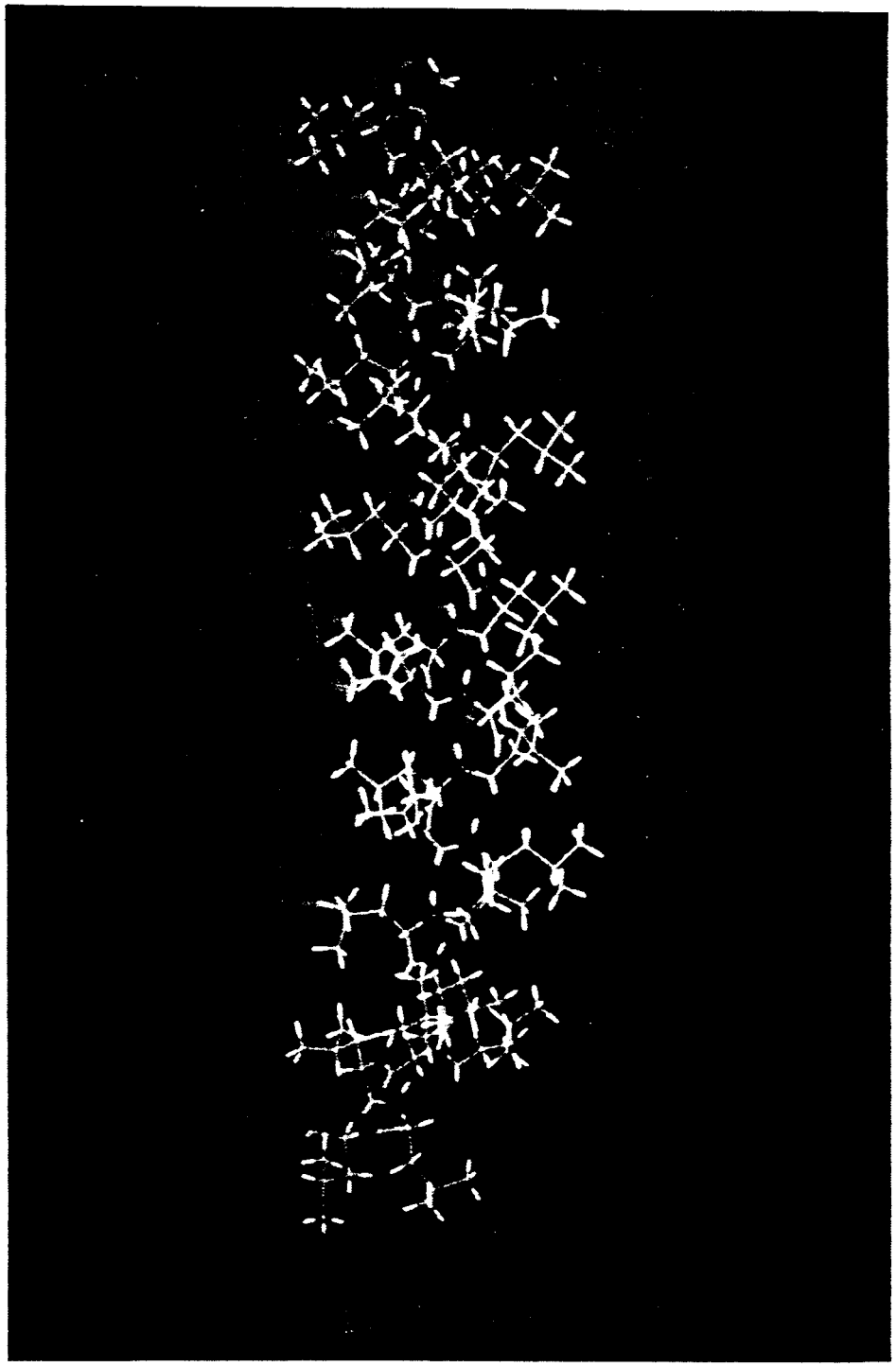
Figure 17:
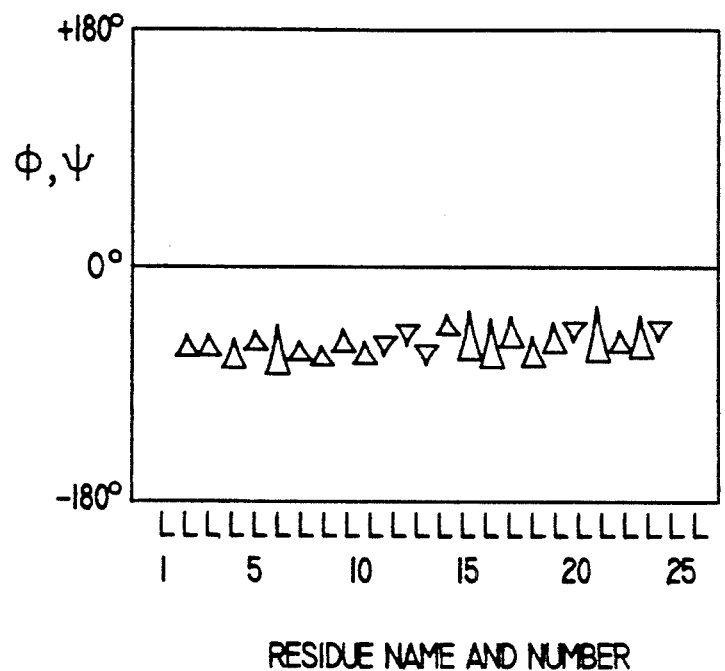
Figure 18:
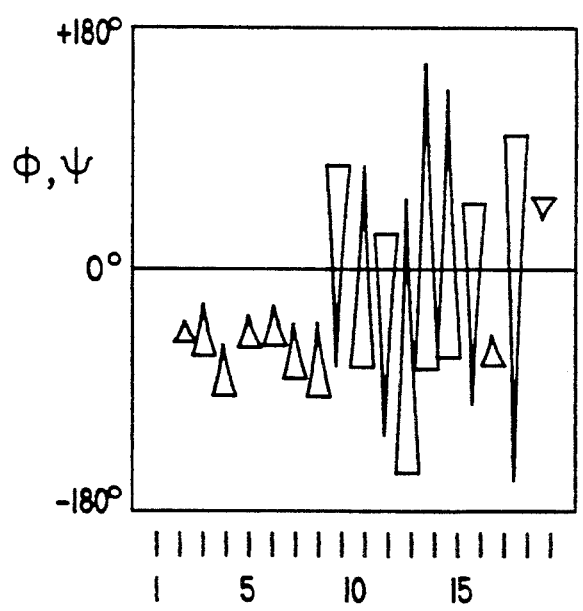
Figure 18A:
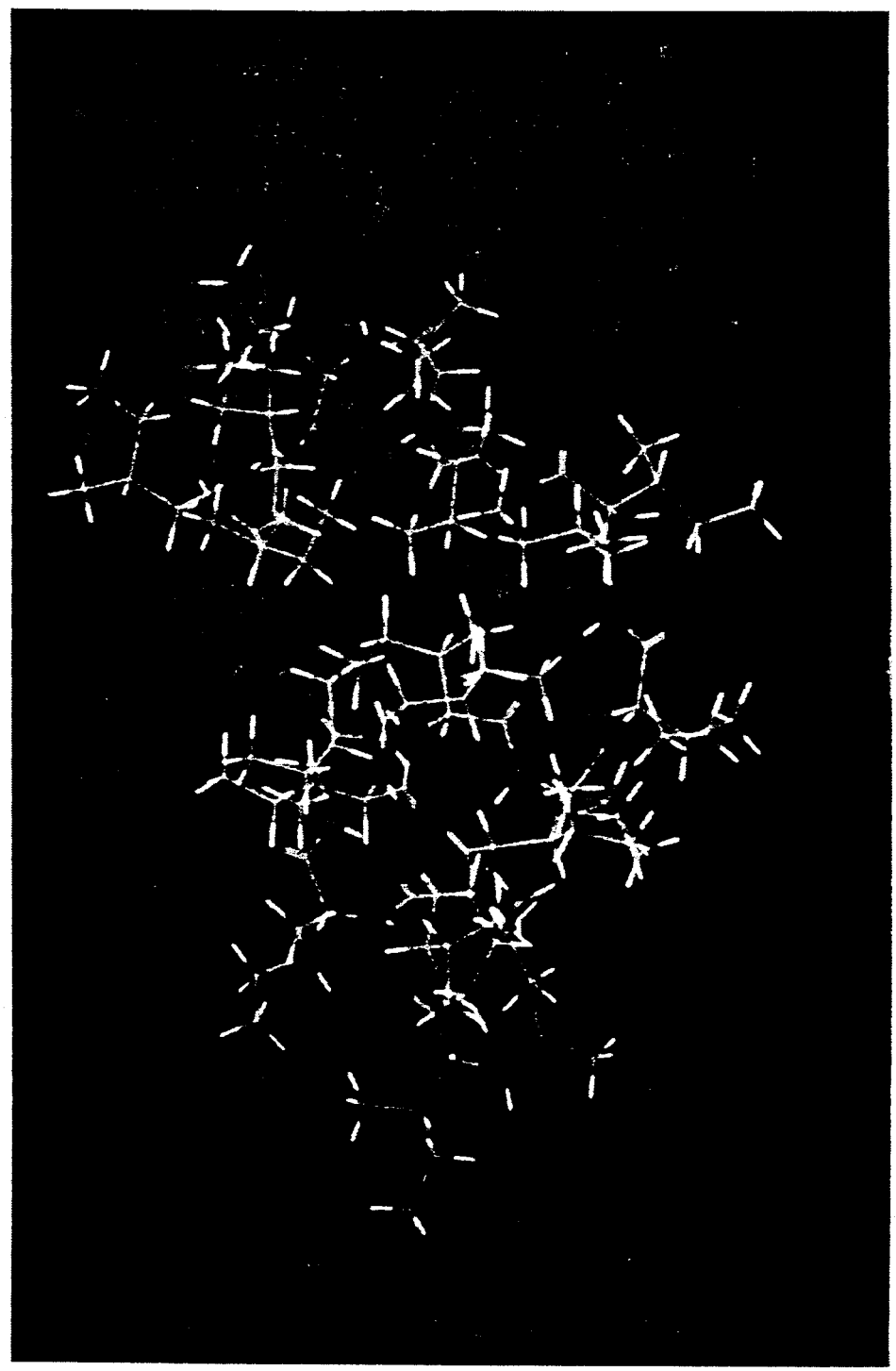

FIG. 13A shows a conformational energy map for an L-alanyl dithiopeptide;

FIG. 13B is a series of Balaji plots of poly-L-alanine as it is grown residue-by-residue;

FIG. 14 is a Balaji plot of polyglycine;

FIG. 15 is a Balaji plot of poly-L-proline;

FIG. 15A is a graphic display showing a three-dimensional peptide structure calculated for poly-L-proline;

FIG. 16 is a Balaji plot of poly(Aib);

FIG. 17 is a Balaji plot of poly-L-leucine;

FIG. 17A is a graphic display showing a three-dimensional peptide structure calculated for poly-L-leucine;

FIG. 18 is a Balaji plot of poly-L-isoleucine;

FIG. 18A is a graphic display showing a three-dimensional peptide structure calculated for poly-L-isoleucine.

Figure 19:
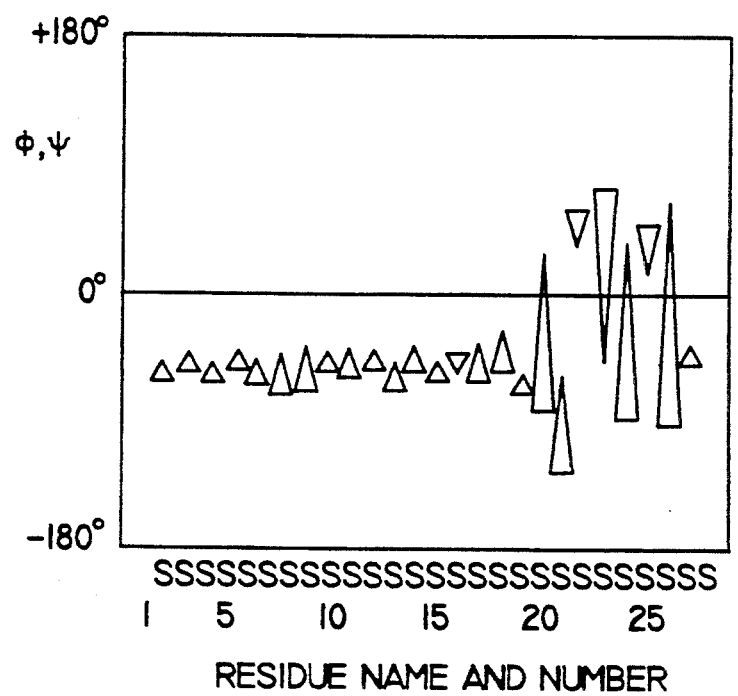
Figure 20:
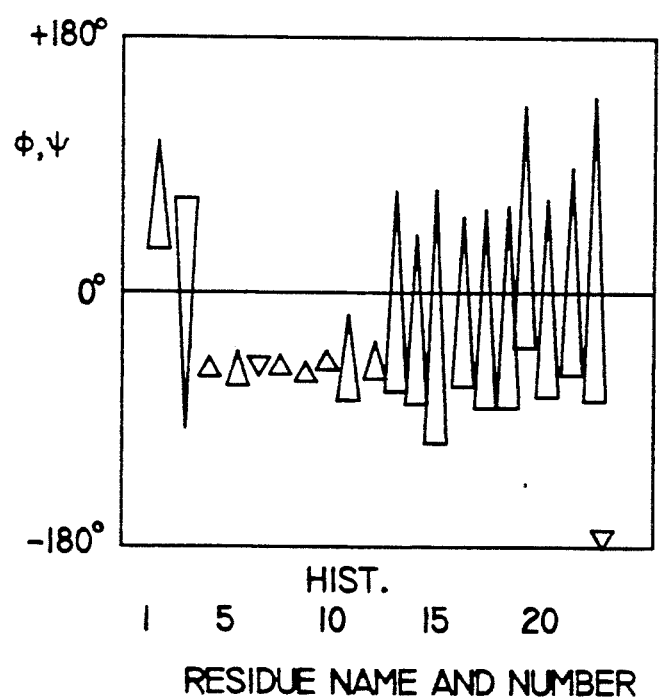
Figure 21:
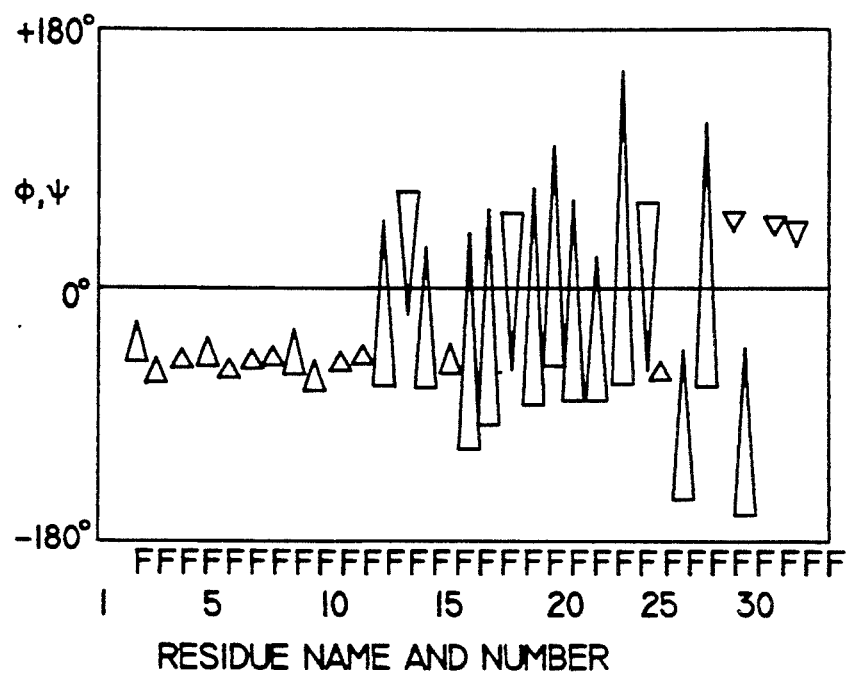
Figure 22:
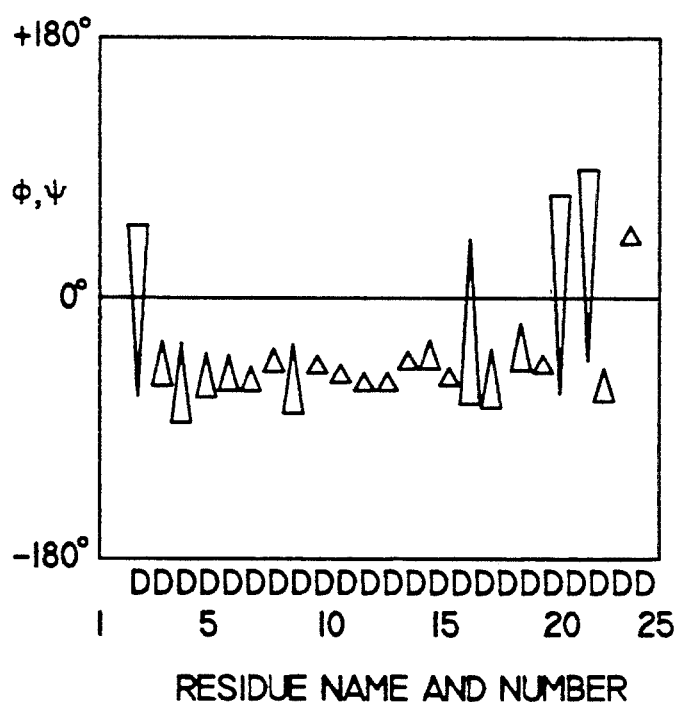

FIG. 19 is a Balaji plot of poly-L-serine;

FIG. 20 is a Balaji plot of poly-L-histidine;

FIG. 21 is a Balaji plot of poly-L-phenylalanine;

FIG. 22 is a Balaji plot of poly-L-aspartic acid; and

FIGS. 23A–23G are a flow chart of a batch computer program used to carry out the ab initio method of the present invention.

DETAILED DESCRIPTION OF THE INVENTION

The following description includes the best mode presently contemplated for carrying out the invention. This description is not to be taken in a limiting sense, but is made merely for the purpose of describing the general principles of the invention. The scope of the invention should be determined with reference to the claims.

At the outset, it should be noted that there are several avenues that can be pursued in the rational design of drugs, and more particularly in the design of peptidomimetic analogs of a target peptide. As used herein, the terms "receptor" and "target" are used to refer generally to compounds that are used as the basis for structure and conformational modeling in accordance with the present invention. The categories of available data useful for designing peptidomimetic drugs may be classified as follows:

(a) the receptor geometry and active conformation of the peptide is known, i.e., the conformation of the target peptide is known when it is bound to the receptor as discovered, e.g., by methods such as X-ray crystallography or NMR (Nuclear Magnetic Resonance);

(b) the receptor geometry is known but the specific bioactive (or binding) conformation of the peptide with respect to the receptor is unknown; and (c) only the sequence of the target peptide is known and the receptor geometry is unknown.

As indicated by the above, varying amounts of information may be available with respect to the peptides contemplated as suitable for manipulation in accordance with the present invention. The amino acid sequences of such peptides can be derived from a variety of sources, e.g., direct sequencing of compounds of known biological activity, application of molecular biology techniques, etc.

Protocols have been established to determine bioactive conformation in each of the three described cases. These protocols have some applicability to the methods of the present invention, and hence will be briefly described. The methods of the present invention are most applicable to cases (b) and (c).

Case (a): When the three dimensional structure of the receptor (e.g., enzyme) and its specific interaction with the target peptide is known, a data base of constrained metabolically stable non-peptide moieties may be used to search for and to suggest suitable analogs for the target peptide. That is, a search may be made of a three dimensional data base for non-peptide (organic) structures (e.g., non-peptide analogs, and/or dipeptide analogs) having three dimensional similarity to the known structure of the target compound. See, e.g., the Cambridge Crystal Structure Data Base, Crystallographic Data Center, Lensfield Road, Cambridge, CB2 1EW, England; and Allen, F. H., et al., *Acta Crystallogr.*, B35: 2331-2339 (1979).

Alternatively, three dimensional structures generated by other means such as molecular mechanics can be consulted. See, e.g., Burkert, et al., *Molecular Mechanics*, American Chemical Society, Washington, D.C. (1982); and Weiner, et al., *J. Am. Chem. Soc.*, 106(3): 765-84 (Eng.) (1984).

It is noted that search algorithms for three dimensional data base comparisons are available in the literature. See, e.g., Cooper, et al., *J. Comput.-Aided Mol. Design*, 3: 253-259 (1989) and references cited therein; Brent, et al., *J. Comput.-Aided Mol. Design*, 2: 311-310 (1988) and references cited therein. Commercial software for such searches is also available from vendors such as Day Light Information Systems, Inc., Irvine, Calif. 92714, and Molecular Design Limited, 2132 Faralton Drive, San Leandro, Calif. 94577. The searching is done in a systematic fashion by simulating or synthesizing analogs having a substitute moiety at every residue level. Preferably, care is taken that replacement of portions of the backbone does not disturb the tertiary structure and that the side chain substitutions are compatible to retain the receptor substrate interactions.

Synthesis and biological evaluation of a series of such compounds ensues in conventional fashion, and iterative refinement of the peptidomimetic (in the case of a constrained analog itself) can then be carried out.

Case (b): If the receptor geometry is known, e.g., from X-ray crystallography or by homology model building, but the manner in which the target peptide interacts with the receptor is not known, the modeling of the peptide may be carried out in the environment of the binding site of the receptor, and the bioactive or binding conformation of the peptide thereby identified. This can be further substantiated by designing chemically modified analogs of this initial binding conformation obtained using steps as described in Case (a). Advantageously, the ab initio methods of the present invention facilitate this procedure.

Case (c): If the receptor geometry is not known, and only the target oligopeptide sequence is known, the most probable conformations of the oligopeptide are simulated, e.g., by molecular dynamics methods and by searching a data base of constrained peptide analogs. Once the most probable conformations have been identified, they are used to suggest analogs which mimic the probable conformations at every residue.

An evaluation of the biological activity (or binding affinity data—if appropriate) and the use of an iterative approach (including activity and inactivity profiles of rigid or otherwise chemically modified analogs evaluated) is then used to identify the bioactive conformation. This bioactive conformation can then optionally be used to design peptidomimetics, or to search a three dimensional data base of organic structures to suggest potential peptidomimetics. In this case also, the ab initio technique of the invention is particularly useful, as are the conformation energy maps and Balaji plots described herein.

Rational Drug Design—An Overview

Figure 1:
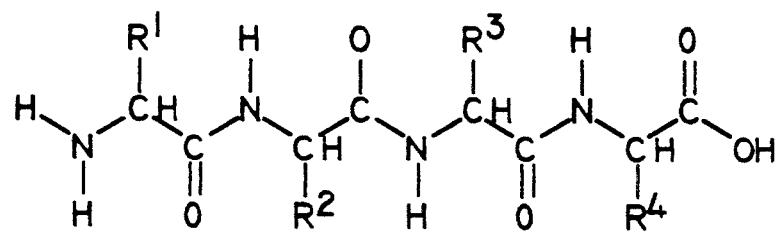
FIGS. 1, 2A, 2B, 2C, 3A, 3B and 3C were described above in connection with the "Background of the Invention" portion of the application, wherein they were used to help describe and define various features, parameters, structures and characteristics of peptides and polypeptide chains. More particularly.
Figure 2A:
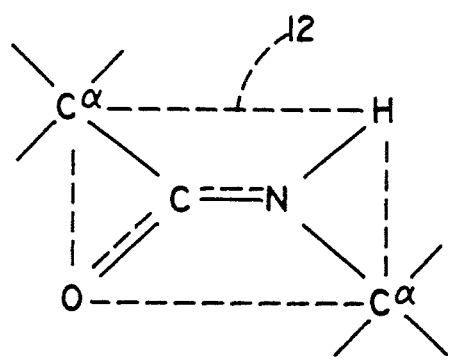
Figure 2B:
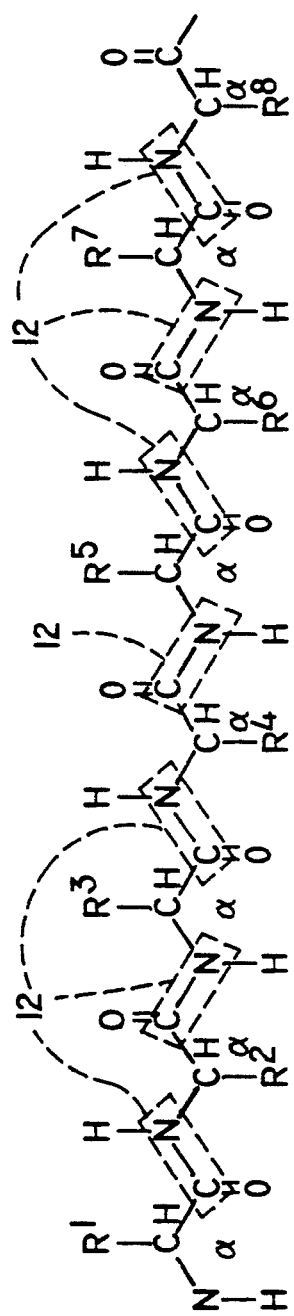
Figure 2C:
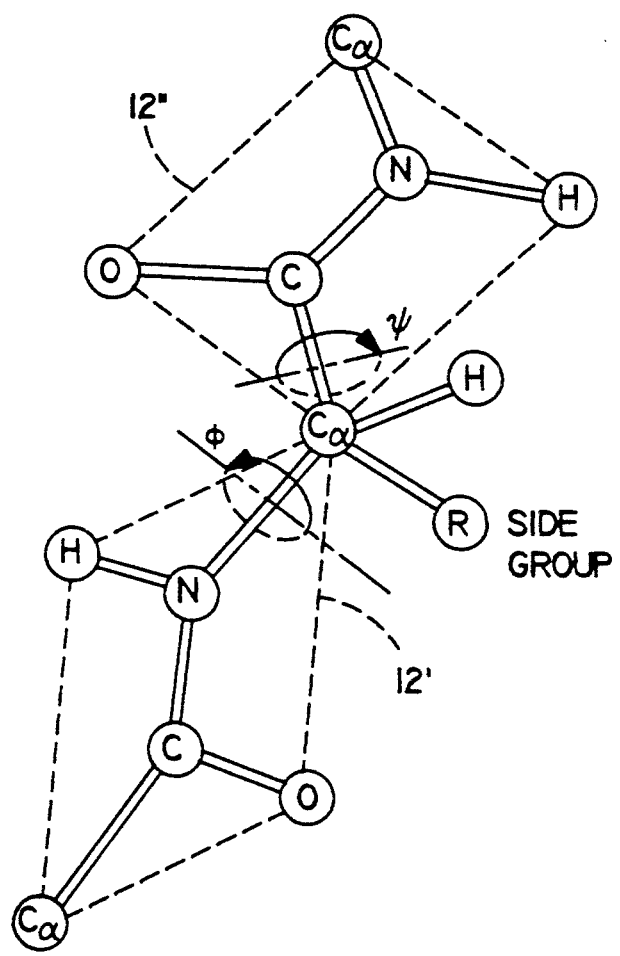
Figure 3A:
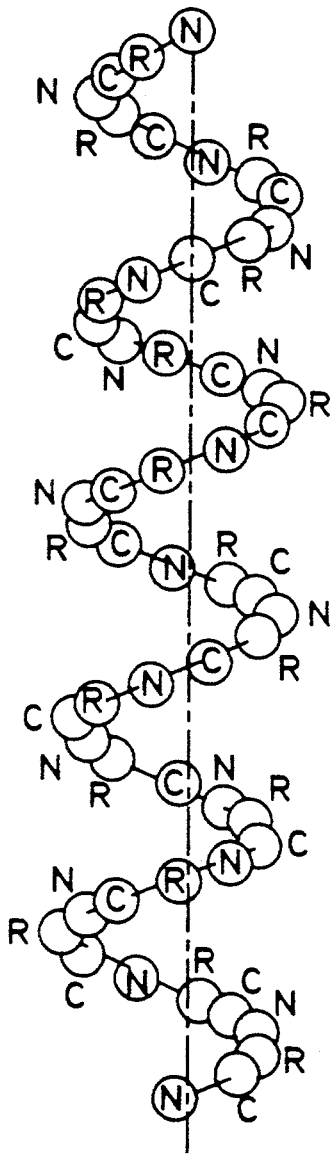
Figure 3B:
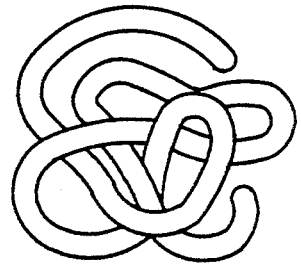
Figure 3C:
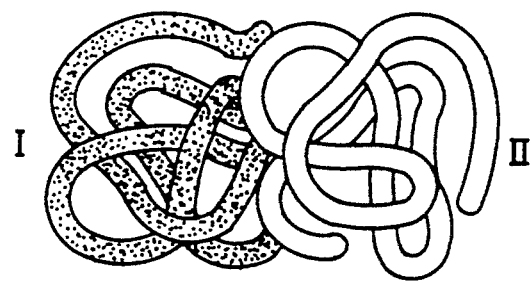
Figure 4:
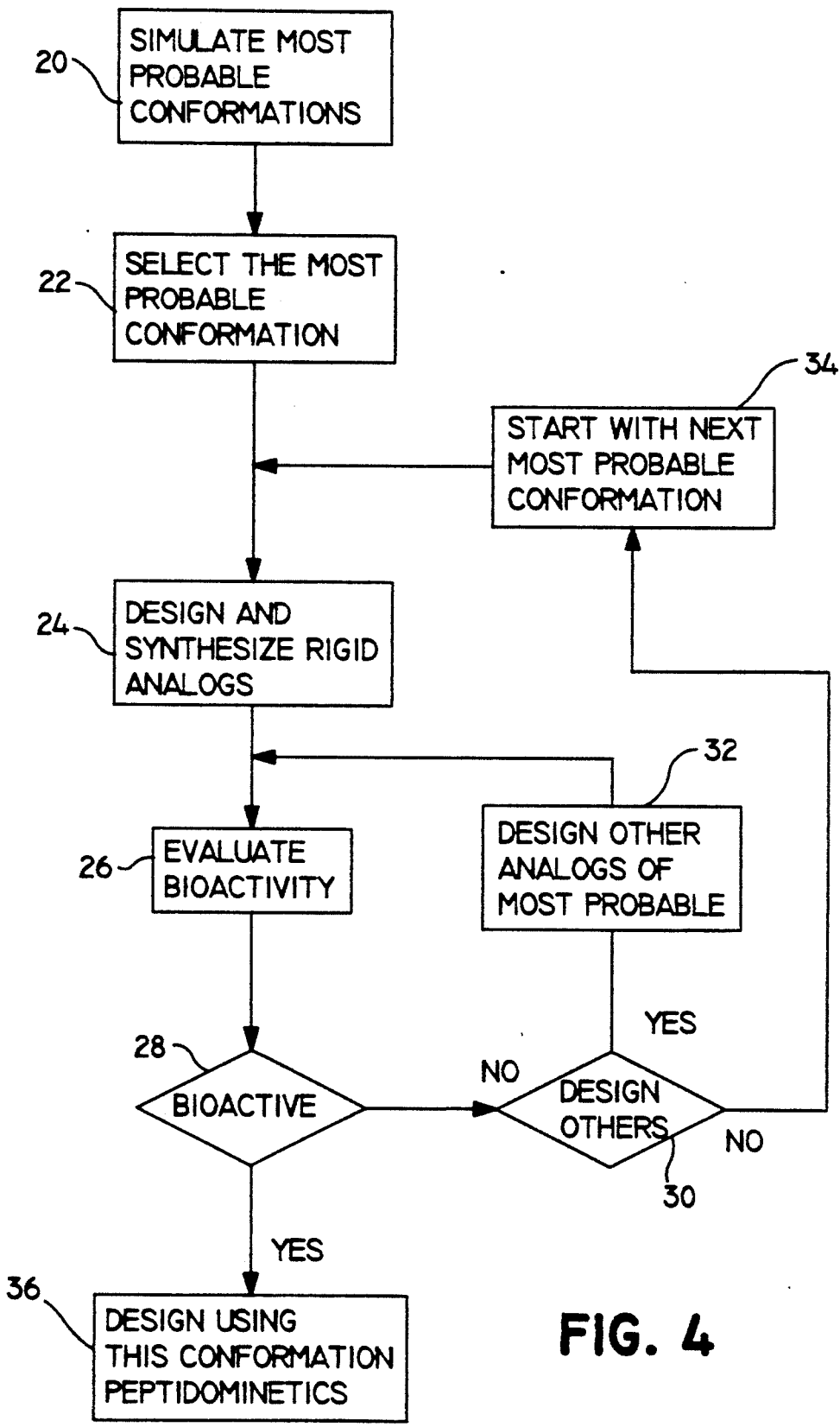
FIG. 4 is a flow chart of the rational drug design method of the present invention.

Referring to FIG. 4, a flow chart provides an overview of the main steps of the rational drug design method of the present invention. Each step or process included in the flow chart is briefly described in a "box" or "block" of the flow chart. Reference is hereafter made to a particular block of the flow chart by the reference numeral attached thereto.

As shown in FIG. 4, the overall method of the present invention involves the following steps:
  (a) simulating the most probable conformations of a given polypeptide (block 20);
  (b) selecting the most probable conformation of the peptides thus simulated (block 22);
  (c) designing and synthesizing a chemically modified analog of the selected peptide (block 24);
  (d) evaluating the bioactivity of the synthesized chemically modified analog of the selected peptide (blocks 26 and 28); and thereafter, optionally
  (e) designing a suitable peptidomimetic based on the conformation of the synthesized chemically modified analog of the selected peptide (block 36).

It is noted that in carrying out step (d), a suitable peptidomimetic may be identified, and hence there may be no need to carry out step (e). However, even if step (d) does not yield a suitable peptidomimetic, the results of step (d) may nonetheless provide useful data for beginning step (e), or for other purposes. Hence, step (e) above should be considered as an optional step that may be performed as part of the drug design method herein disclosed, but not an essential step.

In carrying out the method shown in FIG. 4, it is noted that if the chemically modified analog of the selected peptide is not bioactive (block 28), as determined through suitable testing, then an additional step (block 30) relates to determining whether other chemically modified analogs should be designed for this same selected peptide. If so, then another chemically modified analog for the selected peptide is designed (block 32), and the bioactivity of this newly designed chemically modified analog is evaluated (block 26). If a determination is made that another chemically modified analog for this same peptide should not be designed, then the next most probable conformation of the simulated peptide is selected (block 34), and a chemically modified analog is designed and synthesized for such selected peptide (block 24), and the process is repeated.

A more detailed description of each of the steps set forth in the flow diagram of FIG. 4 will next be presented.

Simulating Most probable Conformations

The first step of the overall method (block 20 in FIG. 4) is simulating the most probable conformations of a given polypeptide. The preferred manner for accomplishing this step is to utilize the ab initio process previously referenced. This ab initio process involves (a) simulating a real-size primary structure of a polypeptide in a solvent box (e.g., in an aqueous environment as defined below); (b) shrinking the size of the peptide isobarically and isothermally; and (c) expanding the peptide to and beyond its real size in selected time periods, while measuring the energy state and coordinates, e.g., the $\phi$, $\psi$ angles, of the expanding molecule(s).

The shrinking and expanding of the simulated peptide is, of course, also simulated using a suitable computer. Simulation occurs by specifying the chemical and physical parameters of the peptide chain for use by the computer simulation program. Such parameters include a definition of the particular atoms and/or groups of atoms present in each residue of the peptide chain. Physical data associated with each atom and/or group of atoms, e.g., including bond lengths and electrical forces associated with the particular atom and/or molecule, are well documented in the literature. See, e.g., Weiner, et al., in *J. Comput. Chem.* 7: 230-252 (1986), and Weiner, et al., in *J. Am. Chem. Soc.* 106: 765-784 (1984).

Preferably, the simulation data are organized by each amino acid residue of the peptide chain. As there are only a limited number of amino acids that may appear in a naturally occurring peptide chain (i.e., twenty), the initial data entry into the computer for the calculation of naturally occurring peptide chains is greatly simplified. That is, a data set for each possible amino acid residue is collected and stored for ready retrieval into the simulation program. A representative amino acid data set is shown in Table C-1. Data sets for all of the naturally occurring amino acids, as well as D-amino acids, synthetic amino acids (e.g., Aib), and the like, are included in the Microfiche Appendix. Initial data entry into the computer simulation program thus requires specification of the number of residues in the primary peptide structure, and then specifying the particular amino acid represented by each residue. The simulation program then retrieves the appropriate data set for the specified residue and enters the requisite parameters of that residue into the program.

The data set for each amino acid may include the values of the $\phi$, $\psi$ angles that orient the amide planes of each residue relative to the $C^\alpha$ atom of the residue. If chemical/physical data is known for these angles, such known data can be used so that the simulation starts out with a conformation that is near an expected conformation. Advantageously, however, if such data is not known, the $\phi$, $\psi$ angles may simply be set to an arbitrary value, e.g., zero. Hence, an advantageous feature of the ab initio simulation method of the invention is that it requires no assumptions relative to a particular conformation.

Chemical/physical data associated with any pendant groups (or side chains) of the peptide are also entered into the simulation program in a similar manner. Because the pendant groups, if any, may take numerous forms, the data set used is typically somewhat more comprehensive than the data sets used solely for the amino acid residues of the backbone of the peptide of interest. However, the pendant group data may be expanded systematically, building upon known data, atom by atom, as required for a particular simulation.

Before or after the data for the primary structure of the simulated peptide is entered into the simulation program, similar data is also entered that specifies the background, or environment, in which the peptide is being simulated. This environment is preferably an aqueous environment, e.g., $H_2O$, or other solvent. Because such background data remains the same throughout the simulation, such data need only be entered once.

With the background solvent and peptide chain thus defined, the simulation program allows the various molecules present in the chain to interact with each other in accordance with the normal electrical and/or molecular forces present within such molecules. The normal interaction between the molecules takes place in accordance with well defined "molecular mechanics" forces defined by known energy equations. Molecular mechanics simulation packages are known in the art. An example of a molecular mechanics package that may be used with the present invention is the CONCORD program available from Evans and Sutherland Computer Corporation, Salt Lake City, Utah. See also, Karplus, M. "Molecular Dynamics: applications to Proteins" in computer Simulation of chemical and Bimolecular Systems, (Bevendge and Jorfensen, Eds.) *Annals of the New York Acad. Science*, Vol. 482, pp 255-266 (1986); Weiner, et al., "A New Force Field for Molecular Mechanical Simulation of Nucleic Acids and Proteins", *J. Am. Chem. Soc.*, Vol. 106(3), pp. 765-784 (1984).

In accordance with such simulation packages, or equivalent (and it is recognized that those skilled in the art could prepare their own equivalent molecular mechanics simulation packages), each ion, atom and molecule has a known electrical charge associated therewith. Some of the charges cause the atoms or ions to be attracted to each other, some cause the atoms or ions to be repelled from each other. The bond lengths between the various ions, atoms and molecules of each residue are defined. In the case of a peptide chain, these molecules are arranged in relatively rigid amide planes that are joined to $C^\alpha$ atoms at "swivel points", as previously described. Thus, in response to the various attraction and repulsion forces set up by the particular ions, atoms and molecules present, the simulated peptide chain bends and flexes at the swivel points, seeking a stable conformation.

Figure 5A:
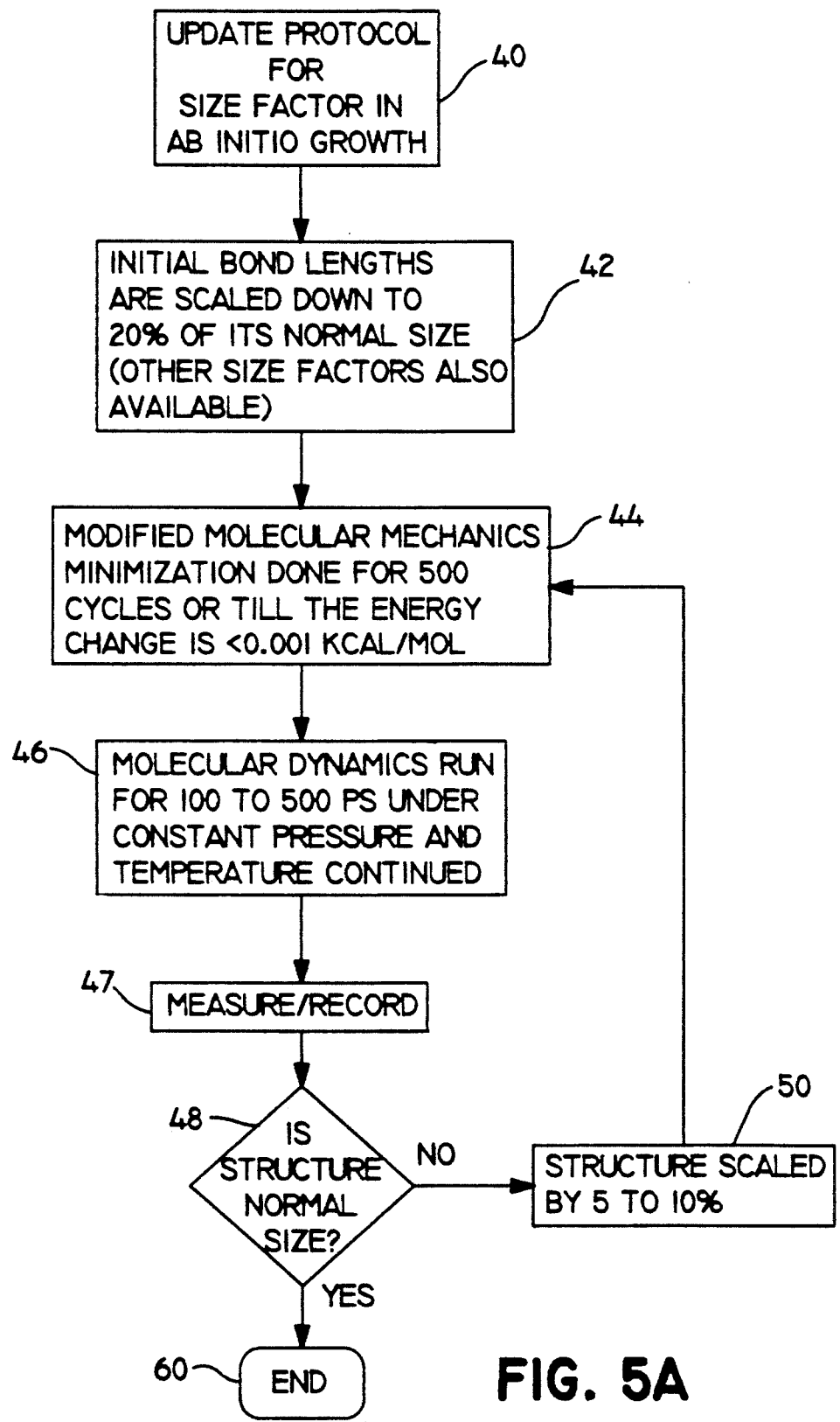
FIGS. 5A, 5B, and 5C are flow charts providing additional details relative to the ab initio simulation process of the invention.

To assure that the most probable conformation is identified during this ab initio simulation process, a shrinking and growing process is invoked as shown in the flow chart of FIG. 5A. In accordance with this shrinking and growing process, additional parameters are selectively defined to specify a desired protocol for the process (block 40 of FIG. 5A). Once these additional parameters are specified, the initial bond lengths (i.e., those included in the respective amino acid data sets) are scaled down to a specified size factor, or percentage of their normal size (block 42 of FIG. 5A). This specified size factor is set by the particular protocol selected (block 40). A preferred size factor is 20% (as indicated in the flow chart at block 42), although other size factors could also be used, e.g., 10%, 15%, 25% or 30%, or any other value, as desired.

It is noted that only the bond lengths of the atoms in the peptide chain backbone are scaled down by the specified size factor. The bond lengths associated with the background solvent remain at their normal size.

With the bond lengths reduced to the specified size factor, a "modified molecular mechanics" simulation is invoked (block 44 of FIG. 5A). This modified molecular mechanics simulation is the same as the conventional molecular mechanics simulation, except that it occurs with the scaled down bond lengths. Hence, because the bond lengths are initially shorter, the interactive molecular forces between the various charged species and atoms in the peptide chain are significantly different than they would be with full size bond lengths.

It is further noted that the scaling down of the bond lengths is carried out both isobarically and isothermally. That is, with the scaling down of the bond lengths, the ambient pressure and temperature values used while performing the molecular mechanics simulation are also scaled down accordingly.

The computer performing the molecular mechanics simulation operates in accordance with programmed cycles. In a first cycle, which involves a prescribed number of computer clock cycles in order to complete a prescribed number of calculations (and hence requires a certain amount of computer time to complete), the molecular forces associated with the then current position of the peptide molecules are computed. These forces interact with the molecule in accordance with known dynamics to begin to move or change the current position of the molecules to a new position. In a second cycle, the same calculations are recomputed in order to determine the forces associated with the new position of the peptide molecules based on their new position, which forces interact to move the molecules to yet a newer position. As indicated at block 44 of FIG. 5A, this process continues for 500 cycles or until the energy change between cycles is less than 0.001 Kcal/mol. (An energy change between cycles of less than 0.001 Kcal/mol is considered as an indication that a stable position of the molecules has been reached.)

The simulated molecules remain at the scaled down size for a prescribed period of time (simulation time), as indicated in block 46 of the flow chart of FIG. 5A. During this simulation period, which may be from 100 to 500 picoseconds, the molecule undergoes whatever changes in conformation result from the modified molecular mechanics simulation during the prescribed period of time. At the conclusion of this time, values of key parameters of the simulated peptide residues, e.g., the $\phi$, $\psi$ angles may be recorded or otherwise noted (block 47).

Further, at the conclusion of the 100 to 500 picoseconds of simulation time, a determination is made as to whether the structure is at normal size (block 48). If not, the structure is scaled up by 5 to 10% (block 50), and the modified molecular mechanics simulation repeats (block 44). If the structure is determined to be of normal size, then the ab initio growth process is terminated (block 60). When terminated, the growth parameters associated with the process, principally the final $\phi$, $\psi$ angles, are recorded and are available for use during the next step of the drug design method.

Figure 5B:
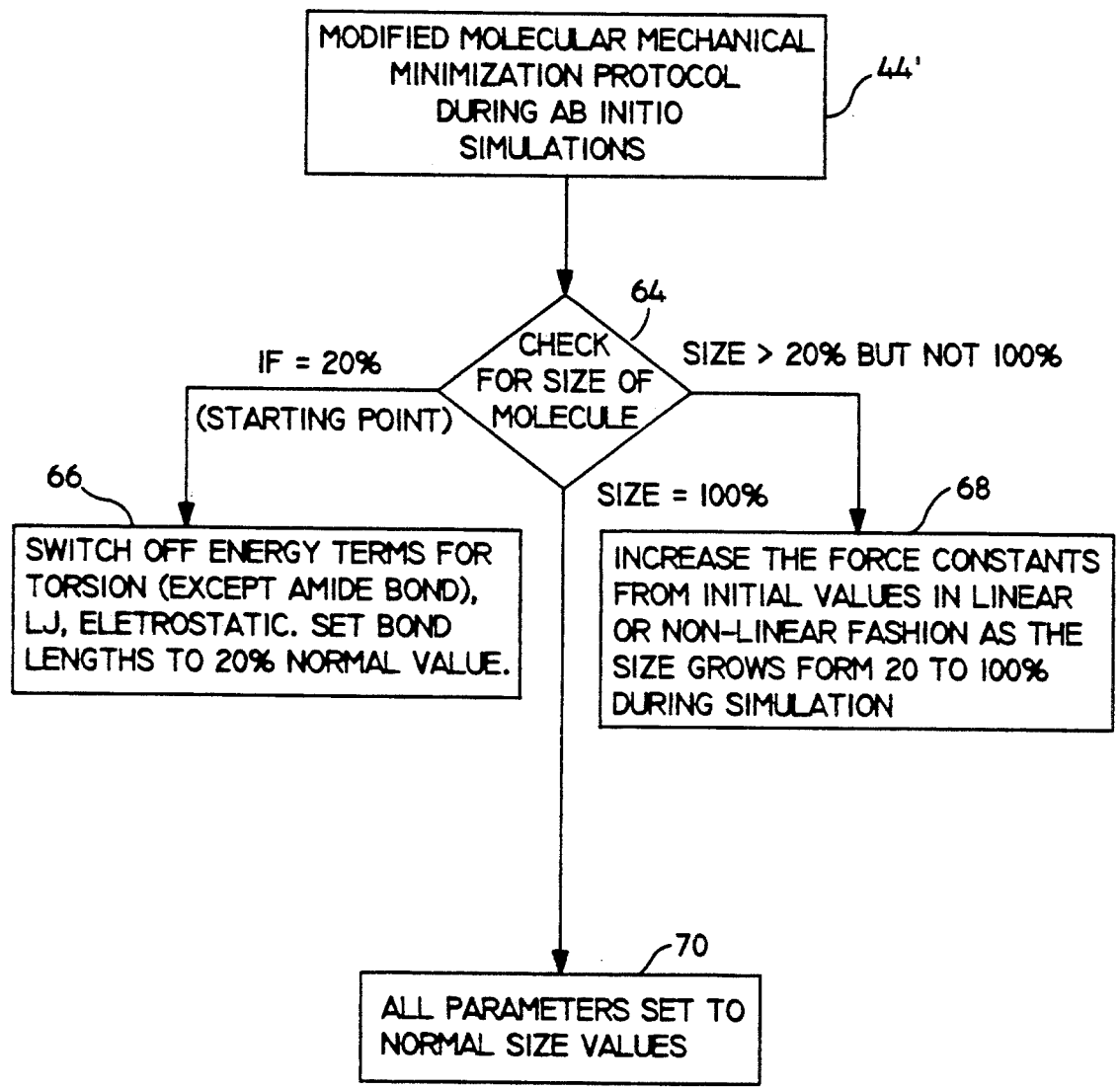

Referring next to FIG. 5B, a chart is shown providing further details relative to the modified molecular mechanics simulation (performed at block 44 of FIG. 5A) of the ab initio simulation method. As indicated in FIG. 5B, there are three protocols that may be used during modified molecular mechanics. The particular protocol used is governed by the size of the molecule. Hence, while performing modified molecular mechanical simulation (block 44' in FIG. 5B), a determination is made as to the size of the simulated molecule (block 64). If the size is the initial scaled size to which the molecule has been shrunk, e.g., 20% of its normal size (or other selected starting size), selected energy terms in the molecular model are turned off, thereby providing the model greater ability to move and change its conformation. These "switched off" energy terms include the electrostatic charge; torsional parameters, except for the amide bond (i.e., the simulated model maintains the rigidity of the amide plane); and the Lennard Jones (LJ) repulsive and attractive force constants (block 66). Thus, the only energy terms remaining at this initial stage are those associated with the amide plane and bonds.

If the size of the simulated molecule (block 64) is somewhere between its initial value (e.g., 20%) but not yet equal to 100% of its normal size, the force constants associated with the energy terms used in the simulation are increased from their initial values (which may be zero), either in linear or non-linear fashion, as the size of the simulated molecule grows from its starting size to its normal size (block 68).

If the size of the simulated molecule (block 64) is equal to its normal size, i.e., 100%, then all parameters are set to normal size values (block 70).

For some applications, it may be desirable to continue growing the simulated peptide beyond its normal size, e.g., to 110% of its normal structure size. This allows additional data to be gathered that provides further insight into the propensity of the expanding peptide chain to seek a stable conformation.

As previously indicated, as the peptide expands to its full size and beyond, it assumes a stable tertiary structure. In most cases, due to the manner in which the expansion occurs, this tertiary structure is either the most probable structure (i.e., represents a global minimum for the structure), or, in the case where there are more than one relatively stable local minima, one of the most probable structures. As desired or required, repetition of the ab initio technique and/or further analysis of the tertiary structure thus obtained, e.g., using conformational energy maps and/or the Balaji plots referenced below, provides a further measure of the probability of occurrence of the structure.

There are also three protocols associated with the manner in which the shrinking and growing of the simulated molecule of the ab initio method may be practiced. In a first protocol, the residues of the peptide chain are shrunk and then expanded one at a time. That is, the first residue of the chain is placed in the solvent box, shrunk and expanded by itself. When only a single residue is present, there will be little interaction with other molecules as the simulated expansion occurs, because there are no other atoms present except for the surrounding solvent. However, some interactions will occur within the residue and the background solvent that may slightly affect the $\phi$, $\psi$ angles, thereby providing some data. The second residue of the chain is then placed in the solvent box, coupled to the first residue, shrunk and expanded while the first residue remains at its normal size. This process is repeated for the third residue of the peptide chain, and so on, through all of the residues, with each newly added residue to the chain being shrunk by itself (without shrinking the prior residues), and then growing by itself in the environment of the background and prior residues at normal size.

Figure 5C:
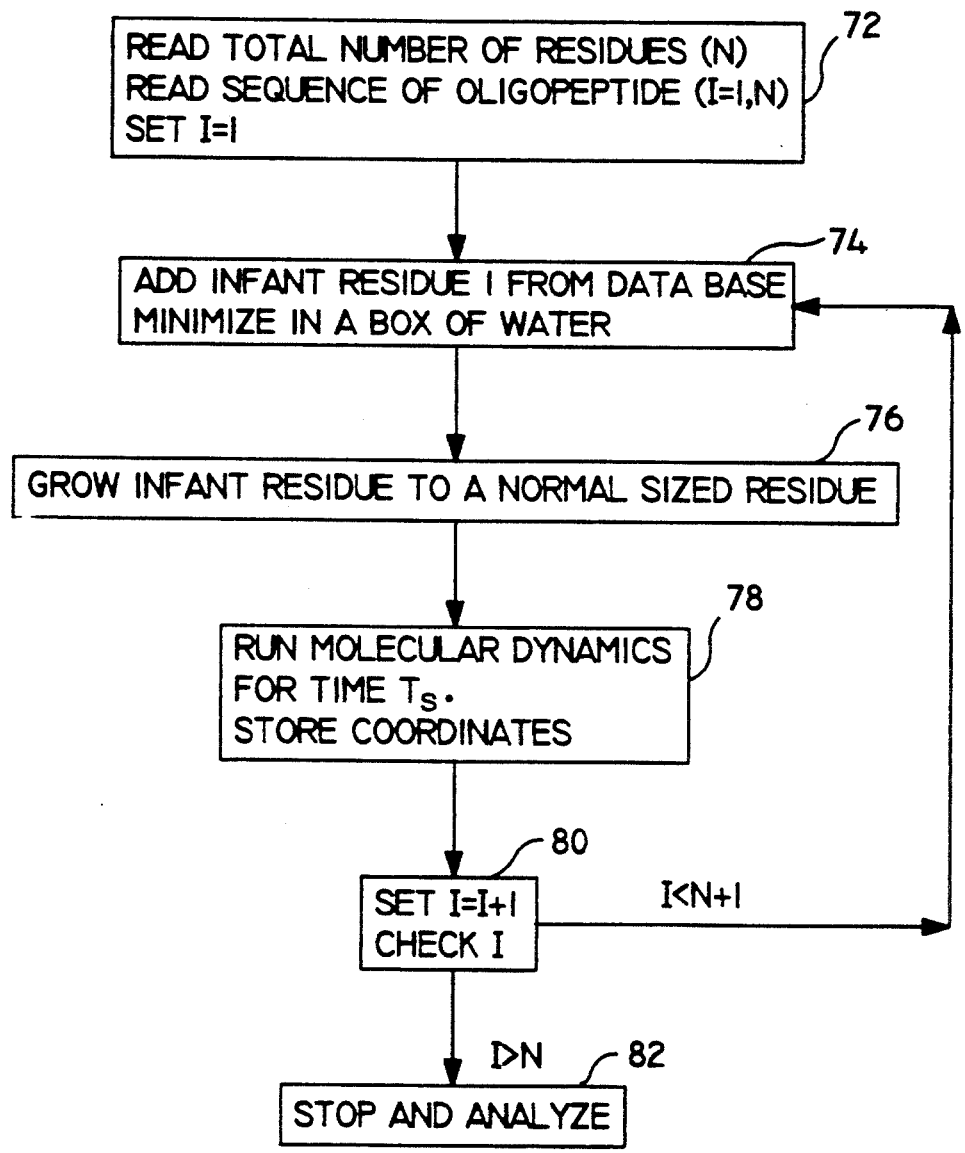

A flow chart for this first protocol of the ab initio process is illustrated in FIG. 5C. As seen in FIG. 5C, a first step involves setting the initial parameters and gathering the necessary data (block 72) required to perform the simulation. This data is obtained by reading the total number of residues (N) in the peptide chain that is to be simulated, and by also reading the sequence of the peptide chain. Each residue of the sequence is identified by an indicator, "I". Thus reading the peptide sequence involves reading the data associated with the first residue, $I=1$, reading the data for the second residue $I=2$, and so on up to the Nth residue, $I=N$. The simulation starts by setting $I=1$.

With $I=1$, the data associated with such residue is obtained from the residue data base, and shrunk to its starting size, e.g., 20% of its normal size, and placed in a water box (block 74). The size of the water box is chosen to provide a solution of water (the background solvent) with at least about 11 Å shell of water on each side of the residue placed therein. The system energy is then minimized with periodic boundary conditions with constant dielectric constant $\epsilon = 1$. This shrinking is performed as previously described in connection with block 66 of FIG. 5B. The infant (small) molecule for the first residue is then grown or expanded to its normal size (block 76), as also previously described, e.g., in connection with block 68 of FIG. 5B or blocks 44–50 of FIG. 5A. Once the normal size of the molecule has been obtained, the molecular dynamics is continued, i.e., the energy equations remain in force for a prescribed period of time, $T_s$ (block 78). Typically, this time $T_s$ is of the order of 50 picoseconds (simulation time), but may be selected to fall within the range of 0.1 to 10,000 picoseconds. The coordinates of the resulting molecule are stored after a prescribed simulation time period, e.g., after each 0.1 picosecond, as also indicated in block 78.

After this process has been performed for the first residue, $I=1$, the value of I is incremented to specify the next residue of the chain, i.e., the value of I is set to $I=I+1$, as shown in block 80 of FIG. 5C. The new value of I is then checked to see if it is equal to $N+1$, where N is the number of residues in the peptide chain, as also indicated in block 80. If this new value of I is less than $N+1$, then the residue associated with the new value of I is retrieved from the residue data base, coupled to the previous residue, and shrunk to its initial size in the solvent box. The process is then repeated for this new residue as previously described above in connection with blocks 74, 76, 78 and 80. If the new value of I set in block 80 is equal to $N+1$, then the ab initio process is stopped, and the results are analyzed (block 82).

In a second protocol of the ab initio process, the entire peptide chain is modeled in the solvent box, with each residue of the chain being shrunk, and expanded simultaneously. The calculations performed during the simulation using the second protocol are the same as those used in the first protocol, but there are a larger number of such calculations to perform.

In a third protocol of the ab initio process, known physical and/or chemical data, if any, is used to bias the simulation towards a known result. Thus, in accordance with this third protocol, when the initial data for a particular peptide being simulated is retrieved from the residue data base, the data is set to known chemical or physical data. In some instances, the known chemical or physical data allows the shrinking and expanding steps to be by-passed, because the conformation of the molecule is well defined by the known data. In other instances, the known chemical and physical data is used to bias the starting point of the infant (shrunk) molecule as it begins to grow.

The energy equations used to perform the molecular mechanics simulation during the ab initio process are based on the potential energy of the simulated molecule. The potential energy function of a molecule is a function of its atomic coordinates and is represented as $V(r)$.

In the dynamical simulation, the function $V(r)$ is represented as:

$$V(r) = \sum_{i=1}^{N_b} 0.5 K_{bi}(b_i - b_{i0})^2 + \sum_{i=1}^{N_\theta} 0.5 K_{\theta i}(\theta_i - \theta_{i0})^2 +$$

$$\sum_{i=1}^{N_\phi} 0.5 K_{\phi i}(1 + \cos(n\phi_i - \nu_{ri})) +$$

$$\sum_{i,j=1; i>j; i\neq j}^{N} \left[ \left( \frac{A_{ij}}{r_{ij}^{12}} \right) - \left( \frac{B_{ij}}{r_{ij}^{6}} \right) \right] +$$

$$\sum_{i,j=1; i>j; i\neq j}^{N} \left[ \frac{q_i q_j}{\epsilon r_{ij}} \right]$$

where:
$K_{bi}$ is the bond stretching force constant, $b_i$ is the $i^{th}$ bond length, $b_{i0}$ is the equilibrium bond length, and $N_b$ is the total number of bonds.

$K_{\theta i}$ is the bond angle bending force constant $\theta_i$ is the $i^{th}$ bond angle, $\theta_{i0}$ is the equilibrium bond angle for the ith bond angle, $N_\theta$ is the total number of bond angles.

$K_{\phi i}$ is the dihedral angle force constant, $\phi_i$ is the $i^{th}$ dihedral angle, $\nu_{ri}$ is the phase factor for the $i^{th}$ dihedral angle, n is the fold of the $i^{th}$ dihedral angle potential, and $N_\phi$ is the total number of dihedral angles.

$A_{ij}$ is the Lennard Jones repulsive force constant for the $(ij)^{th}$ pair of atoms, $B_{ij}$ is the Lennard Jones attractive force constant for the $(i,j)^{th}$ pair of atoms, $r_{ij}$ is the distance between $i^{th}$ and $j^{th}$ atoms and N is the total number of atoms.

$q_i$ is the partial charge on the $i^{th}$ atom, $q_j$ is the partial charge on the $j^{th}$ atom, and $\epsilon$ is the dielectric constant.

With the above energy equations defined, it is noted that the ab initio process utilizes a "starting geometry" that is a specified percentage of the physically observed or "normal geometry". During the growth process of the first protocol, the starting parameters for the bond terms in the potential energy equations are defined as follows:

$K_{bi}$ is the same as the normal size function; $b_{i0}$ is about 20% of the normal value.

The starting parameters for the angle bending terms in the potential function are defined as follows: $K_{\theta i}$ is the same as the normal size function; $\theta_{i0}$ is the same as the normal size function.

The starting parameters in the dihedral terms in the potential functions are as follows: $K_{\theta i}$ is set to zero except for the backbone amide bond ($\omega$) which designates the dihedral angle of the peptide bond defined by atoms $C^\alpha$—C—N—$C^\alpha$. The values of n and $v_n$ are set to their normal values for all the cases.

The starting parameters for the electrostatic term $q_i$ and $q_j$ are set to zero.

As the molecule is grown from the starting size, namely, from "20% size" to "full 100% size", the parameters in the potential functions are updated continuously at every dynamical step in a linear fashion. If desired, they can also be updated in any non-linear fashion.

The form of updating can be, in general, a linear or non-linear function. The starting geometry can also be anything from close to zero to 100%.

In the case of full growth (simultaneous swelling of the molecule, as used for the second protocol of the ab initio process), the dynamical procedure is preferably done over a period of 2 nanoseconds of simulation time for a typical molecule the size of 20 amino acid residues.

In the case of sequential growth (first protocol), the run is done over a period of 50 picoseconds per amino acid addition.

It is to be understood that these values are illustrative only. The invention includes the application of these methods to other simulation time frames and residue lengths. For example, sequential growth could be performed over periods ranging from 1 to >100 picoseconds per amino acid addition. Similarly, simultaneous growth could be done over periods of >0 to 1 nanosecond for a typical sized molecule containing 20 amino acids.

A description of the key computer programs utilized in carrying out the best mode of the ab initio process is set forth below. Actual program listings for many of the computer programs are included in the Microfiche Appendix filed herewith. In general, such listings are written in Fortran, or other well known languages, are well documented with comments, and are readily understandable to those skilled in the art. Routine portions of the ab initio process carried out by the computer, e.g., data handling, coordinate conversion, known molecular dynamics, etc., that are well known in the art. are not set forth herein or in the Microfiche appendix.

As previously indicated, in some instances of drug design the receptor geometry is known, e.g., from X-ray crystallography or by homology model building. The manner in which the target peptide interacts with the receptor, however, is not known. In these instances, the ab initio process of the present invention may advantageously be used to model the peptide constrained to be in the environment of the binding site of the receptor. As the peptide is grown or expanded constrained by the environment of the binding site of the receptor in accordance with the ab initio process, the bioactive or binding conformation is more readily identified and understood. Rigid or otherwise chemically modified analogs may then be designed, as required, to confirm this initial binding conformation.

The Simulation System Hardware

Figure 6:
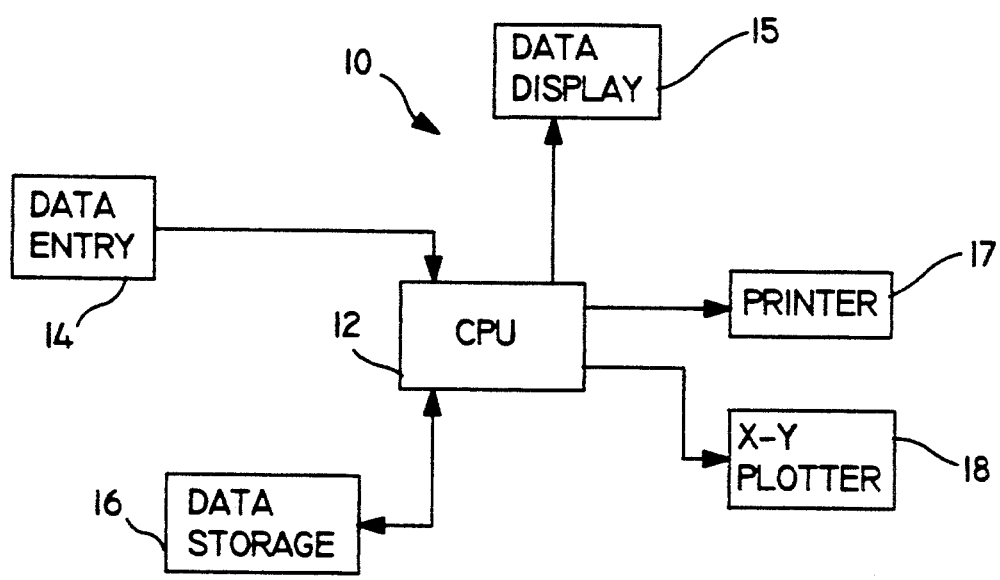
FIG. 6 is a block diagram of a processing system used to carry out the simulation methods and techniques of the present invention.

FIG. 6 shows a simplified block diagram of a processing system 10 of the type used to carry out the ab initio simulation methods and other processing techniques of the present invention. The system 10 is centered around a suitable central processing unit (CPU) 12. Coupled to the CPU 12 is a data entry subsystem 14, which may include a keyboard or other conventional data entry devices. Also coupled to the CPU 12 is a data storage subsystem 16. The data storage subsystem 14 preferably includes non-volatile memory elements, allowing data sets and operating programs to be permanently stored, e.g., on magnetic or optical disk media, magnetic tape media, read only memory (ROM), or programmable read only memory (PROM), for ready retrieval when needed. The memory subsystem 16 further includes volatile memory storage elements, e.g., random access memory (RAM), for holding the particular operating programs and data sets being used at a particular time. A data display subsystem 15, such as a conventional monitor and/or flat screen LCD display, is likewise coupled to the CPU 12, and allows entered data, processed data, and other information to be displayed for use by an operator. A printer subsystem 17 and an X-Y plotter 18 may also be coupled to the CPU 12, and provide a convenient means for making a hard copy of the data or other information generated by the simulation program. This data includes, e.g., automatic generation of the Balaji plots and energy conformation maps, described below.

As will be evident to those skilled in the computer and simulation arts, all of the elements shown in FIG. 6 may be realized using commercially available computer equipment. Due to the nature of the data processing involved in performing a simulation of a peptide in an aqueous environment as described above (i.e., entering a data base that characterizes each of the residues and pendant groups that are used in the simulation, shrinking the peptide, expanding the peptide, recording and calculating conformation parameters at key points during the simulation, etc.), the amount of data and processing utilized in the ab initio method are not insignificant. While any suitable computer can be programmed for this purpose, including a personal computer having sufficient memory, and preferably a math coprocessor board, such processing is carried out much more efficiently (i.e., using less computer time) when performed using a supercomputer.

A supercomputer is a computer characterized by its large memory capacity and its ability to carry out many computations in parallel (i.e., it utilizes many processors operated in parallel so that several computations may be carried out simultaneously during the same computer clock cycle). A supercomputer is further characterized by utilizing a "wide" operating code, e.g., 64 bits, thereby significantly increasing the amount of information that can be handled during each computer clock cycle. A typical supercomputer has a RAM memory capacity associated therewith on the order of 4–8 MWords, where 8 bytes is equal to one "Word", and "M" signifies one million. (Thus, a memory capacity of 4–8 MWords is equivalent to 32–64 Megabytes.) Of course, much more memory is available using external non-volatile memory, such as a high performance hard disk drive, which disk drive may be either magnetic and/or optical. Several models of supercomputers are commercially available, such as from Cray Research Incorporated, of Chippewa Falls, Wis., or Convex Computer Corporation, of Richardson, Tex. The basic structure of the Cray supercomputer is described in U.S. Pat. No. 4,128,880, which patent is incorporated herein by reference.

Selecting the Post Probable Peptide Conformation from Those Simulated

The second step of the overall rational drug design method of the present invention, as indicated at block 22 of FIG. 4, relates to selecting the most probable conformation of the peptides that have been simulated by the ab initio process. In some respects, this second step may be considered as merely an extension of the first step of simulating the most probable peptide conformations (block 20), i.e., the first and second steps may be considered as a single step of "simulating and selecting" the most probable peptide conformations. This is particularly the case where the ab initio process, as described above, is used because such process inherently points the simulated peptide to a stable conformation. Thus, at the conclusion of the ab initio simulation, the most probable peptide conformation may already have been selected. However, in many instances, carrying out the ab initio simulation step will result in several peptide conformations, e.g., a family of simulated peptides, each of which is stable to differing degrees. In such an instance, a selection process will be required to ascertain which of the simulated peptides presents the most stable conformation. It is this selection process that is next described.

Figure 7A:
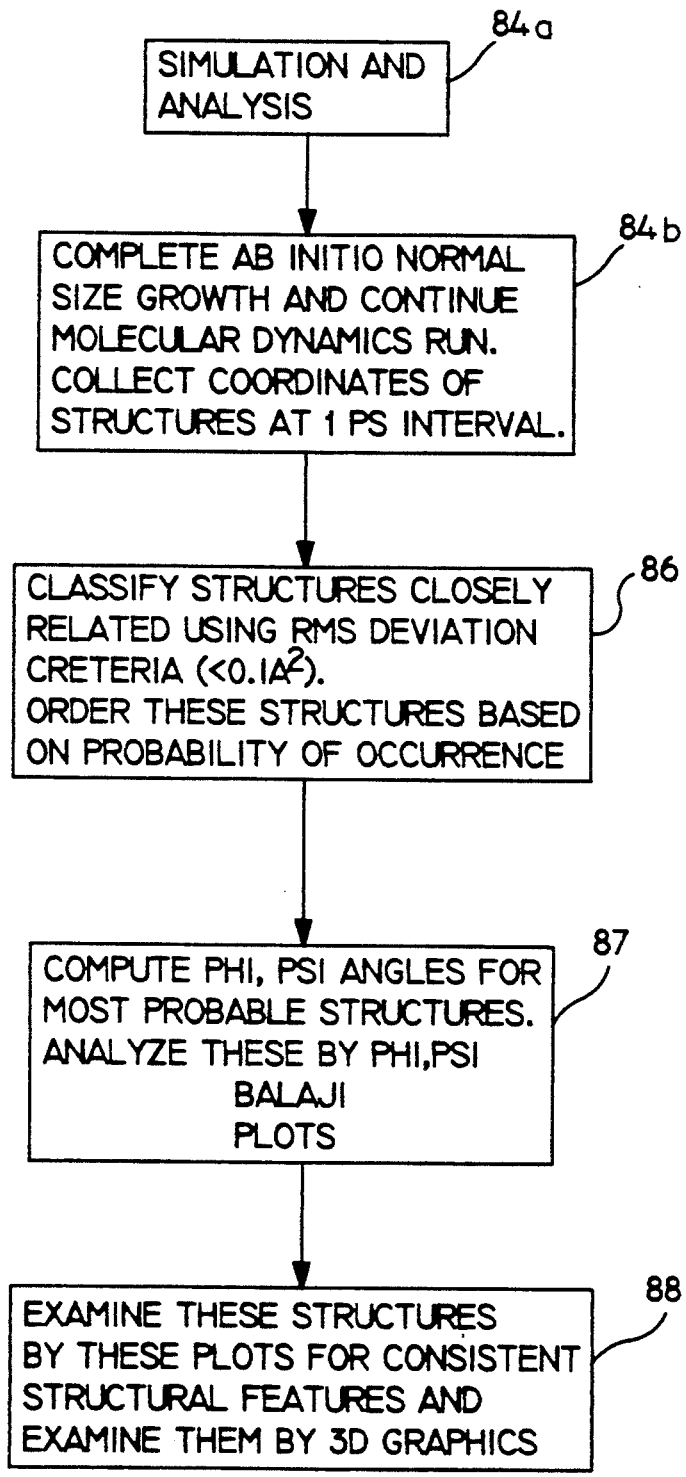
FIG. 7A is a flow chart illustrating a preferred method for selecting the most probable conformation for a tertiary structure.

An overview of this selection process is illustrated in the flow diagram of FIG. 7A. It is noted that the first two blocks in FIG. 7A (blocks 84a and 84b), relate to the ab initio simulation process previously described in connection with FIGS. 5A–5C. While the ab initio process represents the preferred method for performing the peptide simulation, it is to be understood that other simulation methods could also be employed. Regardless of the simulation method used, the present invention recognizes that some systematic and rational method should desirably be used to analyze the simulation data to ascertain the most probable conformation(s). In accordance with the present invention, this selection process is preferably accomplished by:

(a) classifying the simulated structures using a suitable classification technique, such as an rms deviation criteria of the mean geometries of the structures;

(b) ordering these classified structures based on probability; and (c) analyzing the ordered structures to confirm that the most probable conformations have in fact been selected.

The steps of classifying (step (a) above) and ordering (step (b) above) the structures (block 86 of FIG. 7A) are performed using classical techniques known in the art. The step of analyzing the ordered structure (step (c) above) to confirm if it is the most probable structure is more subtle. This analytical step includes many of the same investigations and considerations involved in designing and synthesizing rigid or otherwise chemically modified analogs of the simulated peptides (the third step of the overall drug design method, block 24 in FIG. 4).

Figure 7B:
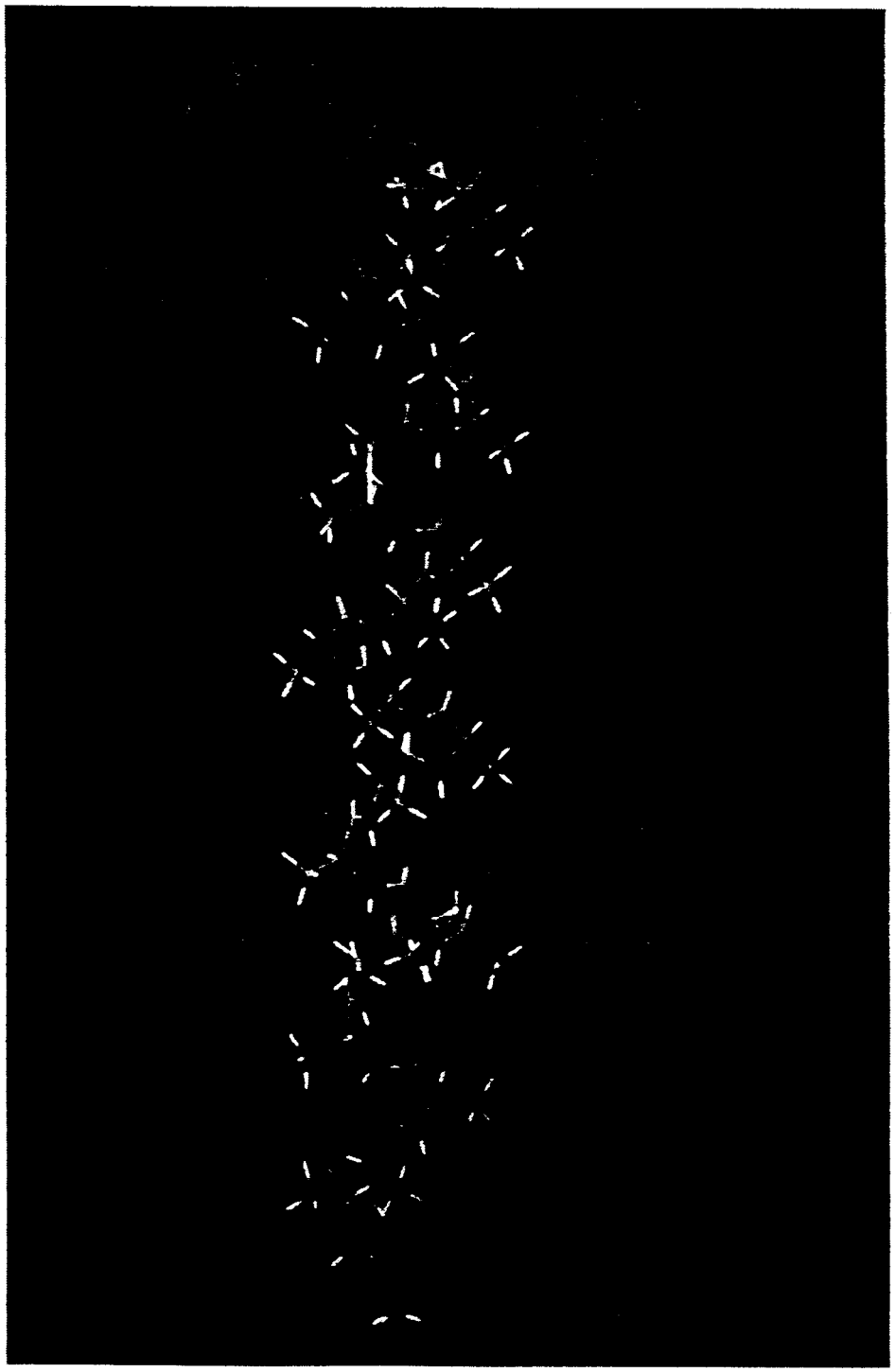
FIG. 7B is a graphic display of a three-dimensional peptide structure, illustrating Poly-L-alanine.
Figure 11:
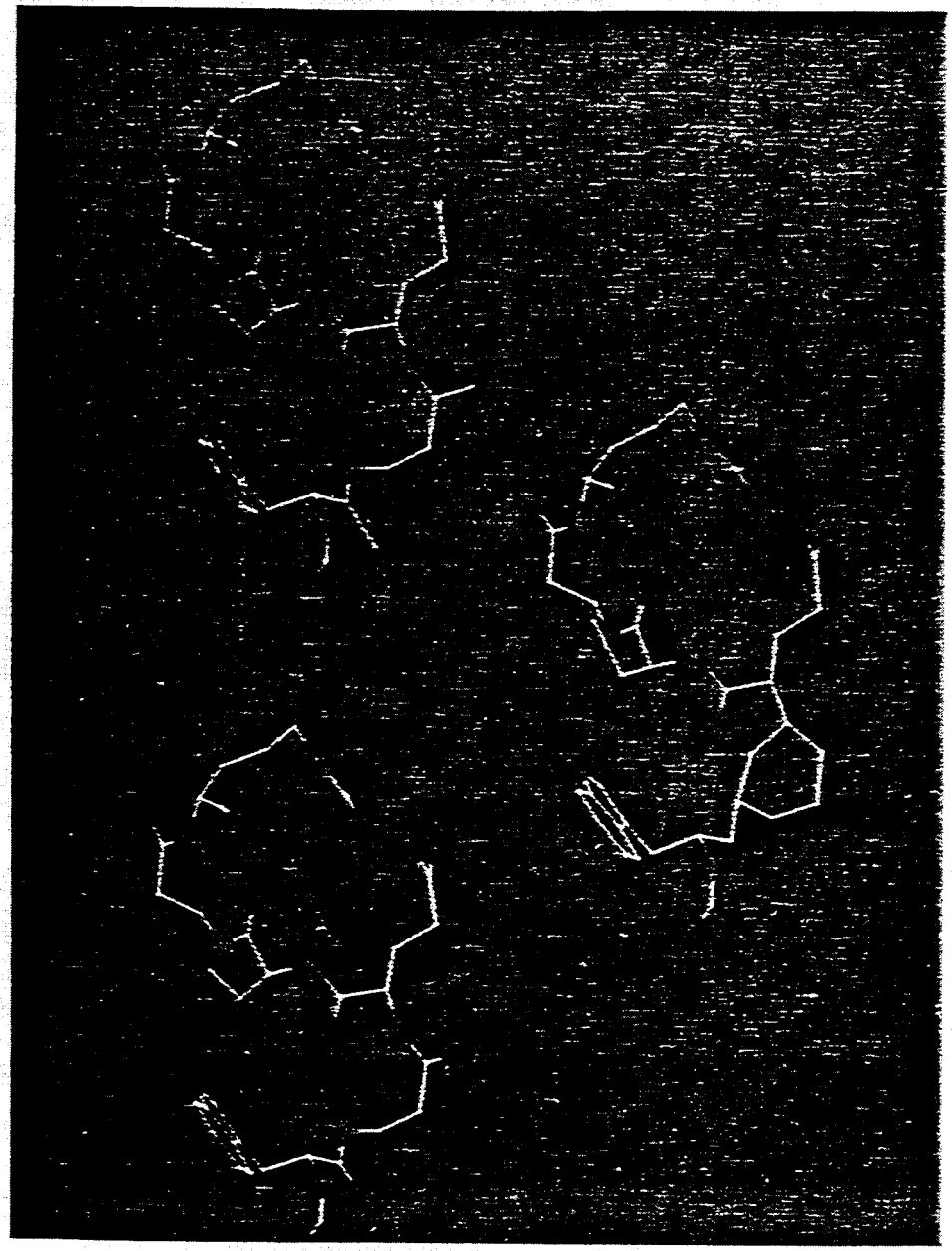
FIG. 11 shows graphic displays of three-dimensional peptide structures related to Example 1.

In accordance with a preferred analyzing step, the $\phi$, $\psi$ angles for the most probable structures are computed (or otherwise retrieved from prior computations) and are used to construct one or more Balaji plot(s) that represent the simulated conformation, as indicated at block 87 of FIG. 7A. The conformations indicated by these plots are then further examined, as required, for consistent structural features (block 88). This examination may be aided, as desired or required, by examining models of the structures thus predicted by three-dimensional graphic display (also block 88) using techniques known in the art. See, e.g., Molecular Display Program MOGLI Version 2.0, available from Evans and Sutherland Computer Corporation, Salt Lake City, Utah. A sample of a representative graphic display showing a three dimensional peptide structure (for ploy-L-alanine) can be seen in FIG. 7B. Another representative graphic display is seen in FIG. 11, discussed below in connection with Example 1.

The Balaji Plot

Figure 8A:
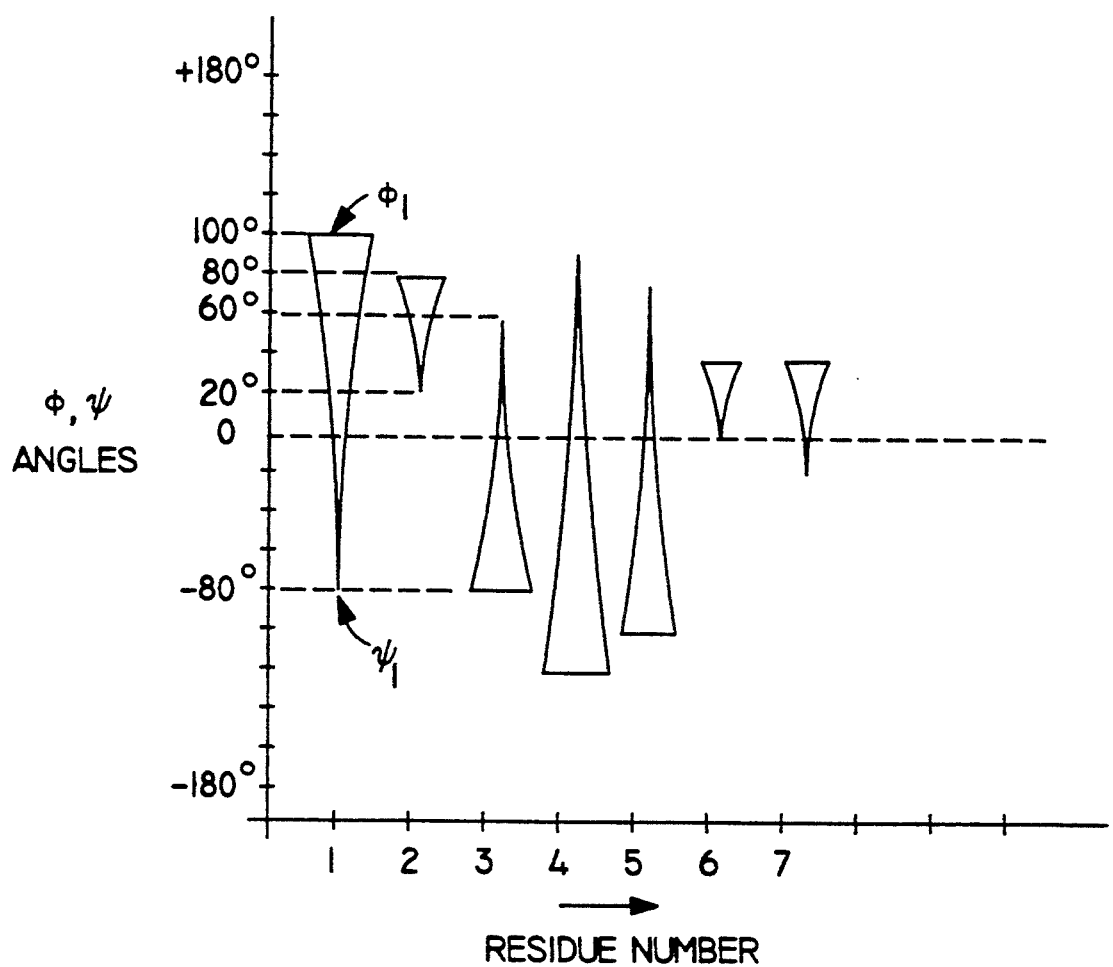
FIG. 8A is a Balaji plot of a representative oligopeptide showing the use of a wedge for each residue to represent the $\phi$, $\psi$ values, with the base of the wedge corresponding to the $\phi$ angle and the tip of the wedge corresponding to the $\psi$ angle.

Reference is next made to FIG. 8A to describe a Balaji plot and how it is used by the present invention (not only for purposes of analyzing the predicted structures to determine the most probable, but also for other facets of the invention herein described). FIG. 8A shows a Balaji plot of the $\phi$, $\psi$ angles of a hypothetical polypeptide (only the first seven residues of which are shown). The Balaji plot includes an angular vertical axis, and a residue number horizontal axis. The vertical angular axis has a range of angles covering 360°, or $2\pi$ radians, preferably centered about 0° or 0 radians. As shown in FIG. 8A, for example, the angular vertical axis includes marks for every 20°, ranging from +180° to −180°. Of course, as needed for a particular application, the angular axis could be marked in angular units other than degrees, e.g., radians. However, as most chemical and physical data for peptides typically identifies the $\phi$, $\psi$ angles in degrees, the use of degrees for the angular axis is preferred. The horizontal axis is marked with the residue number. Only seven residue numbers are shown in FIG. 8A, but it is to be understood that the horizontal axis continues for as many residues as are included in a particular polypeptide chain. See, e.g., FIGS. 14–22 which show Balaji plots for actual polypeptides. It is also to be understood that while the angular axis is shown in FIG. 8A as the vertical axis, and the residue axis is shown as the horizontal axis, these roles could be reversed. All that matters is that the two axes be orthogonal to each other, or have a defined angular relationship relative to each other.

As shown in FIG. 8A, the $\phi$, $\psi$ angles are represented in the Balaji plot as the base and tip of a wedge, respectively. One wedge is included for each residue, and the wedge is positioned in alignment with the horizontal axis so as to indicate the particular residue number of the $\phi$, $\psi$ angles thus plotted. Thus, for example, as seen in FIG. 8A, the first residue of the particular peptide represented, has a $\phi$ angle of 100°, and a $\psi$ angle −80°. Similarly the second residue has a $\phi$ angle of 80° and a $\psi$ angle of 20°. The third residue has a $\phi$ angle of −80°, and a $\psi$ angle 60°. In a similar manner, the $\phi$, $\psi$ angles for each residue are defined on the Balaji plot.

It is noted that the Balaji plot is a refinement or modification of a "Balasubramanian Plot". See, Balasubramanian, R., "New type of representation for Mapping Chain Folding in Protein Molecules," *Nature* 266, pp. 856–857 (1974). The Balasubramanian Plot represents the values of the $\phi$, $\psi$ angles of each residue of a polypeptide chain as solid dots and open circles, respectively, connected by a vertical line. The Balasubramanian plot utilizes a vertical angular axis, and a horizontal residue number axis. The peptide is thus depicted in a Balasubramanian plot as a series of different vertical lines, each having solid dots and open circles aligned with the corresponding $\phi$, $\psi$ angle values on the vertical axis, and where each line corresponds to the particular number of the residue having the plotted $\phi$, $\psi$ angles as indicated on a horizontal axis.

In contrast to the Balasubramanian plot, the Balaji plot of the present invention shows the values of the $\phi$, $\psi$ angles as the base and tip of a vertical wedge (assuming a vertical angular axis), respectively, with a separate wedge being horizontally positioned on the plot as a function of the residue number of the $\phi$, $\psi$ angles thus plotted. In other words, the Balaji plot replaces the solid dots and open circles of the Balasubramanian Plot with the base of a wedge and the tip of a wedge, respectively; and further replaces the vertical line joining the dots and open circles of the Balasubramanian plot with the body of the wedge. This seemingly small difference provides a remarkable advantage, however, in an analyst's ability to view the Balaji plot and gain additional insight into the manner in which a particular polypeptide has folded or otherwise arranged its various residues in a complex conformation.

Figure 8B:
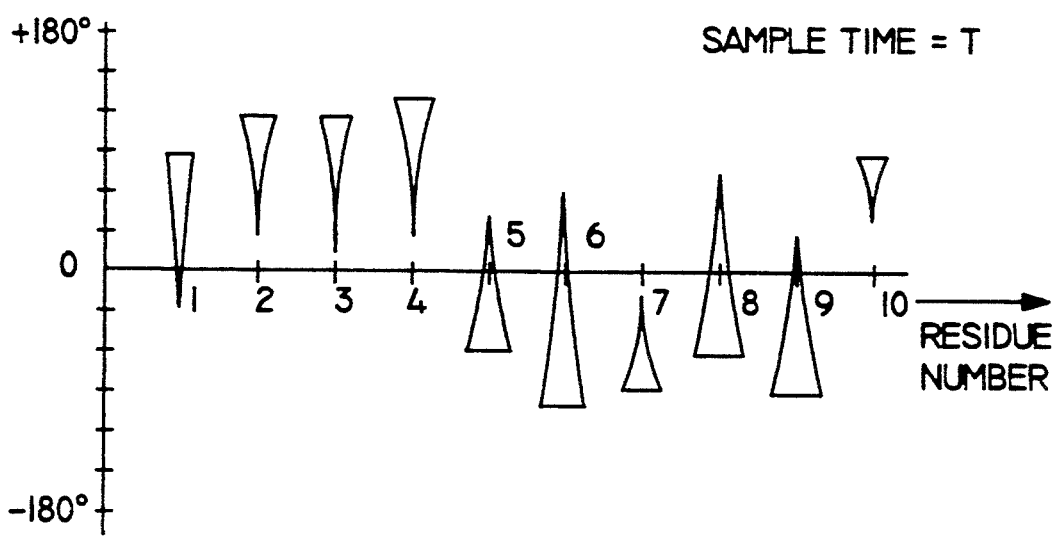
FIGS. 8B and 8C show Balaji plots for time T and T+$\Delta$t for a representative oligopeptide that has been expanded in accordance with the simulation techniques of the present invention.
Figure 8C:
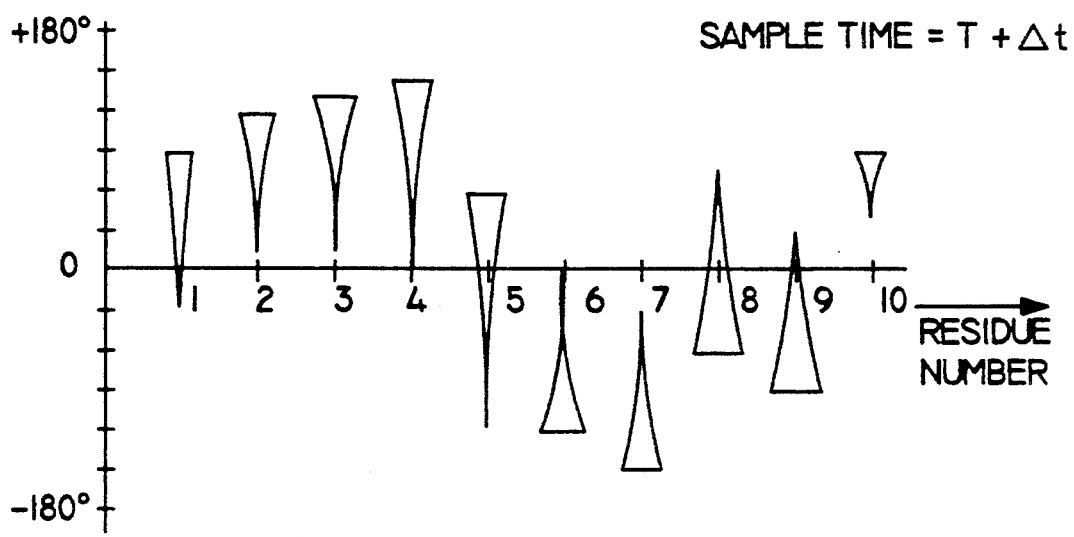
Figure 8D:
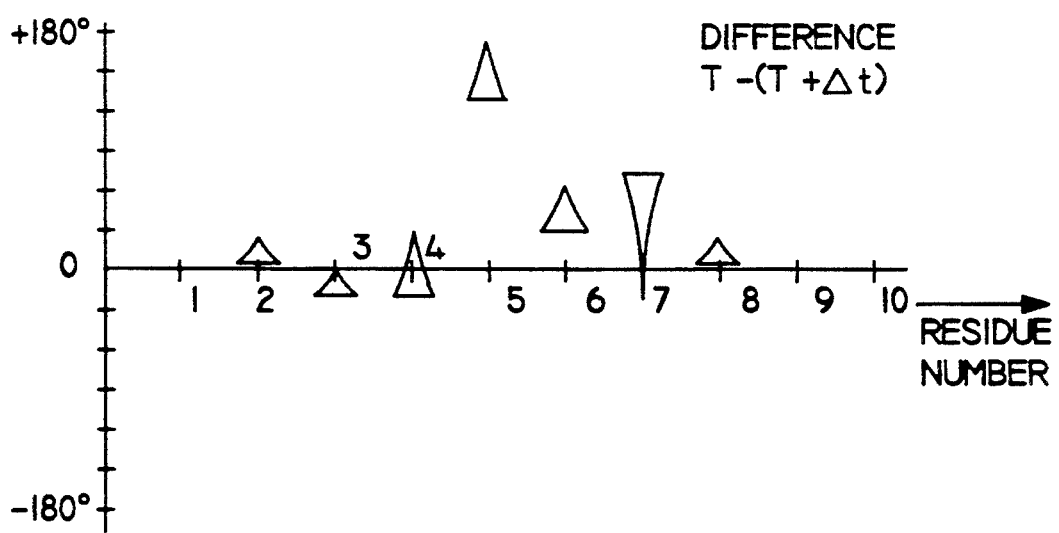
FIG. 8D shows a Balaji plot of the difference between FIGS. 8B and 8C.

To illustrate one use of the Balaji plot in accordance with the present invention, reference is next made to FIGS. 8B, 8C, and 8D, where there are shown Balaji plots for times T and T+Δt, and the difference therebetween, respectively, for a hypothetical peptide that has undergone molecular dynamic changes, i.e., that has experienced some external or internal force that has caused its conformation to change. As the conformation of the peptide changes, the $\phi$, $\psi$ angles are recorded or otherwise determined. Thus, as seen in FIG. 8B, at the sample time T, the first residue has $\phi$, $\psi$ angles of approximately 90° and −30°, respectively. As seen in FIG. 8C, at a sample time Δt later, i.e., at T+Δt, the first residue also has $\phi$, $\psi$ angles of 90° and −30°, respectively. Thus, the angles of this residue have not changed during the time period Δt, and hence there is no "wedge" shown in FIG. 8D, the "differential Balaji plot", for the first residue.

The second residue, in contrast, does show a slight change in the angle $\psi$, but not the angle $\phi$, during the time Δt. That is, at the sample time T (FIG. 8B), the $\phi$, $\psi$ angles for the second residue are approximately +120° and +30°, respectively; whereas at sample time T+Δt (FIG. 8C), the $\phi$, $\psi$ angles are approximately +120° and +15°, respectively. Thus, in the differential Balaji plot, FIG. 8D, there is a very small wedge for the second residue indicating a 0° difference for the $\phi$ angle, and a +15° difference for the $\psi$ angle.

Similarly, it is seen that the third residue undergoes a slight change in the $\phi$ angle during the time Δt, whereas the $\psi$ angle of the third residue does not change. That is, at the sample time T (FIG. 8B), the $\phi$, $\psi$ angles for the third residue are approximately +120° and +15°, respectively; whereas at sample time T+Δt (FIG. 8C), the $\phi$, $\psi$ angles are approximately +135° and +15°, respectively. Thus, in the differential Balaji plot, FIG. 8D, there is a very small wedge for the third residue indicating a −15° difference for the $\phi$ angle, and a 0° difference for the $\psi$ angle.

Thus, it is seen that not only do the Balaji plots of FIGS. 8B and 8C provide valuable insight into the structure of the particular polypeptide being represented, but the differential Balaji plot (FIG. 8D) clearly shows how the structure has changed over the time Δt. If the $\phi$, $\psi$ angles of a given residue have not changed, there is no wedge in the differential Balaji plot for that residue. If the $\phi$, $\psi$ angles for a given residue have changed only a small amount, the wedge appearing in the differential Balaji plot is a small wedge near 0°. If, on the other hand, the $\phi$, $\psi$ angles have changed by a significant amount for a given residue during the time Δt, the wedges appearing in the differential plot corresponding to that residue will either be large wedges and/or not close to 0°. That is, either the base of the wedge and/or the tip of the wedge will show a large deviation from 0°.

A quick glance at the differential Balaji plot shown in FIG. 8D thus reveals that the fifth residue has $\phi$, $\psi$ angles that have changed a significant amount. The wedge for the fifth residue, although not large, has a large displacement from 0°, having its base at +120° and its tip at 165°. This signifies that the $\phi$, $\psi$ angles have changed in the time Δt by +120° and +165°, respectively. Other residues showing a significant change in the $\phi$ or $\psi$ angles are residue number 6 (a Δ$\psi$ of +60°) and residue number 7 (a Δ$\phi$ of +75). Hence, one studying the Balaji plots of FIGS. 8B–8D is quickly led to the conclusion that most of the $\phi$, $\psi$ angles of the residues of the represented structure are fairly stable (some with no change at all), except for residues 5, 6 and 7. Thus, if the goal is to maintain a desired conformation, e.g., as represented by the Balaji plot of FIG. 8B, then the Balaji plots shown in FIGS. 8B–8D may thus be used as an analytical tool to prompt one to look for a suitable bioisostere, or equivalent, that could replace the amide bonds of residues 5, 6, and 7 with a more stable bond.

Figure 8E:
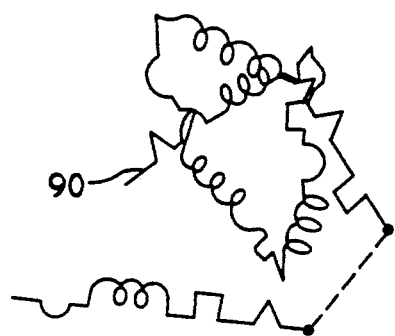
FIG. 8E schematically depicts a complex folded polypeptide.
Figure 8F:
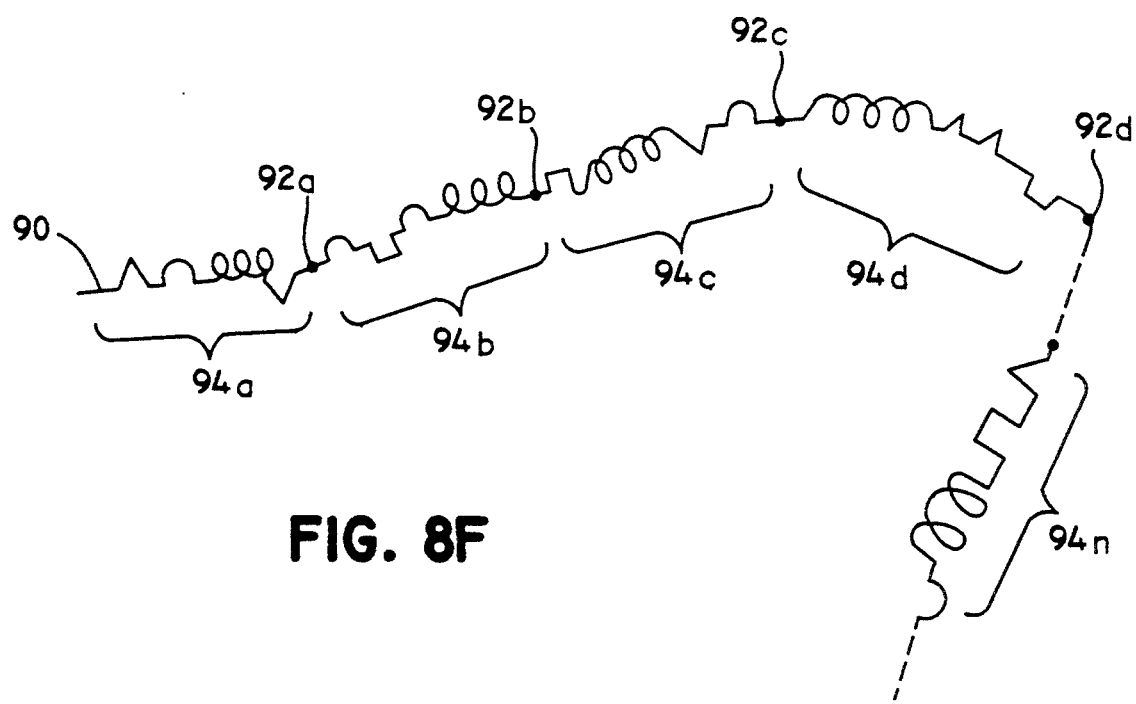
FIG. 8F schematically depicts the polypeptide of FIG. 8E when unfolded.

The significance of the Balaji plot as an analytical tool is highlighted by FIGS. 8E and 8F. FIG. 8E schematically depicts a complex three-dimensional folded polypeptide, represented by the folded, twisted line 90 having numerous bumps and coils along its length. Such a complex shape may appear impossible to characterize and understand, even though the primary structure of the polypeptide is known. However, through the simulation methods of the present invention, i.e., by shrinking the polypeptide in a solvent box and expanding it to and beyond its normal size, one or more Balaji plots characterizing the $\phi$, $\psi$ angles or the changes in the $\phi$, $\psi$ angles may be generated. Such plots may clearly show that only a handful of the $\phi$, $\psi$ angles of the numerous residues in the polypeptide exhibit any propensity for change. These angles, i.e., the residues containing these angles, may thus be considered as the hinges or swivel points of the chain. By selectively unfolding the chain at these hinge or swivel points, the complex shape of FIG. 8E may readily unfold and untangle to reveal a series of simple, well recognized shapes, e.g., secondary structures, as schematically shown in FIG. 8F.

In FIG. 8F, which is simply an unfolded equivalent of the schematic representation of FIG. 8E, it is seen that several series of simple shapes 94a, 94b, 94c, . . . , 94n, schematically representing known compounds or short peptides, are joined together at hinge or swivel points 92a, 92b, 92c, . . . , 94n. By folding the chain 90 at the hinge points 92a, 92b, 92c, . . . , 92n, several complex three-dimensional conformations may result, that which is shown in FIG. 8E being one of them. The problem is that it is very difficult to recognize the series of simple shapes 94a, 94b, 94c, . . . , 94n hidden in the complex shape shown in FIG. 8E. However, with the aid of the Balaji plots of the present invention, it is relatively simple to untangle the complex shape of FIG. 8E in order to recognize its constituent parts.

As thus seen from FIGS. 8E and 8F, the Balaji plots serve not only as a convenient means for displaying the data associated with a peptide-based compound, including allowing such data to be analyzed for the purpose of ascertaining the most probable structures, but the Balaji plot is also a very valuable analytical tool for untangling complex polypeptide conformations, thereby providing keen insight into how the peptide might be mimicked and/or stabilized for the purpose of providing a peptidomimetic useful for drug design.

The Conformational Energy Map

Figure 9A:
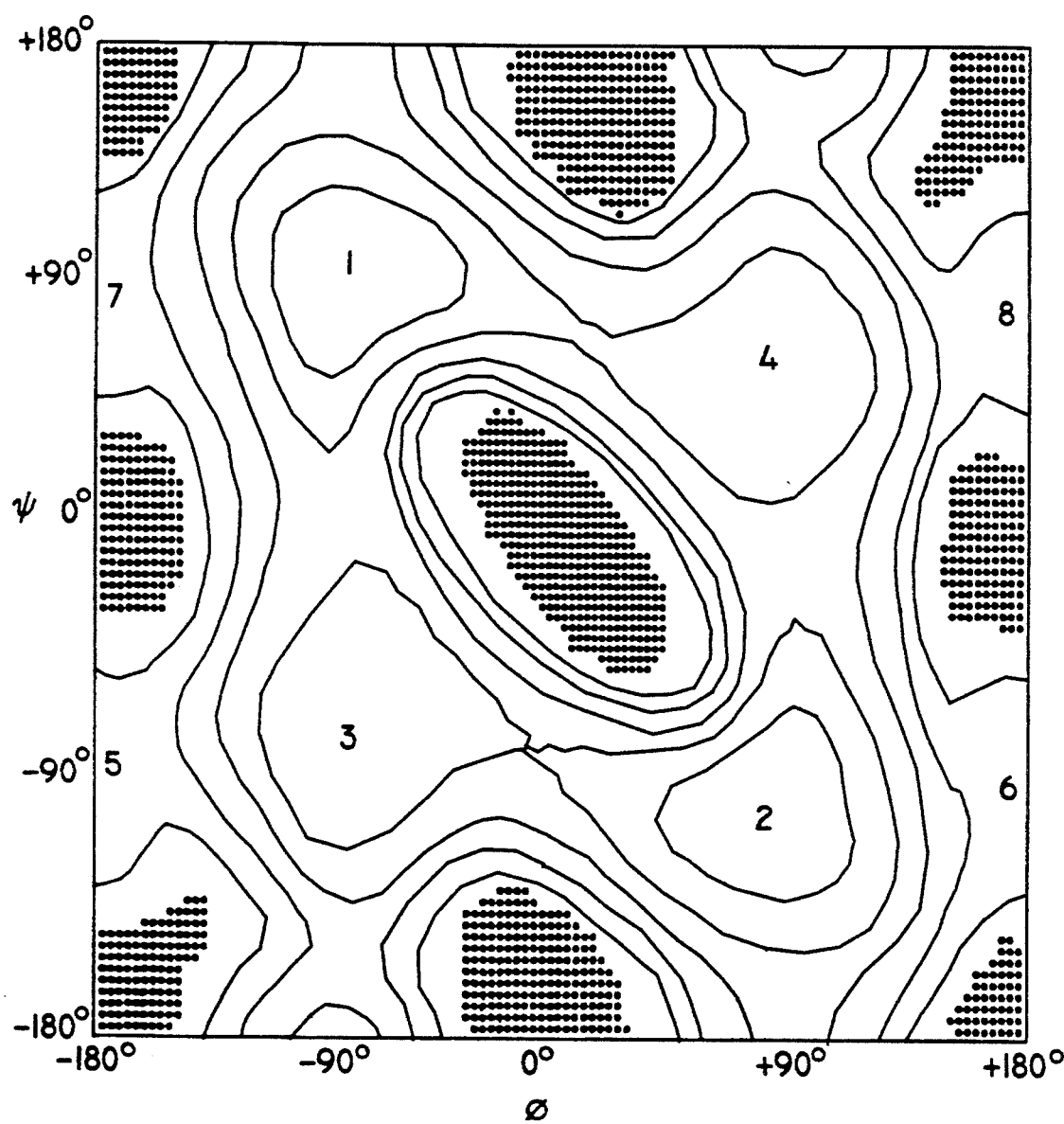
FIG. 9A shows a representative conformational energy map of an oligopeptide as generated by computer simulation in accordance with the present invention.

Referring next to FIG. 9A, another tool useful in analyzing a simulated or other peptide structure is shown. This tool is the conformational energy map. FIG. 9A shows a representative conformational energy map of an oligopeptide (more particularly, the dipeptide cyclopropyl). This energy map is generated by computer simulation of the oligopeptide in accordance with the present invention. The computer program used to generate the conformational energy map is referenced below. The conformational energy map shows the energy required to maintain a particular $\phi$, $\psi$ angle of the oligopeptide conformation. Thus, a stable conformation corresponds to an area on the energy map having the lowest energy to maintain the $\phi$, $\psi$ angles for that conformation.

AS seen in FIG. 9A, the $\phi$ angle is plotted along one axis of the energy map, and the $\psi$ angle is plotted along the other axis of the energy map. As drawn in FIG. 9A, the $\phi$ angle is plotted along the horizontal axis, and the $\psi$ angle is plotted along the vertical axis. (In some energy map representations, including Table 1 below, the angles $\theta_1$, $\theta_2$ may be used in place of the angles $\phi$, $\psi$, respectively.) Any combination of the $\phi$, $\psi$ angles is thus represented as a point in the energy map corresponding to the intersection of the $\phi$ angle with the $\psi$ angle.

The energy of the particular $\phi$, $\psi$ combination is indicated by a series of energy contour lines, or equivalent, appearing on the surface of the energy map. As drawn in FIG. 9A, the heavier or bolder the energy contour line, the lower the energy at that location (and hence the more stable the conformation). Likewise, the lighter or thinner the energy contour line, the higher the energy at that location (and hence the more unstable the conformation). The areas of highest energy are shown as shaded areas. Such shaded areas may be considered as "peaks" (highest energy points), and the areas encircled by the boldest contour lines may be considered as "valleys" (lowest energy points). A stable conformation of the peptide is thus one where the $\phi$, $\psi$ angles are located in a "valley" or location of minimum energy.

To illustrate, in FIG. 9A the point $(\phi, \psi)=(0°, 0°)$, corresponds to a location of relatively high energy, i.e., a point where the molecular dynamics do not permit the $\phi$, $\psi$ angles to stay in that position if they are not constrained. Hence, this point is not a stable conformation In contrast the point $(\phi, \psi)=(-80°, 100°)$ corresponds to a location of minimum energy, and a more stable conformation. As seen in FIG. 9A, there are some eight regions of minimum energy for the peptide shown, marked by the white-on-black numerals 1–8. The relative energy associated with each of these "pockets" or valleys of minimum energy are quantified and ordered as shown below in Table 1.

Table 1 lists both the values of the $\phi$, $\psi$ angles (identified as the angles $\theta_1$ and $\theta_2$) that define the particular minimum energy location, and the relative energy of the minimum location, with the minimum or lowest energy being set equal to 0.0. Thus, it is seen from Table 1 and FIG. 9A that the global minimum (that area of lowest energy) is area number 1 centered at $(\theta, \psi)=(-80°, 100°)$. The area of next lowest energy is the area number 2 centered at $(\phi, \psi)=(80°, -100°)$. Note from Table 1 that the global minimum occurs at $(\phi, \psi)=(-80°, 100°)$ and corresponds to an energy of 112.1 kcal/mol. The relative energy associated with the local minimum at $(\phi, \psi)=(80°, 100°)$ is 0.1, indicating that the energy is some 10% higher at this location. In contrast, the relative energy associated with the local minimum at $(\phi, \psi)=(-80°, -70°)$, is 1.1, or roughly twice as much as the energy at the global minimum.

TABLE 1

| Global minimum occurs at $\theta_1$, $\theta_2$ = 80°, 100° (energy = 112.1 kcal/mol) | | |
|---|---|---|
| Min. # | $\theta_1$ (°) | $\theta_2$ (°) | |
| 1 | 80 | 100 | 0.0 |
| 2 | 80 | −100 | 0.1 |
| 3 | −80 | −70 | 1.1 |
| 4 | 80 | 70 | 1.1 |
| 5 | −180 | −90 | 4.0 |
| 6 | 180 | −90 | 4.1 |
| 7 | −180 | 90 | 4.1 |
| 8 | 180 | 90 | 4.2 |

Percent occupation of the 1 to 5 kcal/mol energy (thickest = 1 and thinnest = 5).
Shaded areas correspond to energy > 6.5 kcal/mol
Relative energy inkcal/mol (globalminimum set to 0.0).

The conformational energy map provides a useful tool because it provides a visual indication of the global minimum conformation for a given peptide. Such a map therefore provides valuable insight into selecting the most probable simulated conformation for which a chemically modified analog should be designed. The energy maps also provide useful information relative to the overall search for and design of a suitable peptidomimetic that can mimic a desired peptide.

It is noted that conformational energy maps for model dipeptide compounds have been reported in the literature. See, e.g., Ramachandran, et al., (1968) supra. Preliminary data on dipeptide conformational energy maps containing thiopeptide and peptide analogs with glycyl, alanyl and Aib ($\alpha$-amino) isobutyric acid) units, for example, may be found in Balaji et al., "Mean Geometry of the Thiopeptide Unit and Conformational Features of Dithiopeptides and Polythiopeptides," *Biochem. Biophys. Res. Commun.*, 145:834 (1987); and Balaji et al., *Peptides*, p. 639 (Ed. J. E. Rivier), ESCOM, Leiden (1990).

The present invention advantageously includes a refined protocol for obtaining conformational energy maps and a compilation of conformational features of several novel model dipeptide analogs. This protocol includes computing the conformational energies using a suitable molecular mechanics simulation program. The energies are computed in the $(\phi, \psi)$ plane. The parameters used for such computation are those derived by fitting the dipole moments to experimental and Gaussian 80/82 structures, and conformational energies of model compounds (e.g., peptides and thiopeptides). Preferably, all the calculations are performed using monopole charges and a dielectric constant of 4.0. The $(\phi, \psi)$ angles are frozen to determine the energy at a particular $(\phi, \psi)$ point in the map. For each frozen $(\phi, \psi)$ point, the energy is minimized using convergence criteria of 0.1 kcal/mole. The conformational energy contour maps (with trans peptide and thiopeptide units) are preferably plotted in the $(\phi, \psi)$ plane at 1 kcal/mole intervals with respect to the global minimum for each of the modeled compounds. Contours greater than 5 kcal/mole are omitted. The percentage availability of the conformational space with 1, 2, 3, 4, and 5 kcal/mole from the global minimum for each conformational energy map are computed. Probability maps are then computed at 300° K.

Figure 9B:
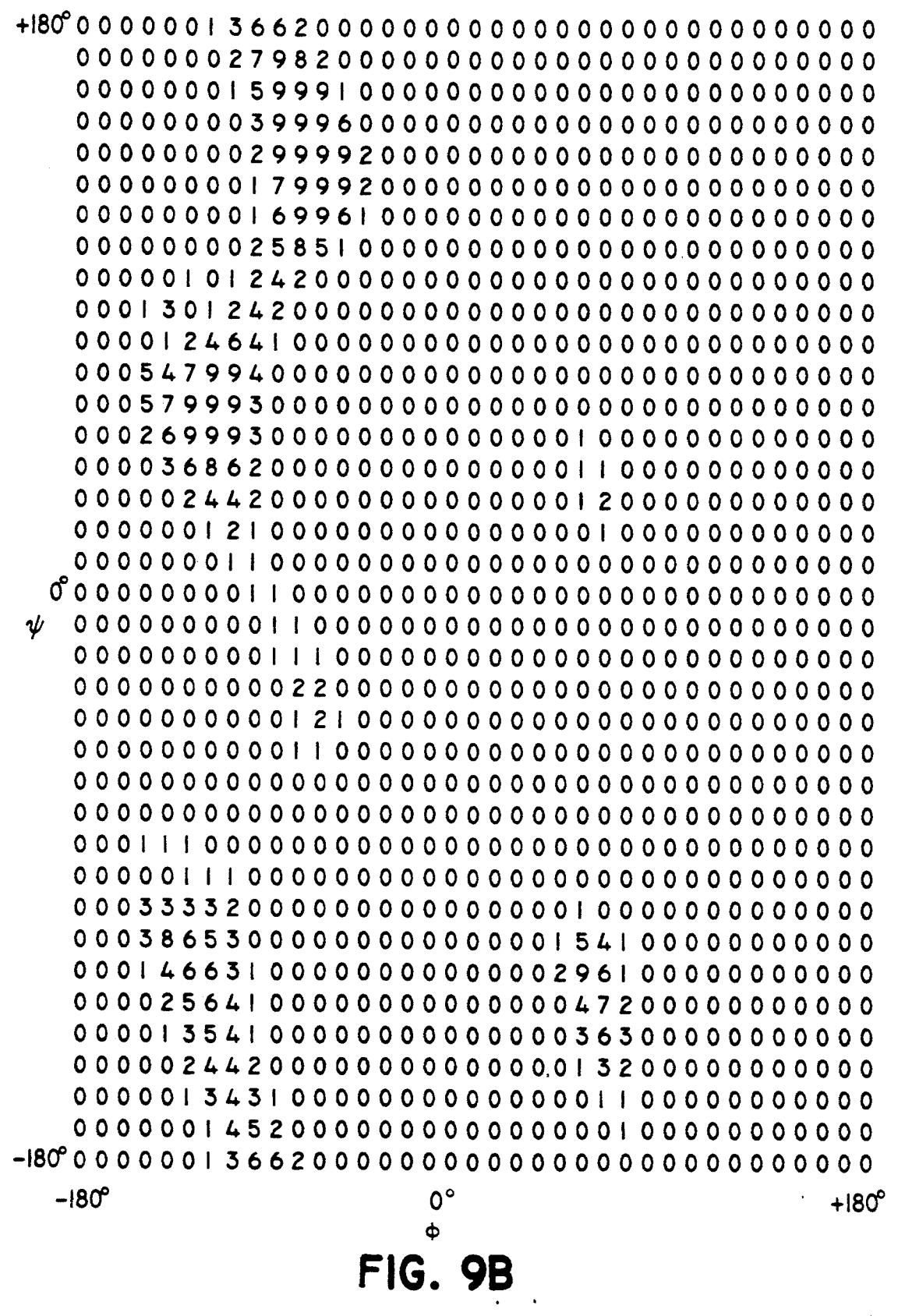

FIG. 9B depicts contour probability data for a model compound generated using the above-described protocol. This data is also organized into a map much as the conformational energy map, with the value of $\phi$ being defined along one axis, and the value of $\psi$ being defined along the other axis. The numbers shown on the map provide an indication of the relative population of the molecules in the total $\phi$, $\psi$ space of each minima, with the higher numbers indicating the higher probability. The contour probability data thus also provides a useful tool in identifying the most probable structures for which chemically modified analogs way be designed.

The compilation of conformational features of several novel model oligopeptides, e.g., dipeptide analogs, are set forth below. These features are very useful in searching for and/or designing a chemically modified analog to mimic a desired peptide.

Peptidomimetic Design and Synthesis of Chemically Modified Analogs

The fourth step of the drug design method (block 24 in FIG. 4) of the present invention is designing and synthesizing a chemically modified analog of the selected simulated peptide. Some of the resulting chemically modified analogs will be biologically active, and, as such, can be employed as peptidomimetics without further modification.

In general, the designing and synthesizing of a chemically modified analog involves starting with the sequence of the peptide and the conformation data (e.g., geometry data, such as bond lengths and angles) of a desired peptide (e.g., the most probable simulated peptide), and using such data to determine the geometries that should be designed into the chemically modified analog. Numerous methods and techniques are known in the art for performing this step, any of which could be used. See, e.g., Farmer, P. S., *Drug Design*, (Ariens, E. J. ed.), Vol. 10, pp. 119-143 (Academic Press, New York, London, Toronto, Sydney and San Francisco) (1980); Farmer, et al., in *TIPS*, 9/82, pp. 362-365; Verber et al., in *TINS*, 9/85, pp. 392-396; Kaltenbronn et al., in *J. Med. Chem.* 33: 838-845 (1990); and Spatola, A. F., in *Chemistry and Biochemistry of Amino Acids, Peptides, and Proteins*, Vol. 7, pp. 267-357, Chapter 5, "Peptide Backbone Modifications: A Structure-Activity Analysis of Peptides Containing Amide Bond Surrogates. Conformational Constraints, and Relations" (B. Weisten, ed.; Marcell Dekker: New York, pub.) (1983); Kemp, D. S., "Peptidomimetics and the Template Approach to Nucleation of $\beta$-sheets and $\alpha$-helices in Peptides," *Tibech*, Vol. 8, pp. 249-255 (1990).

Figure 10:
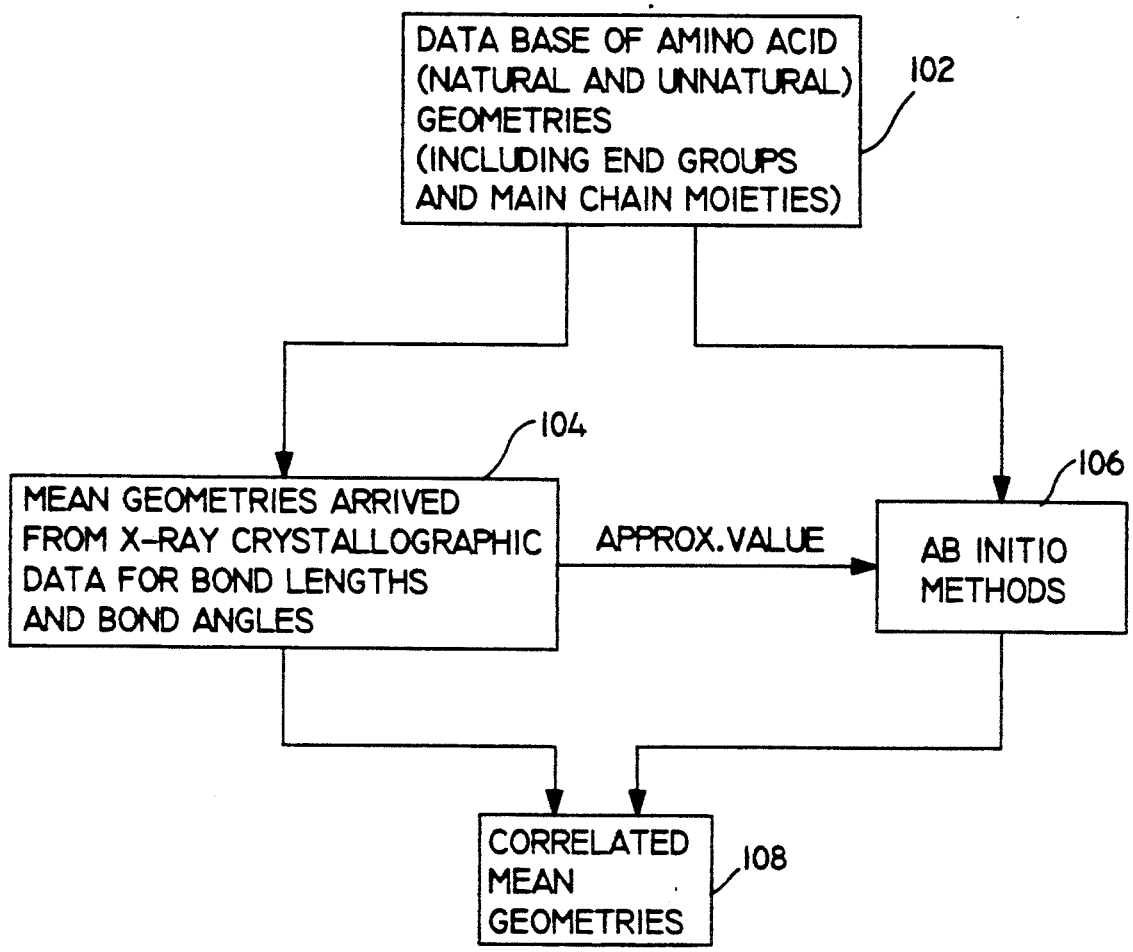
FIG. 10 shows one manner of designing and synthesizing rigid or otherwise chemically modified analogs in accordance with the present invention.

A preferred technique for providing useful data and other information that aids in the design and synthesizing of a chemically modified analog is shown in the chart of FIG. 10. As shown in FIG. 10, at least two parallel, yet inter-related paths or methods, are used in arriving at mean geometry data. Because the paths are interrelated, the resulting mean geometry data is advantageously correlated with the two (or more) methods used, thereby providing the best design information for use in synthesizing the chemically modified analog.

As shown in FIG. 10 (block 102), a data base of amino acid geometries (both natural and non-natural, including end groups and main chain moieties) provides input data that may be used to arrive at mean geometry data for use in the design of chemically modified analogs. From the data in the data base (102), for example, mean geometry data may be arrived at from x-ray crystallographic data of bond lengths and angles, as indicated at block 104. Conventional techniques are used for this purpose. Such x-ray crystallographic data provides a first approximate value of the mean geometries of the desired analog.

In addition to the conventional x-ray crystallographic data, a second technique for arriving at mean geometry data is to use the ab initio techniques previously described to predict a stable peptide structure (block 106). Advantageously, the ab initio method may utilize the data from the data base (102), the x-ray crystallographic data (104), and/or no initial data to arrive at a prediction of the peptide structure, and hence a measure of the mean geometry. Included in the ab initio technique, of course, are the molecular mechanical parameters that define a second approximate value of the mean geometries of the desired analog.

The first and second approximate mean geometry values are then correlated, using a suitable correlation method, as indicated at block 108 of FIG. 10. The selected correlation method is preferably a weighted average of the two approximate values, with more weight given the ab initio simulation data than is given to the x-ray crystallographic data.

Once mean geometries of the desired analog are established, and those residues of the original peptide which are particularly prone to rearrangement and/or degradation have been identified, modifications of the original peptide can be considered. Those of skill in the art are well aware of numerous peptide backbone substitutions which can impart enhanced rigidity, chemical and/or metabolic stability, etc., to a peptide. For example, the normal amide bond of a peptide backbone can be modified by replacement of the amide nitrogen with a methylene moiety (i.e., —CH$_2$—), an oxygen moiety (—O—), or a sulfur moiety (—S—), or by replacement of H at the amide nitrogen with a suitable R-group, thereby producing an N-substituted amide.

Alternatively, the normal amide bond of a peptide backbone can be modified, for example, by replacement of the amide carbonyl group with a reduced carbonyl (i.e., —CH$_2$—); an $\alpha,\alpha$-disubstituted methylene moiety:

wherein each of R and R' are independently H or a hydrocarbyl or substituted hydrocarbyl radical, oriented so as to produce either the L- or D-configuration; a thiocarbonyl group:

a sulfone moiety; a sulfoxide moiety; or the like.

Additional modification of the peptide can be accomplished by introducing substituents at the alpha-carbon atom, such that the peptide backbone is unchanged, but additional side chain substituents are present in the chemically modified analog. For example, the α-carbon atom can be part of a cyclopropyl group:

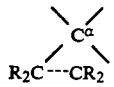

an ethylidene group:

an amine group:

and the like.

Those of skill in the art recognize that various combinations of the above-described modifications can be employed. For example, the entire amide moiety can be replaced by:

(a) a thioalkyl unit (—S—CH$_2$—),
(b) the methylenesulfone bioisostere:

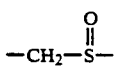

(c) the methylenesulfoxide bioisostere:

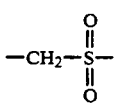

(d) an ethylene unit (—CH$_2$—CH$_2$—),
(e) the ketomethylene bioisostere:

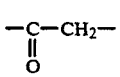

(f) the methyleneamino bioisostere:

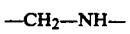

(g) the methylenehydroxyamino bioisostere:

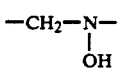

(h) the N-methyl peptide bioisostere:

(i) an isopropenyl unit:

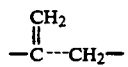

(j) the thiopeptide (i.e., thioamide bond) bioisostere:

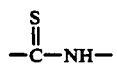

(k) the N-methyl thiopeptide bioisostere:

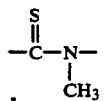

(l) the ester bioisostere:

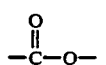

(m) an alkylether unit (—O—CH$_2$—),
(n) a "reverse" amide unit i.e.,

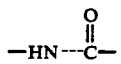

instead of

and so on. Note that each of these replacement groups can be introduced into the peptide chain in either orientation (i.e., in the orientation shown, or in the "reverse" orientation.

Alternatively, the entire amide moiety can be replaced with:

(a) an ethylidene unit (—CH=CH—),
(b) the hydroxyethylene bioisostere:

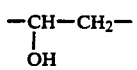

(c) a dihydroxyethylene unit:

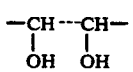

(d) the epoxide bioisostere:

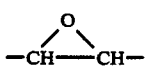

(e) the hydroxy double bond bioisostere:

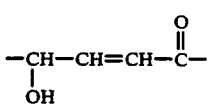

(f) the trihydroxy bioisostere:

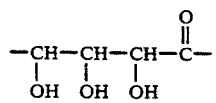

(g) a 2, 5-pyrrole unit:

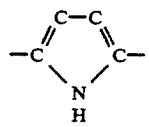

and so on.

In addition, those of skill in the art recognize that various substituents on the amide nitrogen and the α-carbon can be bound to one another, thereby forming a cyclic structure which will also produce a constrained analog. Other constrained, cyclic structures are also possible by linking other substituents so as to form cyclic structures.

Since the replacement residues are not typically recognized by the enzymes which degrade naturally occurring proteins, these chemically modified analogs typically are much more resistant to enzymatic cleavage than are the native peptides from which they are derived. In addition, the wide range of possible replacement groups which can be used to modify the backbone and side chains of peptides affords the opportunity to reduce the conformational flexibility of the parent structure. Thus, the possibility that the peptide will adopt conformation(s) other than the specifically desired conformation(s) can be substantially minimized by appropriate modification of the peptide.

Once the desired analog (including backbone and side chain modifications, as appropriate) has been identified, chemical synthesis is undertaken, employing standard synthetic techniques. For a given target compound, the skilled artisan can readily identify suitable synthetic approaches for the preparation of the target compound.

Evaluate Bioactivity

The fourth step of the drug design method of the present invention (block 26 of FIG. 4) is to evaluate the bioactivity of the synthesized chemically modified analog. Standard physiological, pharmacological and biochemical procedures are available for testing the chemically modified analog compounds. The particular protocol employed for evaluating bioactivity is a function of the compound being tested. For example, a compound thought to function as a renin antagonist can be assayed in hypertensive rats [see, e.g., Kaltenbronn, et al., in J. Med. Chem, 33:838-845 (1990)]; As another example, since gonadotropin releasing hormone (GnRH) is known to stimulate gonadotropin release from the pituitary gland (thereby making possible fertility in both male and female animals), antibodies or a designed drug that blocks GnRH-stimulated gonadotropin release can be recognized using pituitary cell culture techniques to measure the degree of inhibition of gonadotropin release from these cells [see Valadez, F. J., Staley, D., and Conn, P. M., Release of gonadotropin alpha subunit from rat pituitary cultures in response to GnRH, Mol. Cell Endocrinol 56:81-89 (1988)]. The effectiveness of the agent to block fertility is then tested in field trials using various mammalian animal models.

As yet another example, the effectiveness of an endothelin antagonist (endothelin is a potent endogenous vasoconstrictor peptide that is involved in hypertension; an endothelin antagonist is an antibody or drug designed to inhibit endothelin-stimulated vasoconstriction and contractions) can first be determined using rat portal vein and aorta as well as rat euterus, trazchea and vas deferens [see Borges, R., Yon Grafenstein, H. and Knight, D. E., Tissue selectivity of endothelin, Eur. J. Pharmacol 165:223-230, (1989)], and finally the bioactivity can be tested in hypertensive rats (see Kaltenbronn, et al., supra.

As still another example, the bioactivity of antibodes or drugs that mimic porcine somatotropin (pST, growth hormone) stimulation of pig growth can be determined by first testing the bioactivity of pST mimics using a rat tibia bone culture assay to measure the pST-stimulated release of insulin-like growth factor-I/somatomedin-C [see Stracke, H., Schultz, A., Moeller, D., Rossol, S., and Schatz, H., Effect of growth hormone on osteoblasts and demonstration of somatomedin-C/IGF-I in bone organ culture, Acta Endocrinol. 107:16-24 (1984)]. The bioactivity of the antibodies or test compounds are then tested in pigs to determine if they stimulate growth in a feed-efficient manner. Any suitable method, or combination of these methods, can be used to perform the evaluation.

Further Design of Peptidomimetic Compounds

An additional, optional step of the drug design method of the present invention (block 36 of FIG. 4) is the design of additional peptidomimetic compounds, based on the structure and activity of previously evaluated, chemically modified analog(s). By reference to available data bases, such as the Cambridge crystallographic data base, replacement residues which are bioisosteric with various residues of the compound of interest can be identified and used to replace the native residue in the compound of interest. Those of skill in the art can readily identify suitable bioisosteric moieties which can be used in place of the naturally occurring amino acid residues. Examples of some commonly used bioisosteric moieties have been presented above.

An important consideration in designing the chemically modified analog, and the peptidomimetic as well, is to identify any flexible portions of the structure that should be replaced with suitable rigid or conformationally constrained bioisostere(s). Moreover, any portions or sections of the structure subject to degradation when the peptide structure is administered (e.g., by oral administration, intramuscular injection, intravenous injection, subcutaneous injection, or the like; with oral administration being the presently most preferred), may likewise be replaced with bioisosteres or equivalent that are not readily biologically degraded, and that maintain the desired binding between target peptides and receptors or peptidomimetics.

Once the desired peptidomimetic has been identified, chemical synthesis thereof may be undertaken employing standard synthetic techniques.

Examples

To illustrate the methods and systems of the present invention, the following examples of the calculation of the most probable peptide structure and the design of a peptidomimetic are presented.

Example 1: Tyr-βAla-Glu-Cys-βAla-DArg

The most probable conformation for a synthetic polypeptide, Thr-βAla-Glu-Cys-βAla-DArg, was calculated in accordance with the invention method described herein. Thus, the input file MASTER employed for the ab initio calculation was as follows:

ACE 4TYR BAL GLU CYS BAL RDO NH2 END wherein:
ACE is an acetyl group;
4TYR designates the dielectric constant (4) to be used for the medium in which the calculation is to be conducted, and TYR is a tyrosine residue;
BAL is a β-alanine residue;
GLU is a glutamic acid residue;
CYS is a cysteine residue;
RDO is a D-arginine residue;
NH2 is an amino group; and
END designates the end of the input file.

The above input file MASTER was then translated by LINK into a list of initial coordinates, using the data set forth in Table 2A. The initial coordinates employed also specify how the individual atom of the molecule are bonded to one another, as set forth in Table 2B.

TABLE 2A

| ATOM No. | AMINO ACID TYPE* | RES- IDUE | (NO.) | SPATIAL COORDINATES x | y | z |
|---|---|---|---|---|---|---|
| 1 | HA1 | ACE | (1) | −4.625 | −6.045 | −0.570 |
| 2 | CA | ACE | | −4.305 | −5.311 | 0.189 |
| 3 | HA2 | ACE | | −5.061 | −5.241 | 0.969 |
| 4 | HA3 | ACE | | −3.356 | −5.708 | 0.572 |
| 5 | C | ACE | | −4.062 | −3.986 | −0.481 |
| 6 | O | ACE | | −3.028 | −3.812 | −1.122 |
| 7 | N | TYR | (2) | −4.816 | −2.963 | −0.072 |
| 8 | HN | TYR | | −5.569 | −3.187 | 0.563 |
| 9 | CA | TYR | | −4.594 | −1.575 | −0.425 |
| 10 | HA | TYR | | −4.360 | −1.571 | −1.490 |
| 11 | CB | TYR | | −5.919 | −0.850 | −0.210 |
| 12 | HB1 | TYR | | −6.277 | −1.124 | 0.782 |
| 13 | HB2 | TYR | | −6.658 | −1.149 | −0.956 |
| 14 | CG | TYR | | −5.808 | 0.647 | −0.379 |
| 15 | CD1 | TYR | | −6.048 | 1.544 | 0.670 |
| 16 | HD1 | TYR | | −6.224 | 1.186 | 1.673 |
| 17 | CE1 | TYR | | −6.229 | 2.902 | 0.382 |
| 18 | HE1 | TYR | | −6.625 | 3.624 | 1.081 |
| 19 | CZ | TYR | | −5.768 | 3.415 | −0.836 |
| 20 | OH | TYR | | −5.547 | 4.756 | −0.958 |
| 21 | HOH | TYR | | −5.793 | 5.341 | −0.238 |
| 22 | CE2 | TYR | | −5.345 | 2.536 | −1.839 |
| 23 | HE2 | TYR | | −4.776 | 2.992 | −2.636 |
| 24 | CD2 | TYR | | −5.503 | 1.158 | −1.646 |
| 25 | HD2 | TYR | | −5.183 | 0.463 | −2.408 |
| 26 | C | TYR | | −3.386 | −0.911 | 0.220 |
| 27 | O | TYR | | −2.609 | −0.254 | −0.476 |
| 28 | N | BAL | (3) | −3.207 | −1.013 | 1.540 |
| 29 | HN | BAL | | −3.826 | −1.577 | 2.104 |
| 30 | CA | BAL | | −2.109 | −0.342 | 2.208 |
| 31 | HA1 | BAL | | −2.195 | −0.462 | 3.289 |
| 32 | HA2 | BAL | | −2.181 | 0.725 | 1.998 |
| 33 | CB | BAL | | −0.732 | −0.918 | 1.890 |
| 34 | HB1 | BAL | | −0.465 | −0.684 | 0.859 |
| 35 | HB2 | BAL | | −0.662 | −1.992 | 2.066 |
| 36 | C | BAL | | 0.294 | −0.220 | 2.773 |
| 37 | O | BAL | | 0.087 | 0.919 | 3.184 |
| 38 | N | GLU | (4) | 1.423 | −0.889 | 3.018 |
| 39 | HN | GLU | | 1.435 | −1.821 | 2.626 |
| 40 | CA | GLU | | 2.576 | −0.380 | 3.732 |
| 41 | HA | GLU | | 2.295 | 0.094 | 4.672 |
| 42 | CB | GLU | | 3.474 | −1.561 | 4.089 |
| 43 | HB1 | GLU | | 4.466 | −1.131 | 4.239 |
| 44 | HB2 | GLU | | 3.460 | −2.190 | 3.198 |
| 45 | CG | GLU | | 3.137 | −2.337 | 5.360 |

TABLE 2A-continued

| ATOM No. | AMINO ACID TYPE* | RES- IDUE | (NO.) | SPATIAL COORDINATES x | y | z |
|---|---|---|---|---|---|---|
| 46 | HG1 | GLU | | 3.974 | −2.998 | 5.583 |
| 47 | HG2 | GLU | | 2.177 | −2.849 | 5.288 |
| 48 | CD | GLU | | 3.136 | −1.515 | 6.640 |
| 49 | OE1 | GLU | | 4.106 | −0.747 | 6.822 |
| 50 | OE2 | GLU | | 2.148 | −1.574 | 7.402 |
| 51 | C | GLU | | 3.365 | 0.675 | 2.967 |
| 52 | O | GLU | | 4.070 | 1.462 | 3.595 |
| 53 | N | CYS | (5) | 3.345 | 0.752 | 1.635 |
| 54 | HN | CYS | | 2.708 | 0.181 | 1.088 |
| 55 | CA | CYS | | 4.131 | 1.737 | 0.917 |
| 56 | HA | CYS | | 4.099 | 2.667 | 1.081 |
| 57 | CB | CYS | | 5.573 | 1.269 | 0.748 |
| 58 | HB1 | CYS | | 6.086 | 1.027 | 1.699 |
| 59 | HB2 | CYS | | 6.122 | 2.077 | 0.266 |
| 60 | SG | CYS | | 5.517 | −0.141 | −0.386 |
| 61 | HSG | CYS | | 5.176 | 0.589 | −1.452 |
| 62 | C | CYS | | 3.458 | 2.015 | −0.420 |
| 63 | O | CYS | | 2.867 | 1.073 | −0.944 |
| 64 | N | BAL | (6) | 3.612 | 3.218 | −0.978 |
| 65 | HN | BAL | | 4.227 | 3.838 | −0.469 |
| 66 | CA | BAL | | 3.133 | 3.578 | −2.298 |
| 67 | HA | BAL | | 3.152 | 2.735 | −2.988 |
| 68 | HA2 | BAL | | 3.899 | 4.214 | −2.740 |
| 69 | CB | BAL | | 1.788 | 4.295 | −2.216 |
| 70 | HB1 | BAL | | 1.453 | 4.645 | −3.192 |
| 71 | HB2 | BAL | | 1.768 | 5.185 | −1 587 |
| 72 | C | BAL | | 0.684 | 3.370 | −1.723 |
| 73 | O | BAL | | −0.018 | 3.655 | −0.756 |
| 74 | N | RDO | (7) | 0.522 | 2.234 | −2.411 |
| 75 | HN | RDO | | 1.238 | 2.153 | −3.147 |
| 76 | CA | RDO | | −0.475 | 1.239 | −2.176 |
| 77 | HA | RDO | | −0.828 | 1.196 | −1.146 |
| 78 | CB | RDO | | 0.122 | −0.129 | −2.496 |
| 79 | HB1 | RDO | | −0.755 | −0.777 | −2.480 |
| 80 | HB2 | RDO | | 0.761 | −0.369 | −1.645 |
| 81 | CG | RDO | | 1.012 | −0.312 | −3.722 |
| 82 | HG | RDO | | 1.954 | 0.218 | −3.579 |
| 83 | HG2 | RDO | | 0.492 | 0.061 | −4.604 |
| 84 | CD | RDO | | 1.350 | −1.770 | −4.023 |
| 85 | HD1 | RDO | | 1.973 | −1.768 | −4.912 |
| 86 | HD2 | RDO | | 0.478 | −2.353 | −4.320 |
| 87 | NE | RDO | | 1.980 | −2.514 | −2.933 |
| 88 | HNE | RDO | | 1.379 | −3.079 | −2.350 |
| 89 | CZ | RDO | | 3.179 | −2.214 | −2.413 |
| 90 | NH1 | RDO | | 4.157 | −1.668 | −3.150 |
| 91 | N11 | RDO | | 4.047 | −1.510 | −4.141 |
| 92 | N12 | RDO | | 5.067 | −1.471 | −2.760 |
| 93 | NH2 | RDO | | 3.346 | −2.357 | −1.090 |
| 94 | H21 | RDO | | 2.592 | −2.517 | −0.438 |
| 95 | H22 | RDO | | 4.282 | −2.208 | −0.741 |
| 96 | C | RDO | | −1.701 | 1.650 | −2.982 |
| 97 | O | RDO | | −1.752 | 2.752 | −3.523 |
| 98 | | RDO | | | | |

*Atom types are abbreviated as follows:

HA1 refers to a hydrogen atom on the alpha carbon, and is the 1st of such hydrogen atoms; thus HA2 refers to the 2nd hydrogen atom on the alpha carbon;
CA refers to the alpha carbon;
C alone refers to the carbonyl carbon;
O alone refers to the carbonyl oxygen;
N alone refers to the amide nitrogen;
HN refers to the amide hydrogen;
CB refers to the beta carbon atom;
HB1, HB2 refers to the beta hydrogens,
CG refers to the gamma carbon;
CD1 refers to one of the delta carbon atoms, and CD2 refers to a second delta carbon atom;
HD1 and HD2 refer to hydrogen atoms on the delta carbons;
CE1 and CE2 refer to the epsilon carbon atoms;

HE1 and HE2 refer to hydrogen atoms on the epsilon carbons;

CZ refers to the zeta carbon;

OH refers to the hydroxyl oxygen;

HOH refers to the hydrogen of the hydroxy group;

HG1 and HG2 refer to the hydrogen atoms on the gamma carbons;

OE1 and OE2 refer to the oxygen atoms or the epsilon carbon;

SG refers to a sulfur atom on a gamma carbon;

HSG refers to the hydrogen atom on atom "SG";

NE refers to a nitrogen atom on an epsilon carbon; and

HNE is the hydrogen atom on atom "NE".

TABLE 2B

| Atom No. | Bound to Atom No. | | | |
|---|---|---|---|---|
| 1 | 2 | | | |
| 2 | 5 | 1 | 3 | 4 |
| 3 | 2 | | | |
| 4 | 2 | | | |
| 5 | 7 | 2 | 6 | |
| 6 | 5 | | | |
| 7 | 9 | 5 | 8 | |
| 8 | 7 | | | |
| 9 | 11 | 7 | 10 | 26 |
| 10 | 9 | | | |
| 11 | 14 | 12 | 13 | 9 |
| 12 | 11 | | | |
| 13 | 11 | | | |
| 14 | 15 | 15 | 11 | 24 |
| 15 | 17 | 16 | 14 | 14 |
| 16 | 15 | | | |
| 17 | 19 | 19 | 18 | 15 |
| 18 | 17 | | | |
| 19 | 22 | 20 | 17 | 17 |
| 20 | 19 | 21 | | |
| 21 | 20 | | | |
| 22 | 24 | 24 | 23 | 19 |
| 23 | 22 | | | |
| 24 | 25 | 22 | 22 | 14 |
| 25 | 24 | | | |
| 26 | 9 | 27 | 27 | 28 |
| 27 | 26 | | | |
| 28 | 26 | 29 | 30 | |
| 29 | 28 | | | |
| 30 | 28 | 31 | 32 | 33 |
| 31 | 30 | | | |
| 32 | 30 | | | |
| 33 | 30 | 34 | 35 | 36 |
| 34 | 33 | | | |
| 35 | 33 | | | |
| 36 | 33 | 37 | 38 | |
| 37 | 36 | | | |
| 38 | 36 | 39 | 40 | |
| 39 | 38 | | | |
| 40 | 38 | 41 | 42 | 51 |
| 41 | 40 | | | |
| 42 | 40 | 43 | 44 | 45 |
| 43 | 42 | | | |
| 44 | 42 | | | |
| 45 | 42 | 46 | 47 | 48 |

TABLE 2B-continued

| Atom No. | Bound to Atom No. | | | |
|---|---|---|---|---|
| 46 | 45 | | | |
| 47 | 45 | | | |
| 48 | 45 | 49 | 49 | 50 |
| 49 | 48 | 48 | | |
| 50 | 48 | | | |
| 51 | 40 | 52 | 52 | 53 |
| 52 | 51 | 51 | | |
| 53 | 51 | 54 | 55 | |
| 54 | 53 | | | |
| 55 | 53 | 56 | 57 | 62 |
| 56 | 55 | | | |
| 57 | 55 | 58 | 59 | 60 |
| 58 | 57 | | | |
| 59 | 57 | | | |
| 60 | 57 | 61 | | |
| 61 | 60 | | | |
| 62 | 55 | 63 | 63 | 64 |
| 63 | 62 | 62 | | |
| 64 | 62 | 65 | 66 | |
| 65 | 64 | | | |
| 66 | 64 | 67 | 68 | 69 |
| 67 | 66 | | | |
| 68 | 66 | | | |
| 69 | 66 | 70 | 71 | 72 |
| 70 | 69 | | | |
| 71 | 69 | | | |
| 72 | 69 | 73 | 74 | |
| 73 | 72 | | | |
| 74 | 72 | 75 | 76 | |
| 75 | 74 | | | |
| 76 | 74 | 77 | 96 | 78 |
| 77 | 76 | | | |
| 78 | 76 | 79 | 80 | 81 |
| 79 | 78 | | | |
| 80 | 78 | | | |
| 81 | 78 | 82 | 83 | 84 |
| 82 | 81 | | | |
| 83 | 81 | | | |
| 84 | 81 | 85 | 86 | 87 |
| 85 | 84 | | | |
| 86 | 84 | | | |
| 87 | 84 | 88 | 89 | |
| 88 | 87 | | | |
| 89 | 84 | 93 | 90 | |
| 90 | 89 | 92 | 91 | |
| 91 | 90 | | | |
| 92 | 90 | | | |
| 93 | 89 | 94 | 95 | |
| 94 | 93 | | | |
| 95 | 93 | | | |
| 96 | 76 | 97 | | |
| 97 | 96 | | | |

Starting with the initial coordinates set forth in Table 2A, the target molecule was "created", residue-by-residue starting with one residue, which was subjected to the shrinking and expanding steps of the invention to achieve a most probable conformation thereof, then the second residue was added, the process repeated, and so on. In this way, a series of results were obtained, as illustrated in Table 2C.

TABLE 2C

SIMULATION DATA FOR POLYPEPTIDE
Tyr—$\beta$Ala—Glu—Cys—$\beta$Ala—DArg—NH$_2$

| No. of Residues: | | 2 | |
|---|---|---|---|
| | ACE | TYR | |
| Atom #: | 1 | 2 | |
| $\phi$ angle: | NAD | 44 | |
| $\psi$ angle: | NAD | NAD | |
| $\omega$ angle: | −179 | NAD | |
| | | | 3 |
| | ACE | TYR | BAL |
| | 1 | 3 | 3 |
| | NAD | −69 | −84 |
| | NAD | −52 | NAD |

TABLE 2C-continued

SIMULATION DATA FOR POLYPEPTIDE
Tyr—βAla—Glu—Cys—βAla—DArg—NH$_2$

| | | | | | | |
|---|---|---|---|---|---|---|
| 177 | −176 | NAD | | | | |
| | | 4 | | | | |
| ACE | TYR | BAL | GLU | | | |
| 1 | 2 | 3 | 4 | | | |
| NAD | −172 | 180 | −165 | | | |
| NAD | −52 | −133 | NAD | | | |
| −170 | 177 | −143 | NAD | | | |
| | | 5 | | | | |
| ACE | TYR | BAL | GLY | CYS | | |
| 1 | 2 | 3 | 4 | 5 | | |
| NAD | −149 | 151 | 74 | −167 | | |
| NAD | 122 | 175 | −74 | NAD | | |
| 180 | 178 | −167 | −175 | NAD | | |
| | | 6 | | | | |
| ACE | TYR | BAL | GLU | CYS | BAL | |
| 1 | 2 | 3 | 4 | 5 | 6 | |
| NAD | −48 | 46 | 94 | −150 | 69 | |
| NAD | 135 | 2 | −38 | −53 | NAD | |
| 177 | −179 | −156 | 175 | 176 | NAD | |
| | | 7 | | | | |
| ACE | TYR | BAL | GLU | CYS | BAL | RDO |
| 1 | 2 | 3 | 4 | 5 | 6 | 7 |
| NAD | −72 | −77 | −71 | −154 | 66 | 86 |
| NAD | −50 | −32 | −25 | 151 | −107 | NAD |
| 170 | −177 | −159 | −178 | 174 | 157 | NAD |

*NAD = no angle defined at this site

Once this growth process is completed, an initial proposed structure for the target compound is obtained, as presented above for the seven residue species. The molecular dynamics simulation is then continued for an additional period of time (e.g., 50–100 picoseconds). The data from the molecular dynamics simulation is then collected at regular intervals (or, alternatively, the data is collected each time the root mean squared deviation of the $\phi$, $\psi$ values, bond length values, or the like, vary by more than some specified threshold value). The collected data are then analyzed to ascertain the most probable conformation for the target structure. This analysis may be carried out in a variety of ways, e.g., by the construction and analysis of differential Balaji plots, by analysis of the data employing pattern recognition techniques, and the like.

Once the most probable conformation of the target peptide has been determined, analog structures related thereto can be identified. This is done by first comparing the $\phi$, $\psi$ angles for each residue of target compound with the $\phi$, $\psi$ angles of constrained dipeptide analogs (which are determined as described below). Then the most probable conformation for such an analog structure having one or more of the appropriate constrained dipeptide analog(s) substituted therein is determined, using the methodology described above.

In this manner, a thioamide analog of the above-described hexapeptide is proposed:

Acetyl—X$_1$—X$_2$—Glu—Cys—βAla—DArg—NH$_2$, wherein X$_1$ is a thio-tyrosine residue, and X$_2$ is a thio-beta-alanine residue. The compound is then subjected to the ab initio techniques previously described to predict the most probable conformation of the analog structure. As shown in FIG. 11, the most probable conformation of the analog structure is substantially the same as the most probable conformation determined for the original target peptide.

Similarly, a cyclic analog of the above-described hexapeptide is proposed:

Acetyl—Y—Glu—Cys—βAla—DArg—NH$_2$, wherein Y is:

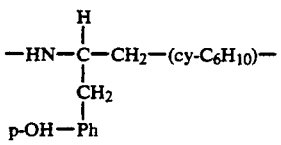

wherein —cy—C$_6$H$_{10}$— is a 1,4-disubstituted cyclohexyl group and p—OH—Ph— is a para-hydroxyphenyl group. Thus, the tyrosine and beta-alanine residues of the original target peptide have been replaced by the tyrosyl-cyclic species, Y.

The cyclic analog compound is then subjected to the ab initio techniques previously described to predict the most probable conformation of the analog structure. As shown in FIG. 11, the most probable conformation of the cyclic analog structure is substantially the same as the most probable conformation determined for the original target peptide.

Each of the analog structures may then be prepared employing standard synthetic techniques, after which each is tested for bioactivity. Those compounds which display bioactivity are candidate peptidomimetics, while those compounds which do not display bioactivity help define portions of the molecule which are particularly involved in imparting bioactivity to the subject compound. Where analog compounds are not bioactive, additional analog compounds are designed, subjected to the molecular dynamics simulation process of the present invention, and then tested for bioactivity. Additional analog structures are devised by either repeating the above-described process, seeking to render other portions of the target structure chemically modified, or by instead seeking to render chemically modified portions of the next most probable conformation (since the thermodynamically most probable conformation may not always be the biologically active form of the target peptide).

As a further, optional step, the pertinent physical and chemical properties (i.e., sites of hydrogen bonding, surface area, atomic and molecular volume, charge density, directionality of the charges, etc.) of biologically active analogs can be used to develop a collection of parameters required for the desired bioactivity. A database of known compounds (e.g., the Cambridge Crystal Structure Data Base, supra) can then be searched for structures which contain the steric parameters required for the desired bioactivity. Compounds which are found to contain the desired steric parameters are retrieved, and further analyzed to determine which of the retrieved compounds also have the desired electronic properties, relative to the target compound. Compounds that are found to contain both the desired steric and electronic properties are additional candidates as peptidominetics of the original target peptides search algorithms for three dimensional data base comparisons have been discussed previously.

Known compounds which also possess the collection of parameters required for the desired bioactivity may then be tested to see if they also possess the desired bioactivity. Alternatively, known compounds which also possess the collection of parameters required for the desired bioactivity may be modified to remove excess functionality which is not required for the particular bioactivity being tested. Such a modified compound may prove to be a simple, readily prepared peptidomimetic for the original target peptide.

Example 2: Poly-L-alanine

The procedure described in Example 1 was repeated to produce data from which a series of Balaji plots for $Ala_{30}$ (an oligomer of 30 alanine units) can be produced. See FIG. 13B for a series of representative Balaji plots for Poly-L-alanine as it is grown residue by residue.

The three dimensional coordinates were temporarily stored as each residue was added during the simulation, and the desired structural parameters (i.e., the $\phi$ and $\psi$ angles), were extracted. For the fully grown polypeptide, the simulation was continued, and at every picosecond the $\phi$ and $\psi$ angles were collected. Sample data during the simulation are given below in compressed format:

is observed after the number of amino acid residues have grown beyond 2 residues. The Balaji plot clearly shows that it adopts the right-handed $\alpha$-helical structure as depicted by a short segment of wedges around $-60°$. The C-terminus end has some irregular structure because of the choice of the $NH_2$ end group. The prediction of poly-L-alanine adopting an $\alpha$-helical structure is well supported in the prior art [See, for example, Blount, et al., *J. Am. Chem. Soc.* 82:3787–3789 (1960) and Kotelchuck & Scheraga, *Proc. Natl. Acad. Sci. U.S.A.* 62:1163–1170 (1988)].

Example 3: Polyglycine

The procedure described in Example 1 was repeated to produce a Balaji plot for $Gly_{40}$ (FIG. 14) which shows the high flexibility of conformation for the polyglycine. Examination of the dynamic simulations during chain growth shows many transitions from one structure to the other as expected for a flexible residue like glycine [See, for example, Ramachandran and Sasisekharan in *Prot. Chem.* 23:283–437 (1868)].

Example 4: Poly-L-proline

The procedure described in Example 1 was repeated to produce the Balaji plot for $Pro_{30}$ (FIG. 15) showing the extended structures possible for poly-L-proline, and the 3-dimensional plot (shown in FIG. 15A) illustrating the most probable conformation of poly-L-proline. The variability in $\phi$, $\psi$ angles is consistent with the left-handed threefold and fourfold structures possible for poly-L-prolines. (See, for example, Ramachandran and Sasisekharan, supra.)

Example 5: poly (Aib). poly-L-leucine, poly-L-isoleucine, poly-L-serine, poly-L-histidine, poly-L-phenylalanine and poly-L-aspartic acid The procedure described in Example 1 was repeated to produce Balaji plots for poly(Aib), poly-L-leucine and other homopolymers (FIGS. 16, 17, 18, 19, 20 and 21), as well as the 3-dimensional plots shown in FIGS. 17A and 18A, illustrating the most probable conformation of poly-L-leucine and poly-L-isoleucine.

During the simulation of $Aib_{35}$, a key transition (FIG. 16) from left-handed $3_{10}$ to right-handed $3_{10}$ helical structures and fluctuations around these structures was observed. Once a segment of a structure attains a criti-

```
RESIDUE NAME:  ACE ALA ALA ALA ALA ALA ALA ALA ALA ALA
ALA ALA ALA ALA ALA ALA ALA ALA ALA ALA ALA ALA ALA ALA
ALA ALA ALA ALA ALA ALA ALA ALA

RESIDUE NUMBERS:  1 2 3 4 5 6 7 8 9 10 11 12 13 14 15 16
17 18 19 20 21 22 23 24 25 26 27 28 29 30 31 32

φ VALUES:  NAD −67 −48 −55 −66 −62 −52 −57 −52 −57 −58
−62 −96 −45 −72 −52 −55 −74 −59 −52 −41 −68 −57 −92 50
−137 −70 54 −85 −65 −107

ψ VALUES:  NAD −34 −64 −40 −56 −42 −56 −54 −39 −57 −43
−44 45 46 26 70 −44 −51 −37 −55 −55 −79 −33 −36 33 −90 −6
−32 13 46 −29

ω VALUES:  NAD 160 165 0178 0176 0179 174 177 176 174 178
179 0177 0177 179 176 0164 176 0172 0176 173 174 −165 173
176 −171 177 −174 −174 178 165 174
```

*NAD = NO ANGLE DEFINED AT THIS SITE.

The Balaji plots were constructed from data such as that shown above for several dynamic simulations. The most probable conformation is shown in the Microfiche Appendix. Full development of the $\alpha$-helical structure cal length (>7 residues), the structure is stabilized in its configuration. These results are consistent with the available experimental data on Aib residues and molecular mechanical calculations [See, for example, Marshall & Bosshard, in *Circ. Res. (Suppl.* 2) 30/31:143-150 (1972); Burgess & Leach in *Biopolymers* 12: 2599-2605 (1973); and Pletnev, et al., in *Khim. Prir. Soedin.*9: 224-229 (1973)].

FIG. 16 shows that the simulation is predominantly an e-helical structure similar to poly-L-alanine. This is consistent with several previous studies, as noted above.

Simulations of other homopolymers like poly-L-isoleucine (FIG. 17); poly-L-serine (FIG. 18); poly-L-histidine (FIG. 19); poly-L-phenylalanine (FIG. 20); and poly-L-aspartic acid (FIG. 21) predict most probable structures which are consistent with the reported structures in the literature; see, for example, Ramachandran and Sasisekharan, supra.

Sample Conformational Energy Maps and Balaji Plots

Using the methods of the present invention, various peptides have been simulated and analyzed. Representative results from such simulations are presented in the figures that follow. Representative data, formatted as in the above examples, indicating the compilation of conformational features of several novel model oligopeptides, e.g., dipeptide analogs, are set forth below.

Figure 12:
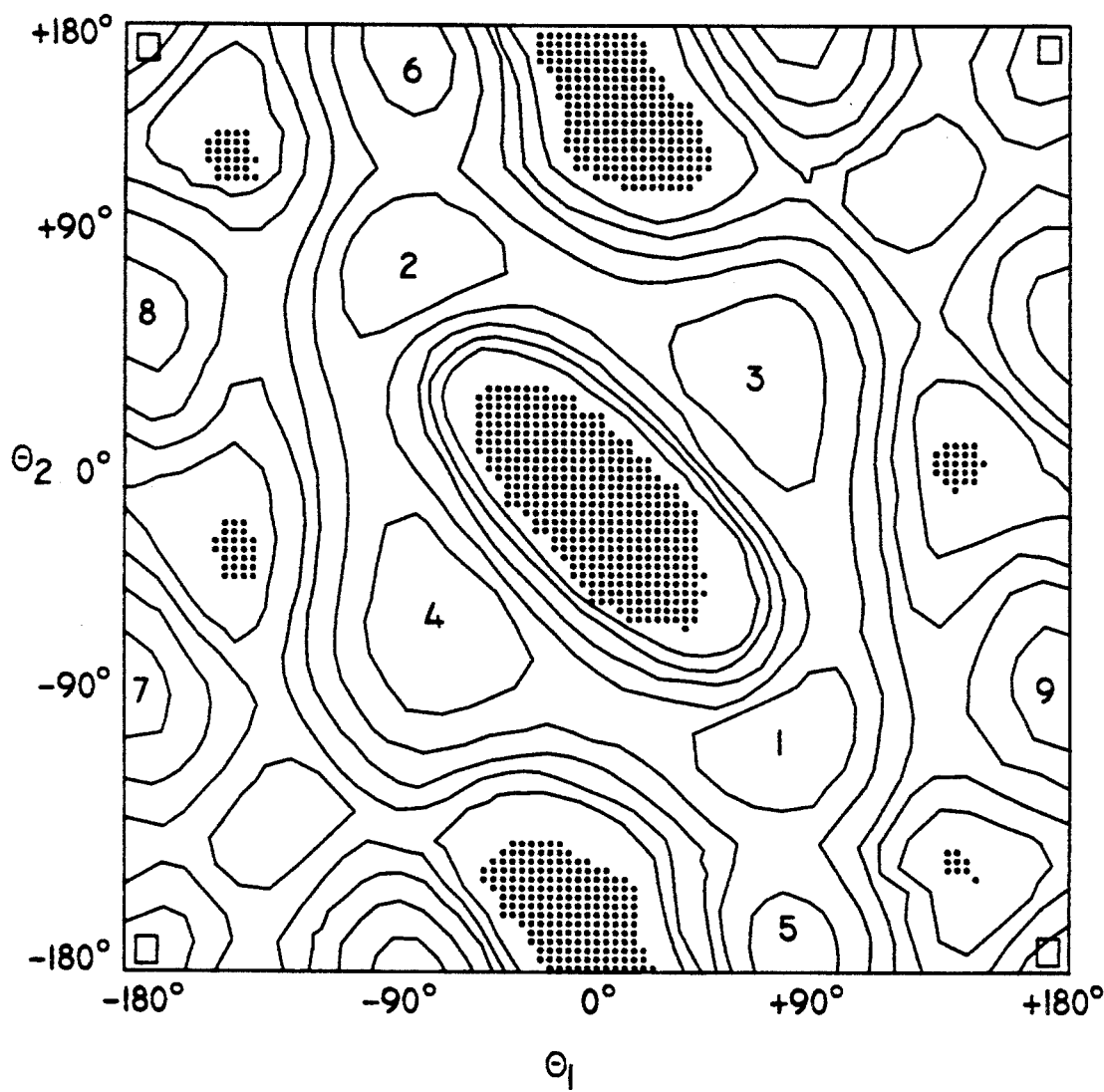
FIG. 12 shows a conformational energy map for a cyclopropyl dipeptide.

FIG. 12 shows a conformational energy map for a cyclopropyl dipeptide.

FIG. 13A shows a conformational energy map for an C-alanyl dithiopeptide;

FIG. 14 is a Balaji plot of polyglycine;
FIG. 15 is a Balaji plot of poly-L-proline;
FIG. 16 is a Balaji plot of poly(Aib);
FIG. 17 is a Balaji plot of poly-L-leucine;
FIG. 18 is a Balaji plot of poly-L-isoleucine;
FIG. 19 is a Balaji plot of poly-L-serine;
FIG. 20 is a Balaji plot of poly-L-histidine;
FIG. 21 is a Balaji plot of poly-L-phenylalanine; and
FIG. 22 is a Balaji plot of poly-L-aspartic acid.

As described herein, it is thus seen that the present invention provides a method of rational drug design that minimizes many of the problems or prior drug design methods and techniques. Significantly, such method advantageously predicts the most probable tertiary structures of a polypeptide, e.g., an oligopeptide, without any presumptions as to the conformation of the underlying primary or secondary structure.

As further described herein, it is seen that the present invention provides a set of useful analytical tools, e.g., Balaji plots, energy conformational maps, and probability maps, for readily identifying the most probable peptide structures, as well as those portions of the predicted peptide structure that are the most flexible and/or the most rigid. Such tools further provide additional insight into understanding tertiary and quaternary structures.

DESCRIPTION OF THE COMPUTER PROGRAMS

Described herein are the key computer programs used to carry out the rational drug design method of the present invention. Actual computer program listings for many of the computer programs, as well as samples of the data generated by such computer programs, are included in the Microfiche Appendix, submitted herewith. In general, conventional data handling programs or data conversion programs (e.g., used to transfer data from one file to another, or to convert data from one coordinate system to another) are not included nor described, as such can be readily written by those skilled in the art, or are commercially available. Further, those programs that are described do not necessarily provide all the possible variations that may be run using the present invention. However, the described programs are representative of all the key programs required to carry out the invention.

The computer programs described herein perform the following functions:

(1) carry out the ab initio simulation method of the present invention;
(2) generate Balaji plots, e.g., of the type shown in FIGS. 14-22; and
(3) generate conformational energy contour maps, e.g., of the type shown in FIGS. 9, 12 and 13, as well as contour probability data, e.g., of the type shown in FIG. 10.

A1. Ab Initio Simulation

The ab initio simulation method, as described herein, may be carried out using any suitable simulation computer program capable of shrinking and expanding of the peptides of interest. The best mode presently contemplated by the inventors for carrying out this simulation method is to break up the many and varied tasks carried out during the simulation process into individual programs and subroutines. A "batch" program is then invoked that causes the various programs to be run in the proper order and sequence to allow the ab initio simulation to proceed.

It is noted, of course, that this type of "batch processing" is not the only way the invention can be carried out. For example, a single ab initio program may be written, combining all the necessary processing steps of the ab initio process, and such single program could then be run. However, for the present time, the inventors have found it more advantageous for controlling, debugging, and maintaining the simulation process, to break the ab initio process into smaller segments, modules, or pieces, each having a specific function or functions, and to write (or otherwise acquire) specific computer programs to perform each function(s). Then, the batch program is used to control the particular sequence and manner in which the specific computer programs are run.

FIGS. 23A-23G contain a flow chart of the preferred batch program used at present to carry out the ab initio simulation of the present invention. This batch program flow chart is believed to be self-explanatory. However, the following comments are provided to aid in its understanding.

Figure 23A:
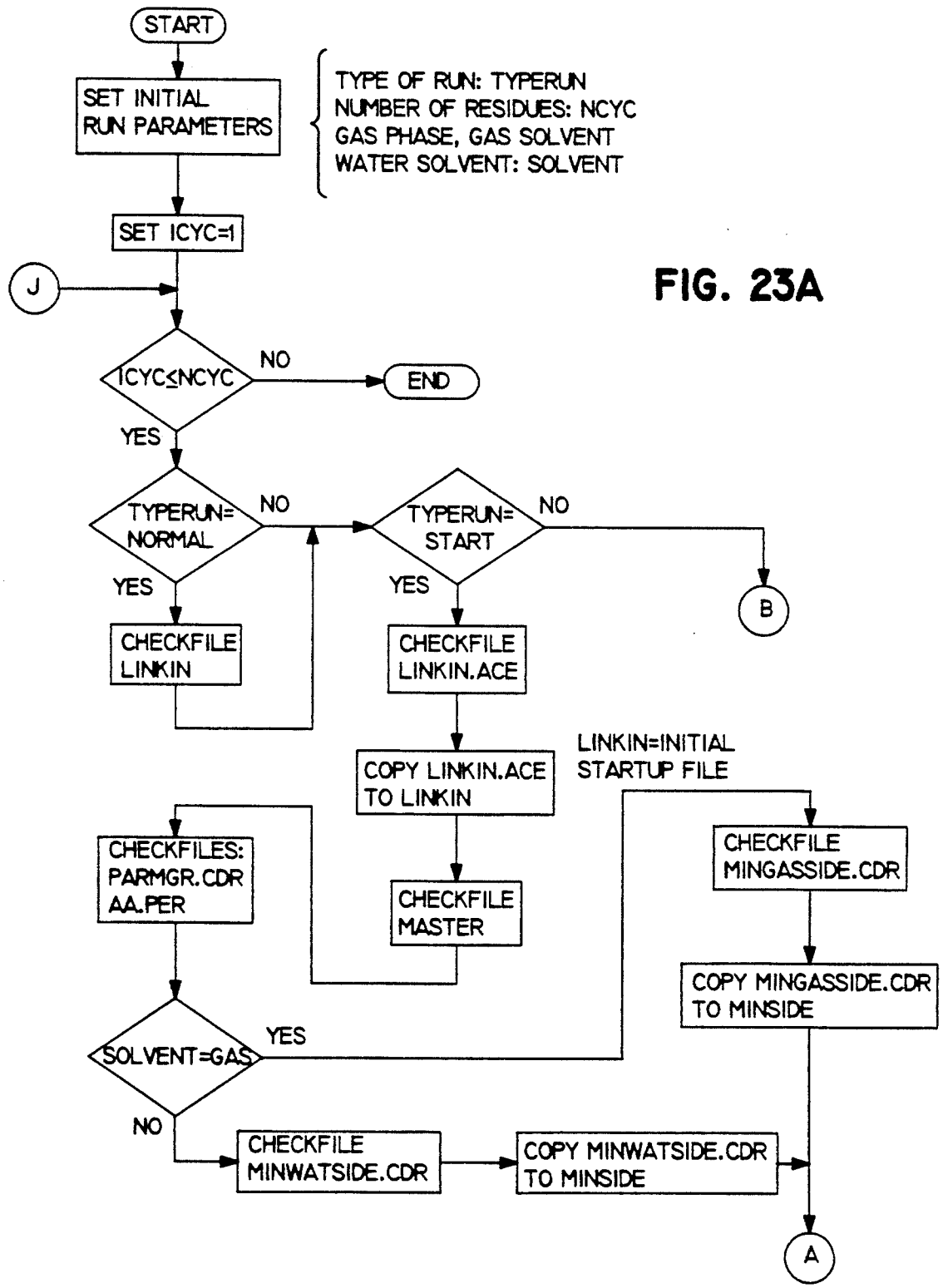

Each figure of FIGS. 23A-23G contains a portion of the overall flow chart, with upper case letters being used as connector designators showing the interconnection between the different figures. Thus, for example, FIG. 23A has one branch that terminates with designator "A", and one branch that terminates with designator "B". Both designator "A" and "B" are the starting points for branches appearing in FIG. 23B. FIG. 23A further has one designator "J" as an input branch. The designator "J" is an output branch of FIG. 23G.

When the batch program is initially started, the initial run parameters must be set. These parameters include the type of run, "typerun"; the number of residues, "ncyc"; and the type of solvent, "solvent". The type of run may be either a "normal" run or a "start" run. A start run is used when data is initially loaded into the simulation program. A normal run is a run after a start run, e.g., after the initial data has been loaded into the program and the growing or expanding process is carried out. Thus, the batch program is initially run with "typerun" set equal to "start". After this initial run, "typerun" is automatically set equal to "normal" (see FIG. 23G) and the batch program is repeated for as many residues as are specified by the parameter "ncyc".

Figure 23B:
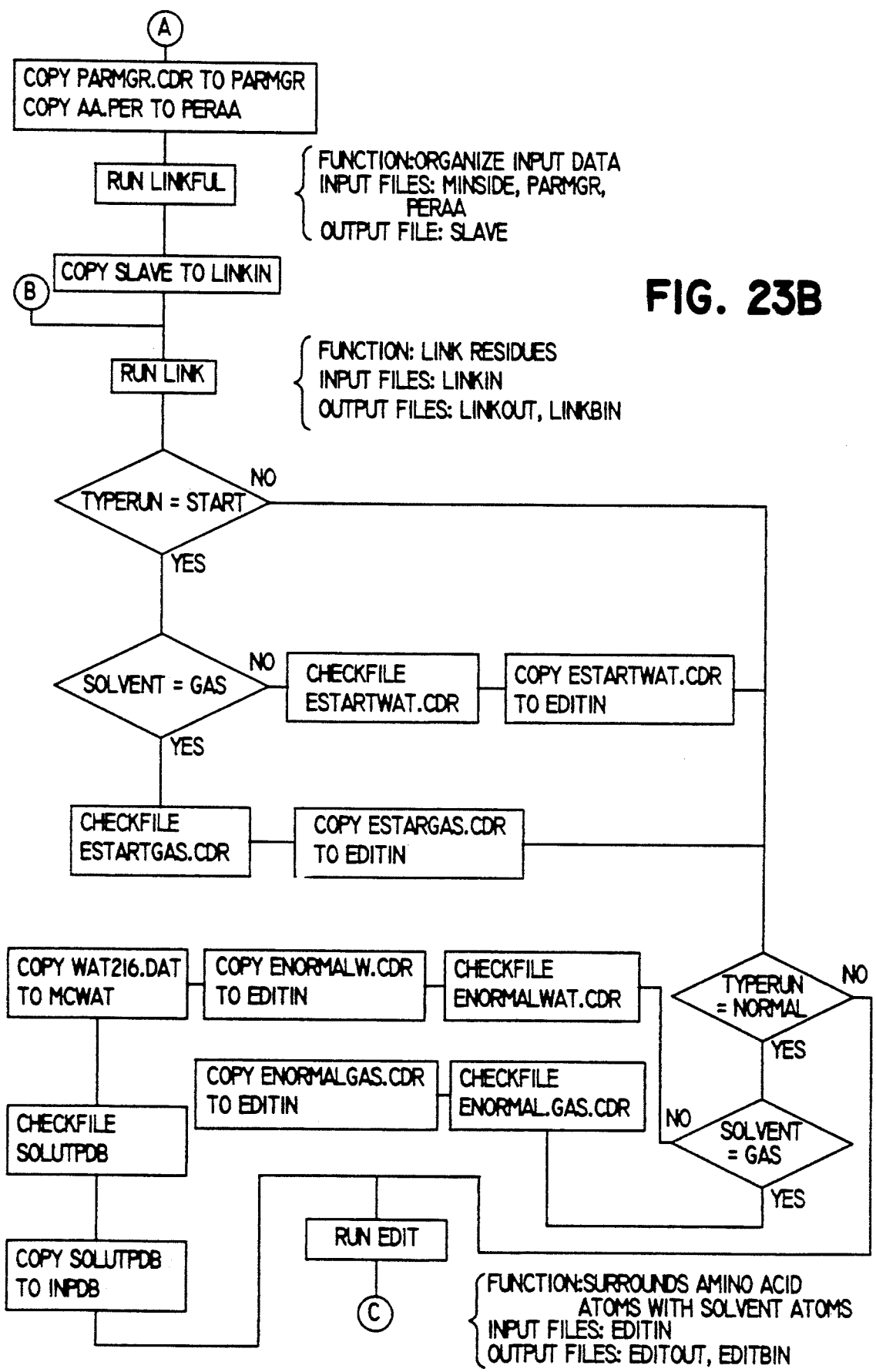
Figure 23C:
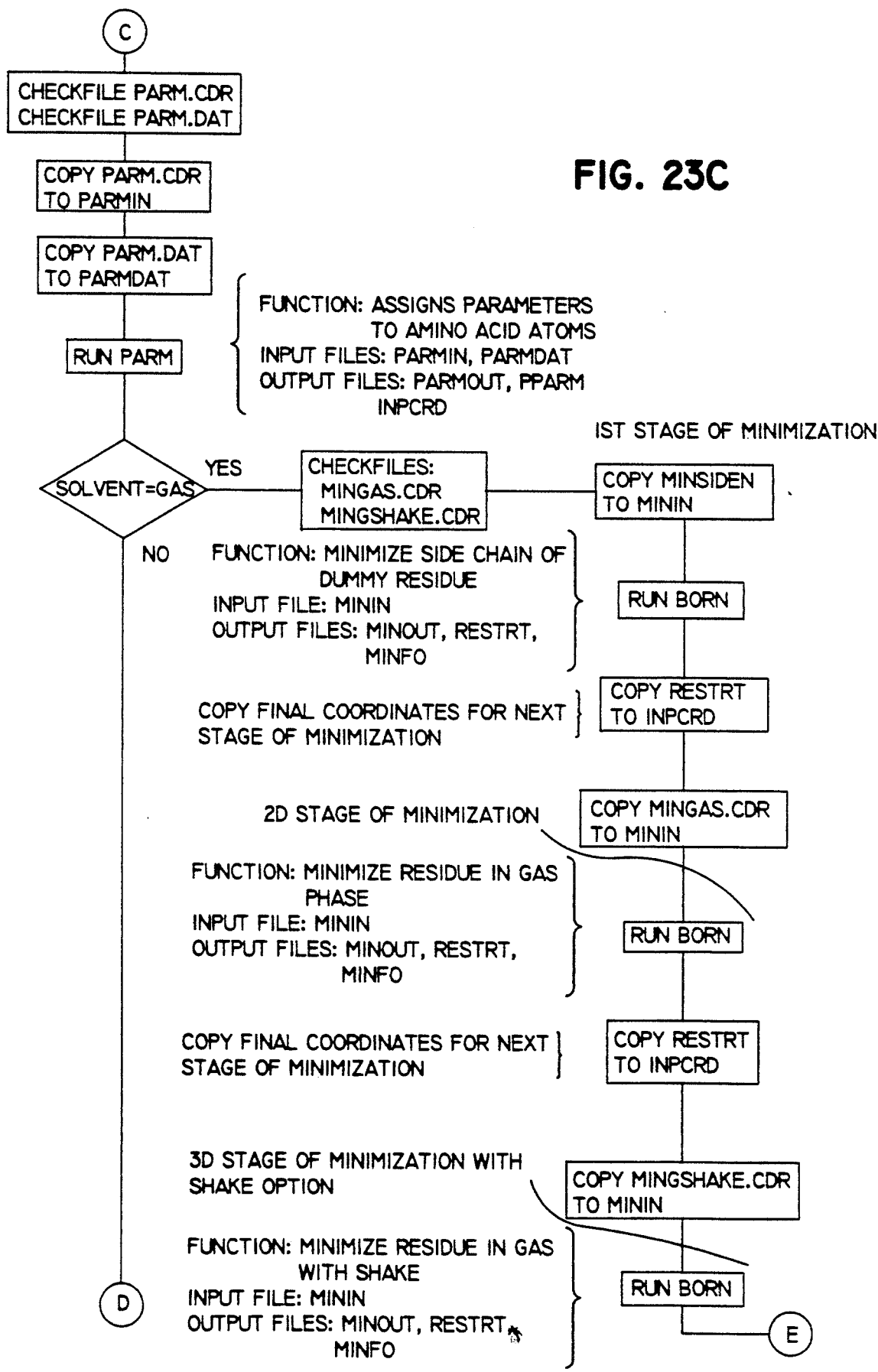

A control parameter, "icyc" keeps track of how many times the batch program has been run. Each time through the program "icyc" is incremented (FIG. 23G). When "icyc" is greater than "ncyc", the number of residues, then the program terminates.

As seen in FIGS. 23A–23G, there are numerous files, identified as "data input files" that are retrieved at various times. These data input files are identified by lower case letters with a three character extension, such as: linkin.ace; parmgr.cdr; parm.cdr; parm.dat; etc. A complete list of these data input files is presented below in Table A-1. Table A-1 also includes a brief description of the contents of each of the files listed. Representative samples of some of the data input files are included in the Microfiche Appendix, submitted herewith.

TABLE A-1

| File Name | Data Input Files<br>Description |
|---|---|
| aa.per | Amino Acid Perturbation data |
| enormalgas.cdr | Input for EDIT for "normal" run in "gasphase" |
| enormalwat.cdr | Input for EDIT for "normal" run in "water" |
| estartgas.cdr | Input for EDIT for "start" run in "gas phase" |
| estartwat.cdr | Input for EDIT for "start" run in "water" |
| linkin.ace | Input for LINK module |
| mingas.cdr | Input for BORN module for minimization in gas phase |
| mingasside.cdr | Input for BORN module for minimization of side chains in gas phase |
| mingshake.cdr | Input for BORN module for minimization in gas phase with SHAKE |
| minwatside.cdr | Input for BORN module for minimization of side chains in water |
| parm.cdr | Input for PARM module |
| parm.dat | Input for PARM module |
| parmgr.cdr | Input for PARM module for parameter assignment |
| pineqgas.cdr | Input for GIBBS module for equilibration in gas |
| pineqwat.cdr | Input for GIBBS module for equilibration in water |
| pingrgas.cdr | Input for GIBBS module for growth in gas |
| pingrgas0.cdr | Input for GIBBS module for growth in gas |
| pingrgas1.cdr | Input for GIBBS module for growth in gas |
| pingrgas2.cdr | Input for GIBBS module for growth in gas |
| pingrwat.cdr | Input for GIBBS module for growth in water |
| wat216.dat | Data file of box of water molecules for EDIT module |

As a general rule, when data is retrieved from one of the data input files, a "checkfile" command is issued to verify that the data file exists. If not, an error message is printed. If the data file does exist, its contents are typically copied to a "parameter file". The parameter files are identified by all upper case letters, e.g. "MINSIDE". (It is noted that the various computer programs or modules used as part of the batch program are also identified by all upper case letters.) For example, during the initial "start" run, as shown in FIG. 23A, a checkfile is made for the file "linkin.ace". If this data file exists, it is copied to the parameter file LINKIN.

It is noted that some of the "parameter files" (i.e., the files identified by all upper case letters) are not generated from data input files, but are rather output files generated by the various programs, modules, or subroutines that are run as part of the batch program. For example, as seen in FIG. 23B, when the program LINK is run, it generates the parameter files LINKOUT and LINKBIN as output files.

The various parameter files utilized as part of the batch program shown in FIGS. 23A–23G are identified below in Table A-2. Also included in Table A-2 is a brief description of each parameter file, i.e., what data it contains, or the source or destination of the data it contains. Representative samples of some of the parameter files are included in the computer program listings included in the Microfiche Appendix, submitted herewith.

TABLE A-2

| Parameter File | Ab Initio Parameter Files<br>Description | Destination or Source |
|---|---|---|
| SOLUTPDB | Coordinate File | Output from GIBBS to PDB Format |
| PARMGRN MASTER | Copied to PARMIN File q Amino Acid Resides to be Grown | Output from PARM Known literature |
| MINSIDEN | Current contents of File minside.cdr | Latest run of BORN |
| LINKIN | Input to LINK | Copied from linkin.ace or SLAVE |
| MINSIDE | Input to LINKFUL | Copied from linkin.ace or mingasside.cdr |
| PARMGR | Input to LINKFUL | Copied from parmgr.cdr |
| PERAA | Input to LINKFUL | Copied from aa.per |
| SLAVE | Copied to LINKIN | Temporary output file from LINKFUL |
| LINKOUT | Amino Acid Linking, and connectivity data | Output file from LINK |
| LINKBIN | Binary Linking Data for use by EDIT | Output file from LINK |
| EDITIN | Input to EDIT | Copied from estartwat.cdr, estartgas.cdr, enormalgas.cdr, or enormalwat.cdr |
| INPDB | Input PDB file | Copied from SOLUTPDB |
| MCWAT | Boxes of water Molecules | Copied from wat216.dat |
| EDITOUT | Data that describes Amino Acid Atoms surrounded by solvent atoms | Output file from EDIT |
| EDITBIN | Binary Data for use by PARM | Output file from EDIT |
| PARMIN | Input to PARM | Copied from parm.cdr |
| PARMDAT | Input to PARM | Copied from parm.dat |
| PARMOUT | Data that assigns parameters to atoms | Output file from PARM |
| PPARM | Perturbation Data | Output file from PARM |
| INPCRD | Initial Coordinate Data | Output file from PARM |
| MININ | Input to BORN | Copied from MINSIDEN |
| MINOUT | Output Coordinate Data from BORN | Output file from BORN |
| RESTRT | Minimized (Shrunk) Coordinate data | Output file from BORN |
| MINFO | Coordinate Data during minimization at an intermediate stage | Output file from BORN |
| PARMIN | Input to PARM | Copied from PARMGRN |
| PINCRD | Input Coordinate Data to GIBBS | Copied from RESTRT or PREST |

TABLE A-2-continued

Ab Initio Parameter Files

| Parameter File | Description | Destination or Source |
|---|---|---|
| PIN | Input to GIBBS | Copied from pineqgas.cdr, pingrgas0.cdr, pingrgas1.cdr, pingrgas2.cdr, pineqwat.cdr, or pingrwat.cdr |
| PREST | Coordinate Data | Output from GIBBS |
| POUT | Main Output Data from POUT | Output from GIBBS |
| PINFO | Intermediate Output | Output from GIBBS |
| SOLUT0PDB | PDB Coordinates | Copied from SOLUTPDB |
| SOLUT1PDB | PDB Coordinates | Copied from SOLUTPDB |
| SOLUT2PDB | PDB Coordinates | Copied from SOLUTPDB |

The computer programs that are run as part of the overall batch program of FIGS. 23A-23G are listed below in Table A-3. Computer program listings of the key programs required to carry out the ab initio simulation of the present invention are included in the Microfiche Appendix, submitted herewith.

TABLE A-3

Ab-Initio Computer Programs

| | |
|---|---|
| LINKFUL | BORN |
| LINK | PARM |
| EDIT | GIBBS |

The program LINKFUL performs the function of linking the amino acid atoms during a full growth option.

The program LINK performs the function of linking or connecting the amino acid atoms when the atoms are not at full size, i.e., when the atoms are shrunk or are less than full size.

The program EDIT performs the function of combining or surrounding the amino acid atoms with solvent atoms.

The program PARM performs the function of assigning various parameters, e.g., coordinates, bond lengths, etc., to the amino acid atoms.

The program BORN takes the data from the parameter file MININ, which data defines the minimization parameters and conditions, and minimizes the geometry of the amino acid residues to the optimum values. A program listing of the BORN program is included in the Microfiche Appendix submitted herewith.

Figure 23D:
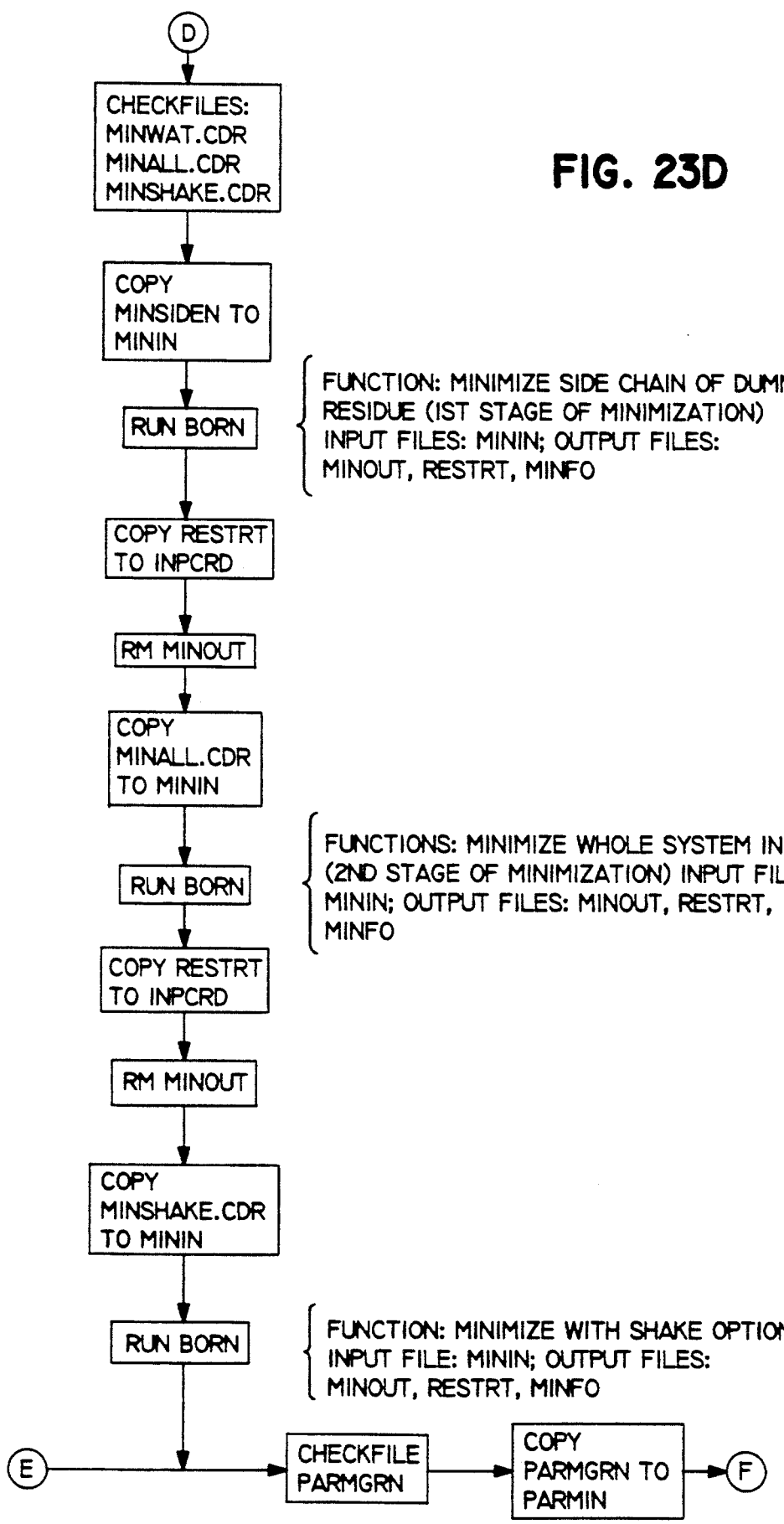

As seen in FIG. 23D, one of the options associated with running the BORN program is to perform the minimizing or shrinking with a shake option. The shake option is used to constrain the bond lengths to their equilibrium values. Without this option, some of the bonds might elongate or shrink to satisfy other properties of the system.

The program GIBBS expands the size of the simulated residue in accordance with a defined protocol as described in the specification. This is one of the key programs of the ad initio simulation program. A program listing of the GIBBS program is included in the Microfiche Appendix submitted herewith.

Figure 23E:
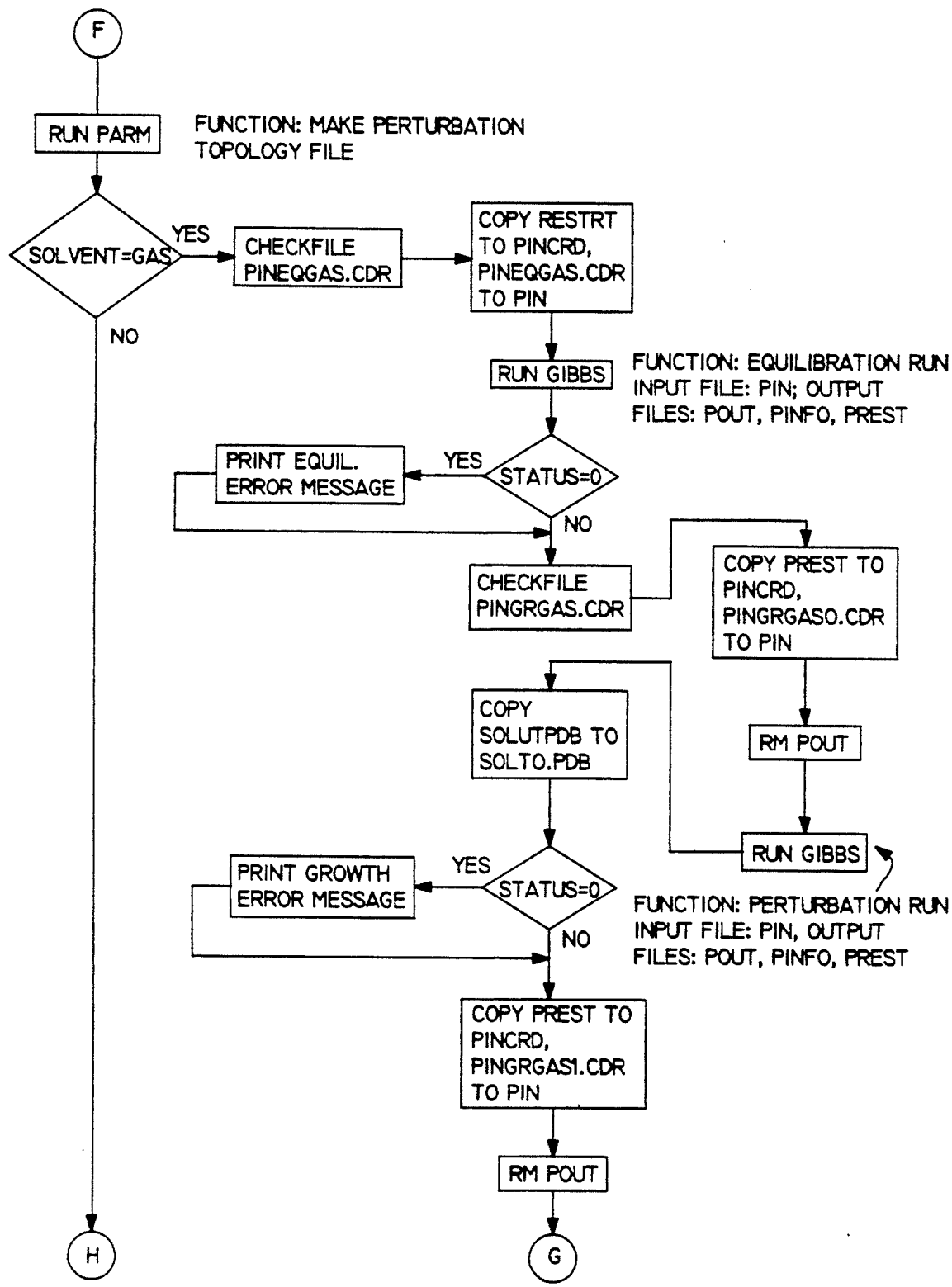
Figure 23F:
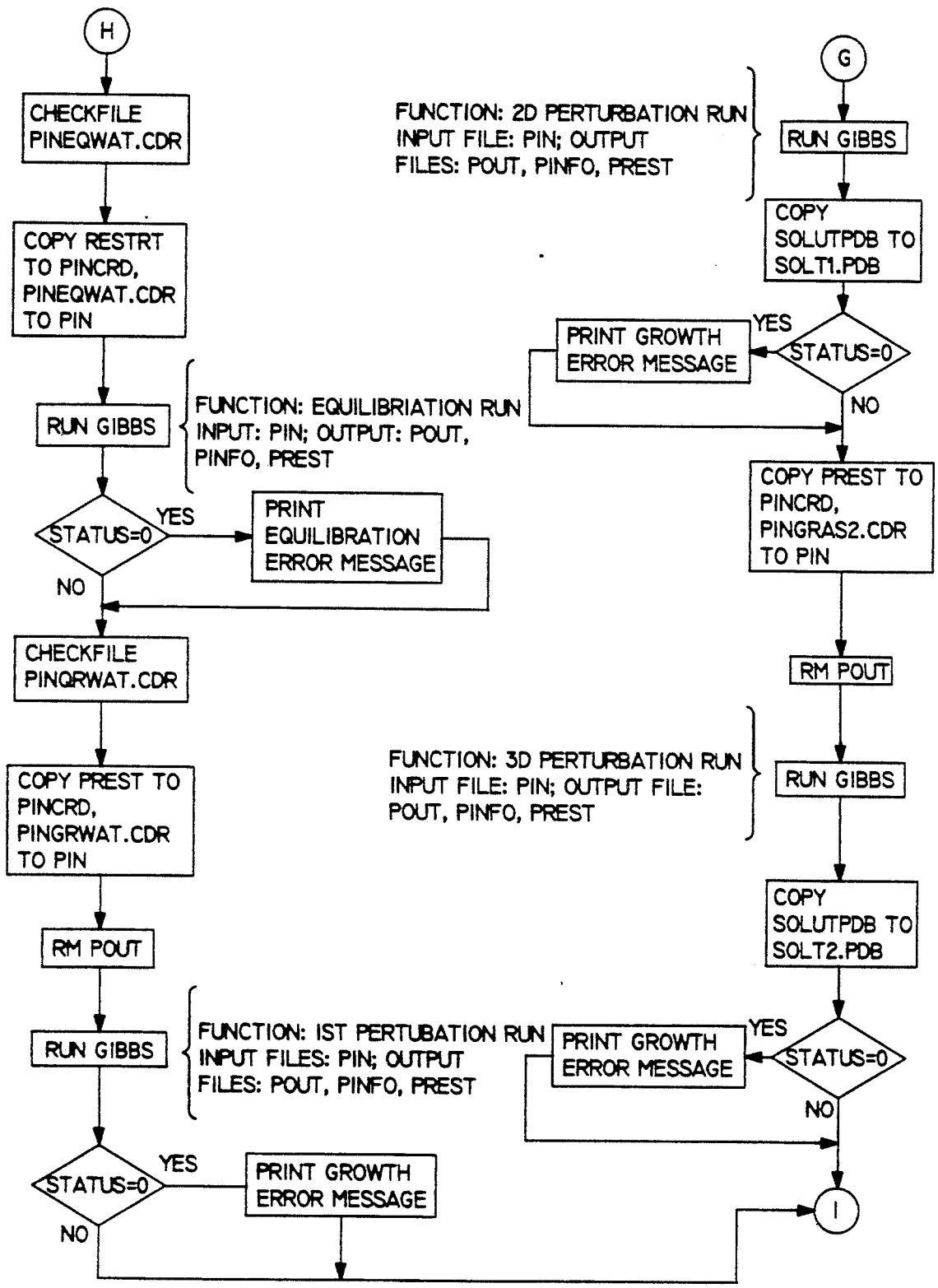
Figure 23G:
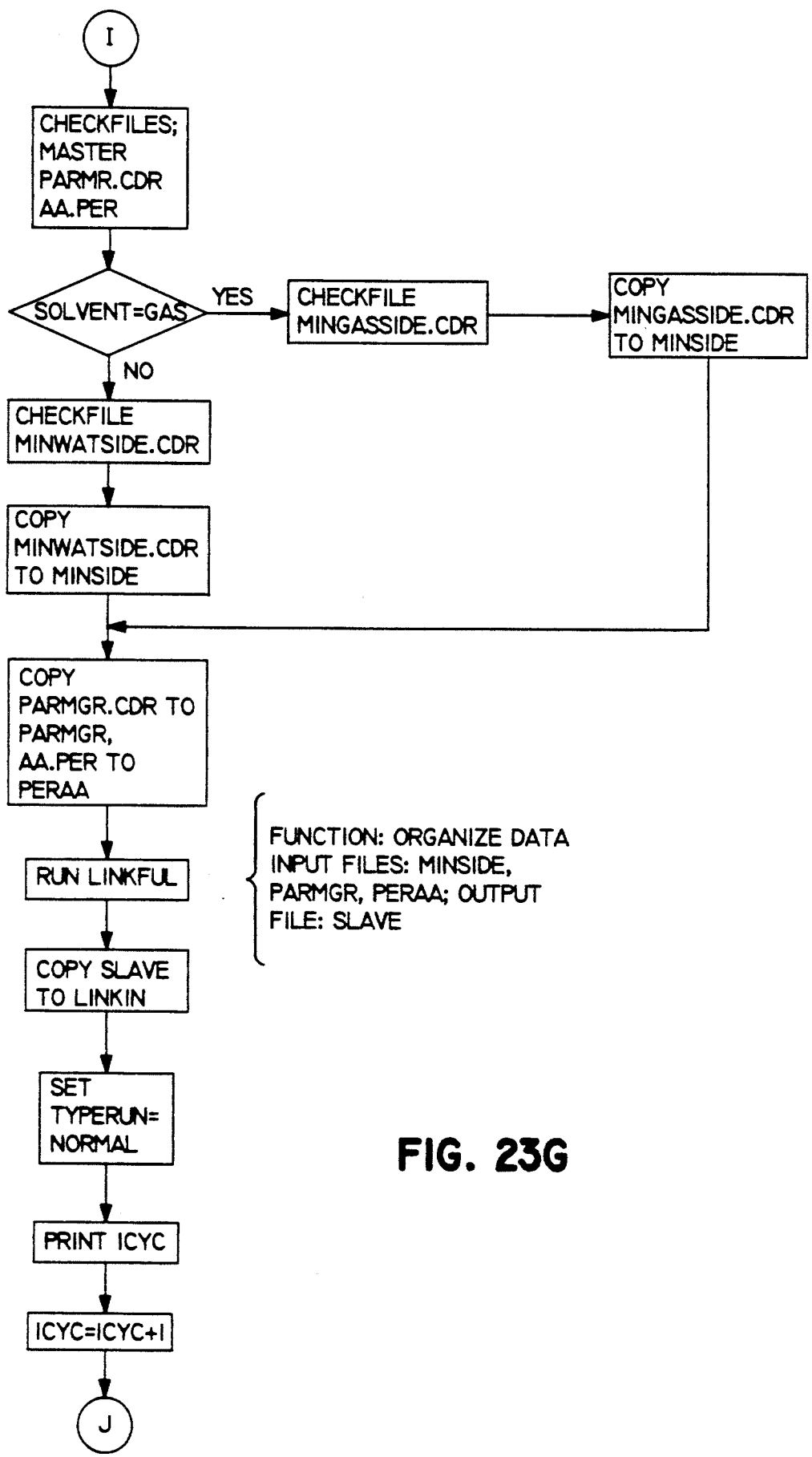

As seen in FIGS. 23E and 23F, GIBBS is run several times during the batch program. One run is referred to as an "Equilibration Run". The Equilibration Run is performed to bring the solvent and the solute to a Thermodynamic equilibrium before performing a perturbation. Another run of GIBBS, performed after the Equilibration Run, is one or more "Perturbation Runs". The Perturbation Run performs the growth of the molecules from a shrunk size to a normal size.

A2. Balaji Plots

The formation of Balaji plots is straightforward once the $\phi_i$, $\psi_i$ angle data for each residue, i, over the desired time intervals has been gathered, or is otherwise made available. The automatic generation of such plots is greatly facilitated through use of a computer. The program(s) used to generate such plots are included in the Microfiche Appendix, submitted herewith. One of the programs in the Microfiche Appendix is "PHIPSI". The PHIPSI program prints out the $\phi$, $\psi$ values after each step of growth.

A3. Conformational Energy Contour Maps; Contour Probability Data

The generation of the conformational energy contour maps, and contour probability data, of the type shown in FIGS. 9, 10, 12 and 13, is also greatly facilitated through the use of computer programs written specifically for this purpose. As indicated in the body of the specification (see the specification under the heading "The Conformational Energy Map"), a suitable molecular mechanics simulation program is utilized to assist in this effort. The preferred computer programs for accomplishing these functions are identified below in Table A-4. Computer program listings of the programs shown in Table A-4 that are not commercially available are included in the Microfiche Appendix submitted herewith.

In general, the protocol for generating the energy and contour maps proceeds as follows: (1) a molecule is created using a suitable Graphics package, such as MOGLI; and (2) a molecular mechanics calculation is performed using a suitable molecular mechanics package, such as AMBER or MMR, identified below in Table A-4. The molecular mechanics calculations are performed at 10° intervals for $\phi$, $\psi$ angles from 0° to 360°. The data from the molecular mechanics calculations is collected as the calculations are performed at each interval, and the data is then analyzed and/or plotted.

TABLE A-4

Programs Used to Generate Energy/Probability Maps

| Name of Program | Function of Program | Program Source |
|---|---|---|
| MOGLI Vs. 2.1 | Simulates a Molecule | EVANS & SUTHERLAND SLC, Utah |
| AMBER | Molecular Mechanics | U. C. Singh[1] |
| MMR | Molecular Mechanics | U. Burkert[2] |
| MP.MAP | Map Data For a Particular Molecule (See Microfiche Appendix for sample) | AMBER or MM2 Energy Calculations |
| TEMPMAP.DAT | Input Data used to create Contour Maps and evaluate Probabilities (See Microfiche Appendix for sample). | AMBER or MM2 |
| Map Protocol | Command Procedure (batch program) used to generate map prints. | Microfiche Appendix |
| Map_Prob.com | Command Procedure used to run analysis of energy data. | Microfiche Appendix |
| MP.ENR | Energy Map Data (See Microfiche Appendix for sample) | |

TABLE A-4-continued

| Name of Program | Function of Program | Program Source |
|---|---|---|
| | Programs Used to Generate Energy/Probability Maps | |
| MP.PRB | Porbability Map Data (See Microfiche Appendix for Sample) | |
| MP.PER | Percent Occupation on Energy Contour Data (See Microfiche Appendix for Sample) | |
| MP.PS | Plotted Energy Contour Map (See Microfiche Appendix for Sample, as well as FIGS. 9 and 12) | |
| Map_Prob.for | Extraction of Data from Energy Runs, and generation of probability and energy plots (used with standard VAX graphics utilities) | Microfiche Appendix |
| MAP88.FOR | Generates Energy Plots Only as f (φ, ψ) | Microfiche Appendix |
| POST3.FOR | Generates plots using Post Script Laser Printer | Microfiche Appendix |

[1] U. C. Singh, P. K. Weiner, J. S. Caldwell and P. A. Kollman, University of California, San Francisco, 1986. (AMBER version 3.3 is a fully vectorized version of AMBER version 3.0 and includes coordinate coupling, intra.inter decomposition and the option to include the polarization energy as part of the total energy.); See also, S. J. Weiner, P. A. Kollman, D. A. Chase, U. C. Singh, C. Ghio, G. Alagona, S. Profeta, Jr., and P. Weiner, J. Am. Chem. Soc., Vol. 106, p. 765 (1984).

[2] U. Burkert and N. L. Allinger, Molecular Mechanics, American Chemical Society, Washington, D.C. (1982); Note: The MMR force field for hydrocarbons was first described by N. L. Allinger, J. Am. Chem. Soc., Vol. 99, p. 8127 (1977). Extensions to functionalized molecules and all other sorts of special problems have been described in subsequent papers. The original version of the program (MM2(77)) is available from the Quantum Chemistry Program Exchange, University of Indiana Bloomington, Indiana 47405, Program 395.

In order to understand structure activity relationships of naturally occurring oligopeptide-based drugs, strategies to introduce constraints have been extensively explored. Through exploration of the conformational restrictions at the dipeptide level, e.g., by looking at peptide mimics such as thioamides, N-methyl peptides and side chain modifications like the introduction of Aib residues, substituted and unsubstituted cyclic propyl, butyl, pentyl ring and other similar structures, conformational features have been compiled of several peptide analogs. Such compilation may be described as a "data base" of conformational features. A systematic examination of such compilation, performed, e.g., using a computer, advantageously suggests peptide analog replacements (main chain as well as side chain modifications) in a target oligopeptide using appropriate similarity criteria, such as amino acid volume, surface area, charge, etc. Such compilation thus provides a valuable tool that is of immense use in identifying a bioactive conformation of a target oligopeptide and in the design of suitable peptidomimetic drugs.

The conformational features of several peptide analogs at the dipeptide level have been computed and compiled, and representative computations and compilations are included in the Microfiche Appendix, submitted herewith. These compilations are identified in the Microfiche Appendix as the "Data Base of Conformational Features". Further, representative moieties of such compilation include known peptide bond isosteres; dipeptide model compounds with side chain modification; as well as side chain substitutions. It is noted that conformational restrictions may also be achieved by cystine bridges and its analogs, as shown below.

An explanation illustrating the manner of using the information contained herein, and similar information, is presented in Balaji, et. al, "Mean Geometry of the Thiopeptide Unit and Conformational Features of Dithiopeptides and Polythiopeptides," *Biochemical and Biophysical Research Communications*, 145(2):834–841 (Jun. 15, 1987), which article is herein incorporated by reference.

TABLE B-1

| Peptide bond Isosteres reported in literature. |
|---|
| [CONCH3] N-methyl peptide |
| [CSNH] Thiopeptide (thioamide) |
| [CSNCH3] N-methyl thiopeptide |
| [COO] Ester isostere. |
| [CH(OH)CH2] Hydroxyethylene Isostere |
| [CH=CH] Double Bond Isostere |
| [CHCHO] Epoxide Isotere |
| [CH2CH2] Dimethylene Isostere |
| [CHOHCHOH] Diol Isostere |
| [CHOHCH=CHCO] Hydroxy Double Bond Isostere |
| [CHOHCHOHCHOHOHCO] Trihydroxy Isostere |
| [CHOHCH2] Hydroxyethylene Isostere |
| [COCH2] Ketomethylene Isostere |
| [CH2NH] Methyleneamino Isostere |
| [CH2NOH] Methylenehydroxyamino Isostere |
| [CH2S] Methylenethio Isostere |
| [CH2SO] Methylenethio Isostere |

Typical peptide isostere (including peptide) structures.

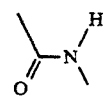

Peptide

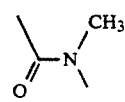

N-methyl peptide

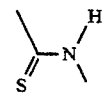

Thiopeptide (thioamide)

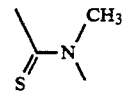

N-methyl thiopeptide (thioamide)

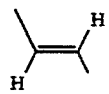

Double Bond Isostere

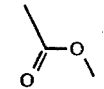

Ester Isostere

TABLE B-1-continued

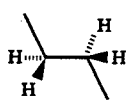

Dimethlene Isostere

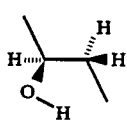

Hydroxyethylene moeity

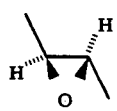

Epoxide Isostere

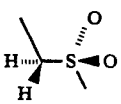

Methylenethio Isostere 1

Methylenethio Isostere 2

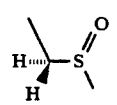

Methylenethio Isostere 3

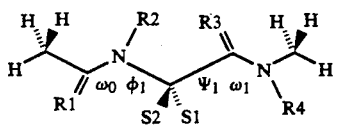

Dipeptide model compounds with side chain modifications.

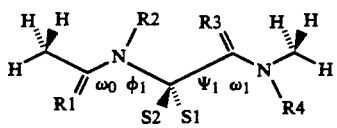

Typical dipeptide model compound studied (see Table I S2 = H; S1 = H and S1 = CH3 correspond to glycyl and L-alanyl side chains respectively. R1 and R3 can be O or S. R2 and R4 can be H and CH3. S1 = S2 = CH3 corresponds Aib (α-amino isobutyric acid) residue. Other compounds studied include S2 = H and S1 = C6H6 and S1 = S2 = C6H6 side chains.

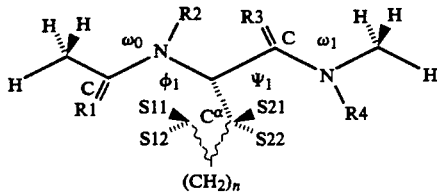

Typical dipeptide model compounds studied. See Table B-2 with cyclic side chains. S11, S12, S21, S22 either H or

TABLE B-1-continued

CH3 or combination of H and CH3. n = 0, 1, 2, 3, 4, 5 correspond respectively to cyclo-propyl, butyl, pentyl, hexyl, heptyl and octyl side chains. In many cyclic side chains different puckerd states are considered.

TABLE BI

Different peptide thiopeptide containing dipeptide like model compounds for a given side chain

| COMPOUND* NO. | R1 | R2 | R3 | R4 |
|---|---|---|---|---|
| 1 | O | H | O | H |
| 2 | O | CH3 | O | H |
| 3 | O | H | O | CH3 |
| 4 | O | CH3 | O | CH3 |
| 5 | S | H | S | H |
| 6 | S | CH3 | S | H |
| 7 | S | H | S | CH3 |
| 8 | S | CH3 | S | CH3 |
| 9 | S | H | O | H |
| 10 | S | CH3 | O | H |
| 11 | S | H | O | CH3 |
| 12 | S | CH3 | O | CH3 |
| 13 | O | H | S | H |
| 14 | O | CH3 | S | H |
| 15 | O | H | S | CH3 |
| 16 | O | CH3 | S | CH3 |

*Note:
When R2 = CH #, for the first peptide unit both cis and trans configurations are considered (leading a total 24 model compounds).

Presented herein is a representative data set of the amino acid residues that may be used with the ab initio techniques of the present invention. One table is included, Table C-1, which contains the data set for Alanine. Similar tables could readily be provided for the other possible amino acids. The data is conveniently organized into computer files adapted for use by the ab initio techniques of the present invention. Computer files for all of the amino acids used with the present invention are provided in the Microfiche Appendix submitted herewith. The names of these computer files are identified in Table C-2.

The data is formatted in Table C-1 in substantially the same way it is formatted in the computer files included in the Microfiche Appendix. An explanation of this format for Table C-1 follows.

At the top of Table C-1, to the left, is the term "ALANINE", identifying the particular amino acid for which the data set is applicable. Underneath this term is the name of the computer file where the ALANINE data is found: ALA.DBS.

The first two columns show the atom number and respective atom of Alanine. Note that as configured in Table C-1, the first three atoms are "dummy" atoms, identified by "DUMM". The first letter identifies the atom, while subsequent letters or numerals define conventional variations of the same. An explanation of these letters and/or numerals may be found in the explanation of Table 2A presented in connection with Example 1, discussed in the specification. The third column provides further information about the particular atom, e.g., atom species type. For example, HC means hydrogen attached to a carbon; CT means any $sp^3$ carbon; and CA means any $sp^2$ carbon. The third column is useful to identify proper force field parameters for assignment to the atoms.

The fourth column provides connectivity information associated with each of the atoms of the amino acid. Such information is provided by means of a single letter/number code, having the following significance:

M=main; E=end atom; S=a single branch is all that may be attached to the atom; B=two branches may be attached to the atom; and 3=three branches may be attached to the atom. The fifth, sixth and seventh columns provide reference atom numbers that are used in connection with the eighth, ninth and tenth columns to define an internal coordinate system and reference points for bond length, bond angles, and dihedral angles. For example, for the 4th atom "N", the fifth sixth and seventh columns provide the reference atom numbers relative to the bond length, bond angle, and dihedral angle information provided in the eight, ninth and tenth columns, respectively.

Below the ten columns described above, there is a matrix of data entitled "CHARGE". The numbers in this matrix represent the charge on the respective atoms beginning after the dummy atoms. Thus, as seen in column 2, there are 10 atoms in ALANINE, not counting the first three dummy atoms. Hence, the charge matrix includes ten numbers, one for each atom in ALANINE. The charge values included in the matrix are read first horizontally. Thus, the first number $-0.75456$ corresponds to the charge on N, the first non-dummy atom (atom #4) in column 2. The second number 0.32541 corresponds to the charge on HN, the second non-dummy atom (atom #5) in column 2; and so on, with the last number $-0.57859$ corresponding to the last non-dummy atom (atom #13) in column 2.

Below the charge matrix, another matrix is shown known as the "IMPROPER" matrix.

For some amino acids, there may also be "loop closing" information.

TABLE C-1

ALANINE
ALA.DBS

| 1 | 2 | 3 | 4 | 5 | 6 | 7 | 8 | 9 | 10 |
|---|---|---|---|---|---|---|---|---|----|
| 1 | DUMM | DU | M | 0 | −1 | −2 | 0.0000 | 0.0000 | 0.0000 |
| 2 | DUMM | DU | M | 1 | 0 | −1 | 1.4490 | 0.0000 | 0.0000 |
| 3 | DUMM | DU | M | 2 | 1 | 0 | 1.5220 | 111.1000 | 0.0000 |
| 4 | N | N | M | 3 | 2 | 1 | 1.3350 | 116.6000 | 180.0000 |
| 5 | HN | H | E | 4 | 3 | 2 | 1.0100 | 119.8000 | 0.0000 |
| 6 | CA | CT | M | 4 | 3 | 2 | 1.4490 | 121.9000 | 180.0000 |
| 7 | HA | HC | E | 6 | 4 | 3 | 1.0900 | 109.5000 | 300.0000 |
| 8 | CB | CT | 3 | 6 | 4 | 3 | 1.5250 | 111.1000 | 60.0000 |
| 9 | HB1 | HC | E | 8 | 6 | 4 | 1.0900 | 109.5000 | 60.0000 |
| 10 | HB2 | HC | E | 8 | 6 | 4 | 1.0900 | 109.5000 | 180.0000 |
| 11 | HB3 | HC | E | 8 | 6 | 4 | 1.0900 | 109.5000 | 300.0000 |
| 12 | C | C | M | 6 | 4 | 3 | 1.5220 | 111.1000 | 180.0000 |
| 13 | O | O | E | 12 | 6 | 4 | 1.2290 | 120.5000 | 0.0000 |

CHARGE

| −0.75456 | 0.32541 | 0.38159 | 0.01026 | −0.34851 |
| 0.09672 | 0.09672 | 0.09672 | 0.67424 | −0.57859 |

IMPROPER

| −M | CA | N | HN |
| CA | +M | C | O |

TABLE C-2

| Amino Acid Name | Data Set Computer File Name* | Amino Acid Name | Data Set Computer File Name |
|---|---|---|---|
| ALANINE | ALA.DBS | END GROUPS ACETYL AND NH2 | ACE.DAT NH2.DAT |
| PHENYLALANINE | PHE.DBS | ALPHA AMINO ISOBUTYRIC ACID | AIB.DBS |
| TYROSINE | TYR.DBS | D-ALA | ADO.DAT |
| VALINE | VAL.DAT | D-ARGININE | RDO.DAT |
| LYSINE | CYS.DBS | D-ASPARAGINE | NDO.DAT |
| PROLINE | PRT.DAT | D-ASPARTIC ACID | DDO.DAT |
| GLYCINE | GLY.DBS | D-CYSTEINE | CD1.DAT |
| LEUCINE | LEU.DBS | D-CYSTEINE (S-S BRIDGE) | CD2.DAT |
| ISOLEUCINE | ILE.DBS | D-GLUTAMINE | QDO.DAT |
| CYSTEINE | CYS.DBS | D-GLUTAMIC ACID | EDO.DAT |
| CYSTINE (S-S BRIDGE) | CYX.DBS | D-HISTIDINE (delta H) | HD1.DAT |
| METHIONINE | MET.DBS | D-HISTIDINE (delta epsilon) | HD2.DAT |
| GLUTAMIC ACID | GLU.DBS | D-HISTIDINE (+) | HD3.DAT |
| GLUTAMINE | GLN.DBS | D-ISOLEUCINE | IDO.DAT |
| ARGININE | ARG.DBS | D-LEUCINE | LDO.DAT |
| HISTIDINE DELTAH | HID.DBS | D-LYSINE | KDO.DAT |
| HISTIDINE EPSILONH | HIE.DBS | D-METHIONINE | MDO.DAT |
| HISTIDINE PLUS | HIP.DBS | D-PHENYLALANINE | FDO.DAT |
| TRYPTOPHAN | TRP.DBS | D-PROLINE | PDO.DAT |
| ASPARAGINE | ASN.DAT | D-SERINE | SDO.DAT |
| ASPARTIC ACID | ASP.DAT | D-THREONINE | TDO.DAT |
| SERINE | SER.DAT | D-TRYPTOPHAN | WDO.DAT |
| THREONINE | THR.DAT | D-TYROSINE | YDO.DAT |
| MONO GLUTAMATE | GLO.DAT | D-VALINE | VDO.DAT |

TABLE C-2-continued

| Amino Acid Name | Data Set Computer File Name* | Amino Acid Name | Data Set Computer File Name |
|---|---|---|---|
| GLUTAMATE | GLE.DAT | BETA-ALANINE | BAL.DAT |

*See Microfiche Appendix

While the invention herein disclosed has been described by means of specific embodiments and applications thereof, numerous modifications and variations could be made thereto by those skilled in the art without departing from the scope of the invention set forth in the claims.

What is claimed is:

1. A method for producing simulated, chemically modified peptide or peptidomimetic structure(s) which substantially mimic the energetically most probable three-dimensional structure of preselected less constrained polypeptide(s), said method comprising:

(1) determining the $\phi$ and $\psi$ angles for each residue included in the preselected polypeptide;

(2) comparing the $\phi$ and $\psi$ angles for each residue obtained in step (i) with the $\phi$ and $\psi$ angles for each residue of known polypeptide species;

(3) substituting a chemically modified moiety for at least one of the residues of the preselected polypeptide to produce a chemically modified peptide or peptidomimetic structure, wherein said chemically modified moiety has $\phi$ and $\psi$ angles which are substantially similar to the $\phi$ and $\psi$ angles of the residue that is replaced; and (4) chemically synthesizing and testing the bioactivity of the chemically modified peptide or peptidomimetic structure.

2. The method of claim 1, wherein steps (1), (2), and (3) are repeated sequentially, beginning with a first residue of the preselected, less constrained polypeptide, so as to produce chemically modified analog(s) having a tertiary structure that substantially mimics the energetically most probable tertiary structure of the preselected, less constrained polypeptide(s).

3. A method for generating biologically or pharmacologically active molecules, comprising:

(a) determining the amino acid sequence of the hypervariable region of a monoclonal antibody having biological or phamacological activity, and (b) producing a peptidomimetic compound based on the amino acid sequence of step (a), wherein the peptidomimetic compound substantially retains the biological or pharmacological activity of said monoclonal antibody, wherein said peptidomimetic compound is produced by:

(i) determining the energetically most probably $\phi$ and $\psi$ angles for each residue included in the hypervariable region of said monoclonal antibody, (ii) comparing the $\phi$ and $\psi$ angles for each residue obtained in step (i) with the $\phi$ and $\psi$ angles for each residue of known polypeptide species, and (iii) substituting a chemically modified moiety for at least one of the residues of the pharmaceutically active compound, wherein said chemically modified moiety has $\phi$ and $\psi$ angles which are substantially similar to the $\phi$ and $\psi$ angles of the residue to be replaced.

* * * * *

UNITED STATES PATENT AND TRADEMARK OFFICE
CERTIFICATE OF CORRECTION

PATENT NO. : 5,331,573
DATED : July 19, 1994
INVENTOR(S) : Balaji, et al.

It is certified that error appears in the above-indentified patent and that said Letters Patent is hereby corrected as shown below:

- COLUMN 3, LINE 60, CHANGE "$\psi_{yi}$" TO -- $\psi_i$ --;

- COLUMN 10, LINE 57, DELETE "AND" FROM THE END OF THE LINE;

- COLUMN 52, LINE 7, CHANGE "TABLE BI" TO --TABLE B-2--;

- COLUMN 52, BETWEEN LINES 28 AND 29, INSERT THE ATTACHED FIVE (5) MISSING PAGES.

Signed and Sealed this

Sixteenth Day of April, 1996

BRUCE LEHMAN

Attest:

Attesting Officer

Commissioner of Patents and Trademarks

Side chain modifications - Aromatic and Heteromatic substituted amino acid derivatives.
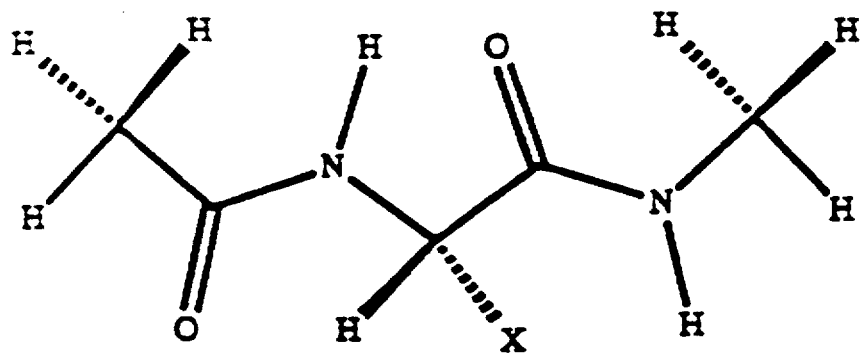
TABLE B-3
L-Aromatic and -Heteroaromatic Substituted
Amino Acid Derivatives
---
X
---
$C_6H_6$
4-$C_6H_4$OH
4-$C_6H_4$OCH$_3$
2OH-5-CH$_3C_6H_3$
2-$C_{10}H_7$
2-furnyl
5-CH$_3$-2-pyrrolyl
1-CH$_3$-2-pyrrolyl
2-thienyl
3-thienyl
beonzo[b]furan-2yl
indo-3-yl
benzo[b]thien-2-yl
---

Some representative dipeptide models.
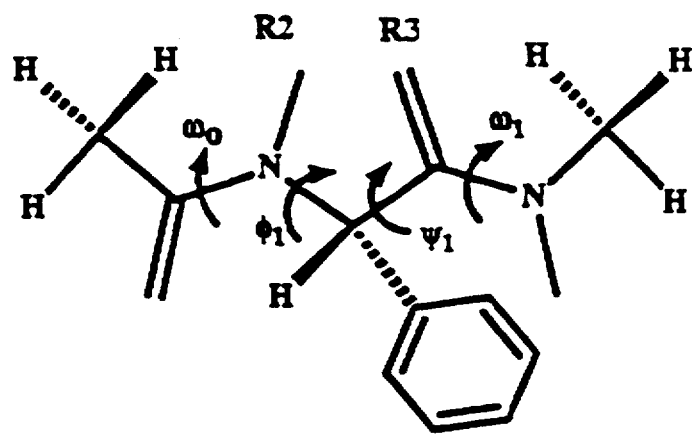
L-Benzyl dipeptide
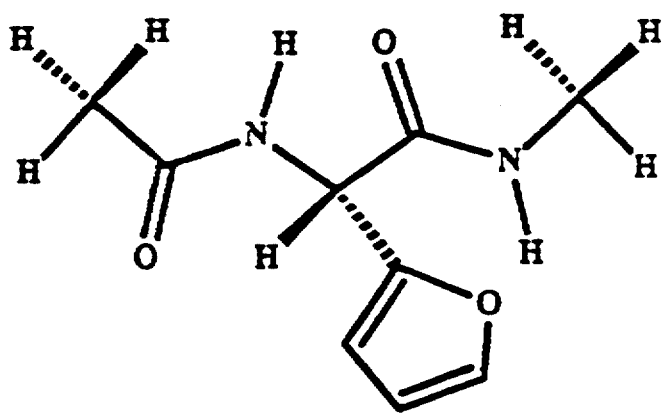
2-furnyl-dipeptide

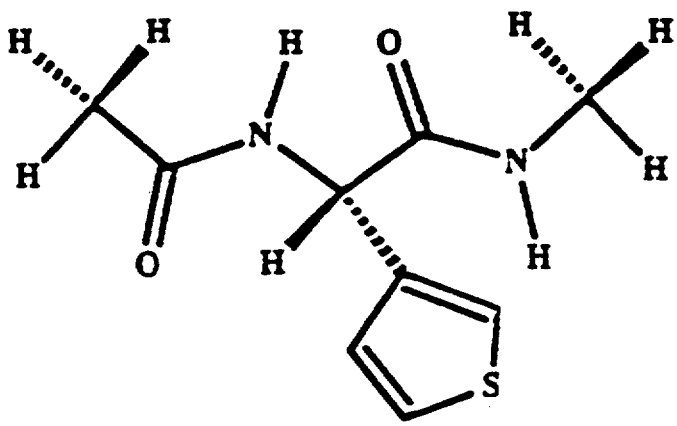
3-thiophene dipeptide.
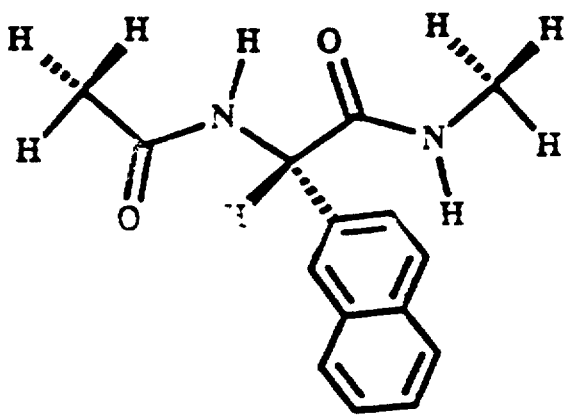
2-napthylene dipeptide.

Conformational Restrictions by cystine bridges and its analogs.

Conformational freedom can be restricted by the use of disulfide or thioether linkages between cystine side chains as shown below. If the side chain being replaced is of importance to the biological activity of the peptide, L-2-thiolhistidine residue (HisS) can be used and also disulfide bridge like features can also be incorporated as shown in the following illustrations.

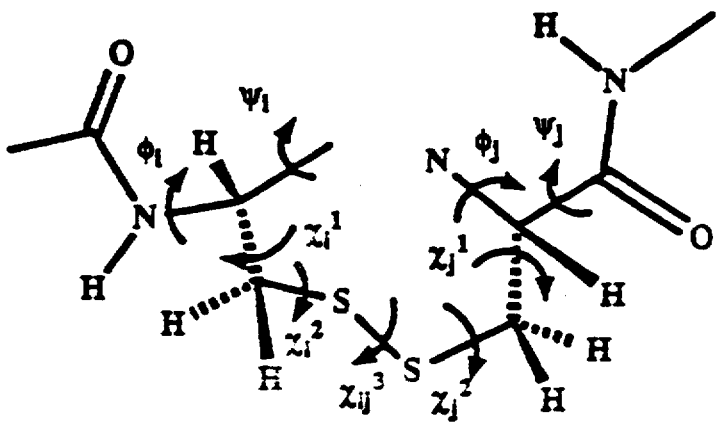

Cystine disulfide bridge in oligopeptide between i-t and j-th cystein residues.

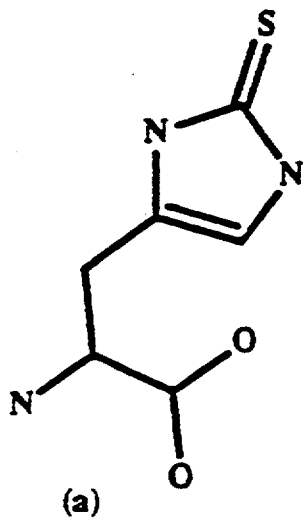
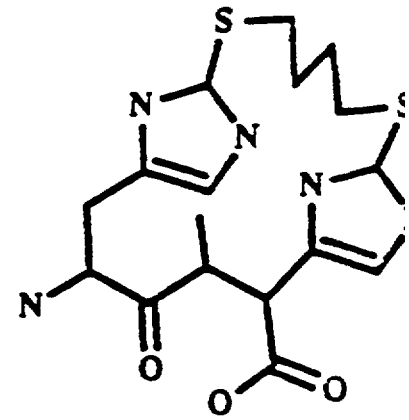

(a) L-2-thiolhistidine residue. (b) Cystine ty] disulfide bridge analog.

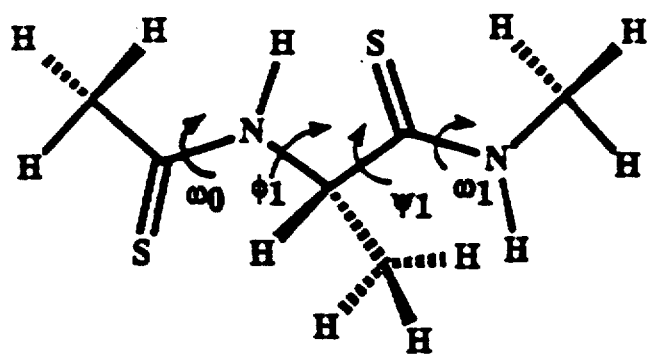
Alanyl dithiopeptide unit.